(12) United States Patent
Mellinghoff et al.

(10) Patent No.: US 10,632,121 B2
(45) Date of Patent: Apr. 28, 2020

(54) PLATELET-DERIVED GROWTH FACTOR RECEPTOR MUTATIONS AND COMPOSITIONS AND METHODS RELATING THERETO

(71) Applicant: MEMORIAL SLOAN KETTERING CANCER CENTER, New York, NY (US)

(72) Inventors: Ingo Kai Mellinghoff, New York, NY (US); Sara Kubek, Seattle, WA (US)

( * ) Notice: Subject to any disclaimer, the term of this patent is extended or adjusted under 35 U.S.C. 154(b) by 0 days.

(21) Appl. No.: 15/311,582

(22) PCT Filed: May 15, 2015

(86) PCT No.: PCT/US2015/031129
§ 371 (c)(1),
(2) Date: Nov. 16, 2016

(87) PCT Pub. No.: WO2015/175966
PCT Pub. Date: Nov. 19, 2015

(65) Prior Publication Data
US 2017/0087159 A1     Mar. 30, 2017

Related U.S. Application Data

(60) Provisional application No. 61/994,500, filed on May 16, 2014.

(51) Int. Cl.
| | | |
|---|---|---|
| *A61K 31/519* | (2006.01) | |
| *A61K 31/498* | (2006.01) | |
| *A61K 31/436* | (2006.01) | |
| *A61K 45/06* | (2006.01) | |
| *A61K 31/5377* | (2006.01) | |

(52) U.S. Cl.
CPC .......... *A61K 31/519* (2013.01); *A61K 31/436* (2013.01); *A61K 31/498* (2013.01); *A61K 31/5377* (2013.01); *A61K 45/06* (2013.01)

(58) Field of Classification Search
CPC .. A61K 31/519; A61K 31/5377; A61K 45/06; A61K 31/436; A61K 31/498
See application file for complete search history.

(56) References Cited

U.S. PATENT DOCUMENTS

2011/0212053 A1    9/2011  Qian et al.

OTHER PUBLICATIONS

International Search Report for PCT/US2015/31129.
Written Opinion for PCT/US2015/31129.
Fan et al., "A dual PI3 kinase/mTOR inhibitor reveals emergent efficacy in glioma," Cancer Cell. May 2006; vol. 9 No. 5, pp. 341-349.

(Continued)

*Primary Examiner* — Angela C Brown-Pettigrew
(74) *Attorney, Agent, or Firm* — Grimes & Yvon LLP

(57) ABSTRACT

In certain embodiments the present invention involves methods of killing tumor cells that comprise an oncogenic PDGFR mutation, and methods of treating subjects having tumors that comprise such tumor cells. In some embodiments such methods involve using PI3K inhibitors, or a combination of a PI3K inhibitor and an mTOR inhibitor, or a dual PI3K/mTOR inhibitor. The present invention also provides methods for determining whether a subject is a candidate for treatment, methods for evaluating the efficacy of treatment, and other methods, compositions, model systems, and assays.

17 Claims, 33 Drawing Sheets

(56) References Cited

OTHER PUBLICATIONS

Wen et al., "Current clinical development of PI3K pathway inhibitors in glioblastoma." Neuro Oncol. Jul. 2012, vol. 14, No. 7, pp. 819-829.

Paugh et al., "Novel oncogenic PDGFRA mutations in pediatric high-grade gliomas." Cancer Res.,Oct. 15, 2013, vol. 73, No. 20, pp. 6219-6229.

Clinical trial No. NCT01240460, "Exploratory Study of XL765 (SAR245409) or XL 147 45 (SAR245408) in Subjects With Recurrent Glioblastoma Who Are Candidates for Surgical Resection." ClinicaiTrials.gov, Jul. 2012 [online]. [Retrieved on Jul. 30, 2015]. Retrieved from the Internet <URL: https://clinicaltrials.gov/ct2/show/study/NCT01240460.

Andrae et al. "Role of platelet-derived growth factors in physiology and medicine"(2008). Genes Dev. 22, 1276-1312.

Bagci-Onder et al. "A Dual PI3K/mTOR Inhibitor, PI-103, Cooperates with Stem Cell Delivered TRAIL in Experimental Glioma Models" (2011). Cancer Res. 71, 154-163.

Brennan et al. "The somatic genomic landscape of glioblastoma." (2013). Cell 155, 462-477.

Cerami et al. "The cBio cancer genomics portal: an open platform for exploring multidimensional cancer genomics data" (2012). Cancer Discov. 2, 401-404.

Cloughesy et al. "Antitumor Activity of Rapamycin in a Phase I Trial for Patients with Recurrent PTEN-Deficient Glioblastoma" (2008). PLoS Med. 5, e8.

Gao et al. "Integrative analysis of complex cancer genomics and clinical profiles using the cBioPortal." (2013). Sci. Signal. 6, p. I1.

Koul et al. "Antitumor activity of NVP-BKM120—a selective pan class I PI3 kinase inhibitor showed differential forms of cell death based on p53 status of glioma cells" (2012). Clin. Cancer Res. 18, 184-195.

Liu et al. "NVP-BEZ235, a novel dual phosphatidylinositol 3-kinase/mammalian target of rapamycin inhibitor, elicits multifaceted antitumor activities in human gliomas" (2009). Mol. Cancer Ther. 8, 2204-2210.

Mellinghoff "Will Kinase Inhibitors Make it as Glioblastoma Drugs?" (2012). Curr. Top. Microbiol. Immunol. 355, 135-169.

Mellinghoff et al. "Molecular Determinants of the Response of Glioblastomas to EGFR Kinase Inhibitors" (2005). N. Engl. J. Med. 353, 2012-2024.

Prasad et al. "Inhibition of PI3K/mTOR pathways in glioblastoma and implications for combination therapy with temozolomide." (2011). Neuro. Oncol. 13, 384-392.

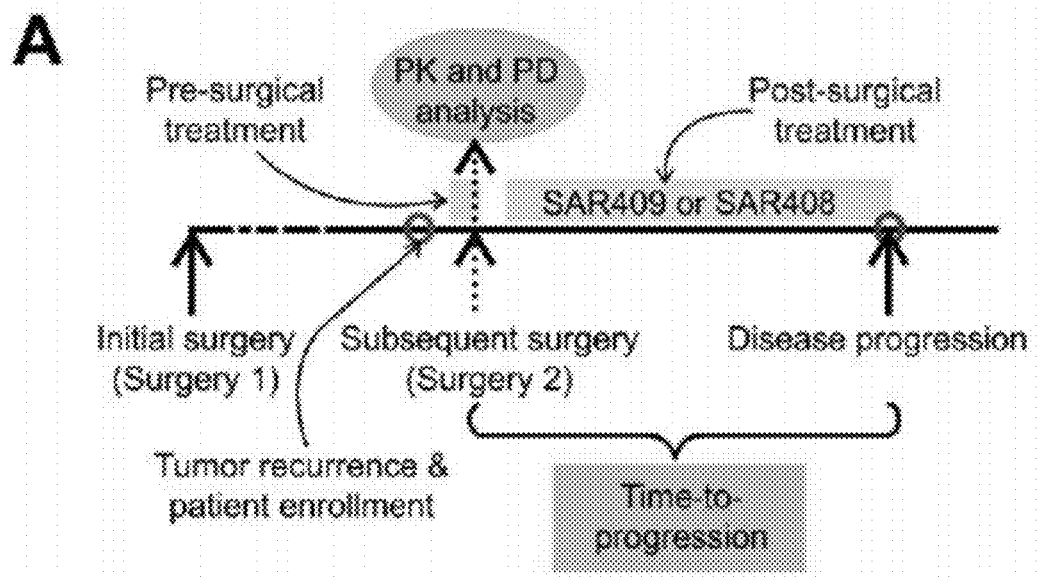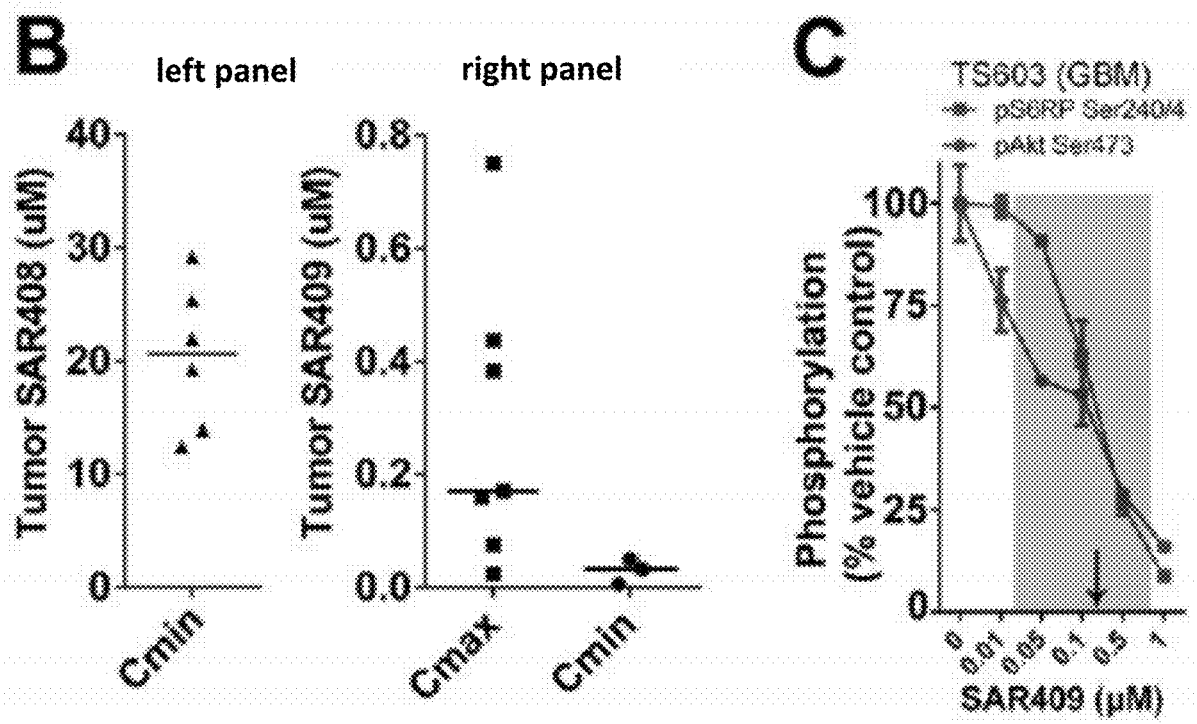
Figs. 1A – 1C

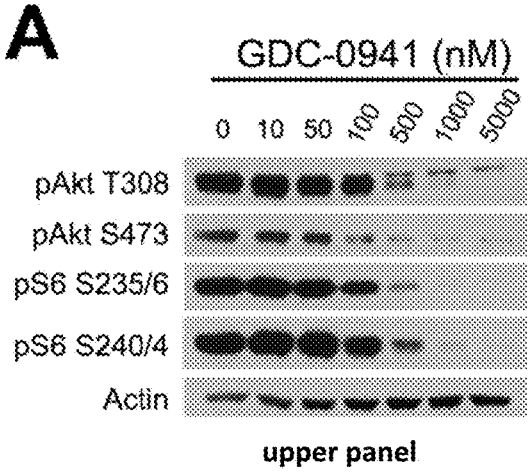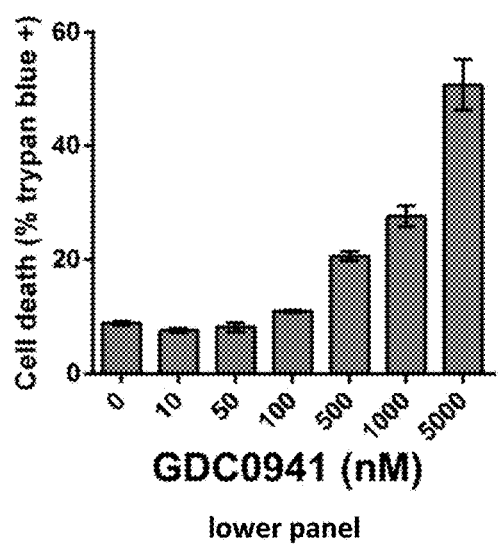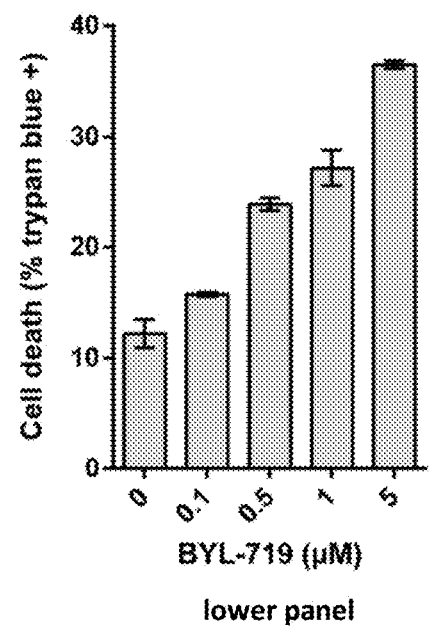
Figs. 23A – 23B

PLATELET-DERIVED GROWTH FACTOR RECEPTOR MUTATIONS AND COMPOSITIONS AND METHODS RELATING THERETO

CROSS-REFERENCE TO RELATED APPLICATIONS

This application is a U.S. National Stage entry under 35 U.S.C. § 371 of International Patent Application No. PCT/US2015/031129, filed May 15, 2015, which claims the benefit of U.S. Provisional Patent Application No. 61/994,500, filed May 16, 2014, the contents of which are here by incorporated by reference.

STATEMENT REGARDING FEDERALLY SPONSORED RESEARCH

This invention was made with government support under grant numbers NS080944, NS073831, and CA143798 awarded by the National Institutes of Health. The government has certain rights in the invention.

COPYRIGHT AND INCORPORATION BY REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

For the purposes of only those jurisdictions that permit incorporation by reference, the text of all documents cited herein is hereby incorporated by reference in its entirety.

BACKGROUND

Glioblastoma (GBM, the acronym is derived from the previous name Glioblastoma Multiforme) is the most common adult malignant brain tumor (Central Brain Tumor Registry of the United States, 2012). GBM accounts for 80% of all primary malignant brain tumors diagnosed in the United States and 30% of all brain tumors, with only meningiomas being more frequently reported. GBM has the worst prognosis of any of the malignant brain tumors tracked by the Central Brain Tumor Registry of the United States, with three year survival rates below 10%. The majority of patients survive less than one year after diagnosis.

Glioblastomas are currently treated with surgical resection when possible, depending upon the location of the tumor. Surgery is typically followed by adjuvant radiation therapy (Walker and Green, 1980) and treatment with the chemotherapeutic DNA alkylating agent temozolomide (Athanassiou et al., 2005; Stupp et al., 2005, 2009). Despite these measures, a report showed that in patients receiving adjuvant therapy the median time to progression was only 6.9 months (Stupp et al., 2005).

Because of the failure of more traditional therapies, very poor patient outcomes, and previous studies that had noted heterogeneity among glioblastomas (Liang et al., 2005; Maher et al., 2006; Mischel et al., 2003; Phillips et al., 2006), the Cancer Genome Atlas (TCGA) published a genetic analysis of a set of over 200 glioblastomas (The Cancer Genome Atlas, 2008). This analysis revealed that a few core pathways are altered in a large majority of tumors including the phosphoinositide 3-kinase (also referred to as "PI3 kinase" or "PI3K") cell signaling pathway. Similarly, TCGA analysis found that 72% of all glioblastomas have a mutation or amplification in at least one receptor tyrosine kinase (RTK). There are RTKs which are commonly altered in glioma: Epidermal Growth Factor Receptor (EGFR), MET, and Platelet Derived Growth Factor Receptor alpha (PDGFRα).

PDGFRs and their ligands have been shown to have a role in tumorigenesis in several cancers, including gliomas (Andrae et al., 2008). TCGA analysis of gliomas revealed that 16% of tumors had mutations or amplifications in PDGFRA, and 3% had amplifications in the ligand PDGFA (Cerami et al., 2012; Gao et al., 2013). The PDGFR mutations noted in the TCGA analysis are primarily in the extracellular domain of the protein.

To date there have been a number of clinical trials of EGFR or PI3K/mTOR pathway inhibitors. However, none have resulted in a durable response longer than a few weeks or a durable response in more than 5% of patients (Mellinghoff and Schultz, 2012).

Thus, there is a need for the development of better strategies for the treatment of glioma, including customized patient-specific approaches that take into account the different mutations present in the tumors of different patients.

SUMMARY OF THE INVENTION

Some of the main aspects of the present invention are summarized below. Additional aspects are provided and described in the Detailed Description, Drawings, Brief Description of the Drawings, Examples, and Claims sections of this patent application.

The present invention is based, in part, on a series of important discoveries that are described in more detail in the Examples section of this patent specification. For example, it has been discovered that certain cancer cells (including glioma cells) harboring certain mutations in the PDGFRA gene are sensitive to killing using Akt inhibitors, PI3K inhibitors, a combination of PI3 kinase inhibitors and mTOR inhibitors, or dual PI3K/mTOR inhibitors, or are significantly more sensitive to killing with such agents than are cancer cells that do not harbor such mutations—both in vitro and in vivo. Notably, in human clinical trials, treatment with a dual PI3K/mTOR inhibitor was found to significantly delay tumor progression. While a prior study reported proliferative arrest of certain glioma cells (e.g. EGFR-driven glioma cells) in vitro using a dual PI3K/mTOR inhibitor, this proliferative arrest was not accompanied by apoptosis in any of the lines tested (Fan et. al. 2006). In contrast, in the studies presented herein, it was found that in PDGFR-driven glioma cells (but not EGFR-driven glioma cells) inhibition of either (a) PI3K, (b) Akt, (c) or mTOR together with one or more of the upstream PDGFR pathway members PI3K, Akt and/or PDGFR, led to cell death.

Building on these discoveries, and other discoveries presented herein, the present invention provides a variety of new and improved methods, including, but not limited to, methods for inducing cell death in PDGFRA-mutant tumor cells, (e.g. methods comprising administering Akt inhibitors, PI3K inhibitors, combinations of PI3K inhibitors and mTOR inhibitors, or dual-acting PI3K/mTOR inhibitors), methods for identifying patients that are candidates for therapy with such agents (for example based on their PDGFRA mutation status), methods for monitoring therapeutic response to such agents in such patients (for example based on monitoring the presence of or numbers of PDGFRA mutant tumor cells), methods of treatment of such patients, methods and systems for identifying and/or testing candidate agents for use in treatment of such patients, and a variety of other methods and compositions, and combinations of such methods and compositions. For all of the methods described herein, the present invention also contemplates compositions that can be used in performing such methods and kits for performing such methods.

Accordingly, in some embodiments the present invention provides methods of killing tumor cells. For example, in one embodiment the present invention provides methods for inducing cell death in a PDGFRA-mutant tumor cell, comprising contacting a tumor cell having an oncogenic PDGFRA mutation with an effective amount of a PI3K inhibitor, thereby killing the tumor cell. In another embodiment the present invention provides methods for inducing cell death in a PDGFRA-mutant tumor cell, comprising contacting a tumor cell having an oncogenic PDGFRA mutation with an effective amount of both (a) a PI3K inhibitor and (b) an mTOR inhibitor, thereby killing the tumor cell. In another embodiment the present invention provides methods for inducing cell death in a PDGFRA-mutant tumor cell, comprising contacting a tumor cell having an oncogenic PDGFRA mutation with an effective amount of a dual PI3K/mTOR inhibitor, thereby killing the tumor cell. In another embodiment the present invention provides methods for inducing cell death in a PDGFRA-mutant tumor cell, comprising contacting a tumor cell having an oncogenic PDGFRA mutation with an effective amount of an Akt inhibitor, thereby killing the tumor cell. In another embodiment the present invention provides methods for inducing cell death in a PDGFRA-mutant tumor cell, comprising contacting a tumor cell having an oncogenic PDGFRA mutation with an effective amount of both (a) an Akt inhibitor and (b) an mTOR inhibitor, thereby killing the tumor cell. In another embodiment the present invention provides methods for inducing cell death in a PDGFRA-mutant tumor cell, comprising contacting a tumor cell having an oncogenic PDGFRA mutation with an effective amount of both (a) a PDGFR inhibitor and (b) an mTOR inhibitor, thereby killing the tumor cell.

Similarly, in some embodiments the present invention provides methods for inducing cell death in a PDGFRA-mutant tumor cell, comprising contacting a tumor cell having an oncogenic PDGFRA mutation with an effective amount of one or more of the following agents of combinations of agents: (a) a PI3K inhibitor, (b) both a PI3K inhibitor and a mTOR inhibitor, (c) a dual PI3K/mTOR inhibitor, and (c) an Akt inhibitor, (d) both an Akt inhibitor and an mTOR inhibitor, and (e) both a PDGFR inhibitor and an mTOR inhibitor, thereby killing the tumor cell.

In other embodiments the present invention provides methods of treatment. For example, in one embodiment the present invention provides methods for treating a tumor in a subject comprising: administering an effective amount of a PI3K inhibitor to a subject having a tumor that comprises tumor cells having an oncogenic PDGFRA mutation, thereby treating the tumor. In another embodiment the present invention provides methods for treating a tumor in a subject comprising: administering an effective amount of both (a) a PI3 kinase inhibitor and (b) an mTOR inhibitor to a subject having a tumor that comprises tumor cells having an oncogenic PDGFRA mutation, thereby treating the tumor. In another embodiment the present invention provides methods for treating a tumor in a subject comprising: administering an effective amount of dual PI3K/mTOR inhibitor to a subject having a tumor that comprises tumor cells having an oncogenic PDGFRA mutation, thereby treating the tumor. In another embodiment the present invention provides methods for treating a tumor in a subject comprising: administering an effective amount of an Akt inhibitor to a subject having a tumor that comprises tumor cells having an oncogenic PDGFRA mutation, thereby treating the tumor. In another embodiment the present invention provides methods for treating a tumor in a subject comprising: administering an effective amount of both (a) an Akt inhibitor and (b) an mTOR inhibitor to a subject having a tumor that comprises tumor cells having an oncogenic PDGFRA mutation, thereby treating the tumor. In another embodiment the present invention provides methods for treating a tumor in a subject comprising: administering an effective amount of both (a) a PDGFR inhibitor and (b) an mTOR inhibitor to a subject having a tumor that comprises tumor cells having an oncogenic PDGFRA mutation, thereby treating the tumor.

Similarly, in some embodiments the present invention provides methods for treating a tumor in a subject comprising: administering an effective amount of one or more of the following agents of combinations of agents to a subject having a tumor that comprises tumor cells having an oncogenic PDGFRA mutation: (a) a PI3K inhibitor, (b) both a PI3K inhibitor and a mTOR inhibitor, (c) a dual PI3K/mTOR inhibitor, and (c) an Akt inhibitor, (d) both an Akt inhibitor and an mTOR inhibitor, and (e) both a PDGFR inhibitor and an mTOR inhibitor, thereby treating the tumor.

In those embodiments that involve treatment, in some such embodiments the treatment results in one or more of the following: a decrease in the number of tumor cells, a decrease in the volume of the tumor, killing of the tumor cells, or regression of the tumor. In some embodiments the treatment methods also comprise performing surgical resection of the tumor. In such embodiments the inhibitors are administered prior to performing the surgical resection, for example for a period of 10-28 days prior to performing the surgical resection. In other such embodiments the inhibitors are administered after performing the surgical resection, for example for a period of at least 20 weeks after the surgical resection. In other such embodiments the inhibitors are administered both before and after performing the surgical resection. In some embodiments there may be no tumor recurrence for at least 6-months or at least 7-months or at least 8-months after the surgical resection. In some embodiments the treatment methods provided herein further comprise determining whether the subject has a tumor that comprises cells having an oncogenic PDGFRA mutation, or how many of tumor cells are present. In some embodiments such determining step is carried out prior to commencing administration of the inhibitors—for example to determine if the subject is a candidate for therapy. In some embodiments the determining step is carried out after administration of the inhibitors has commenced—for example to monitor the efficacy of the therapy.

In addition to some of the specific treatment methods described herein, the present invention also contemplates treatment of subjects using other treatment regimens known to be useful in the treatment of tumors in general, or PDGFR-driven tumors in particular, or gliomas in particular, including, but not limited to, surgical methods (e.g. tumor resection surgery), radiation therapy, chemotherapy (for example using temozolomide), or anti-angiogenic therapy (for example using bevacizumab).

In each of the embodiments described in the present patent specification that involve killing of tumor cells (or inducing cell death), such killing or cell death may be, or may include, apoptosis. In addition to resulting in cell killing/cell death, each of the embodiments listed in the present patent specification (such as those listed above) may also result in, and/or provide methods for, inhibiting cell proliferation.

In each of the embodiments in this patent specification that involve PDGFRA mutant tumor cells, in some such embodiments the tumor cells do not comprise one or more of the following: (a) an oncogenic EGFR mutation, (b) an oncogenic PTEN mutation, (c) an oncogenic PI3K mutation, (d) an oncogenic PI3KR1 mutation, (e) an oncogenic MET mutation, (f) an oncogenic NF1 mutation, and (g) an oncogenic FGFR mutation. For example, in several embodiments the tumor cells do not comprise an oncogenic EGFR mutation.

In some of the embodiments described herein that refer to an oncogenic PDGFRA mutation, that mutation may be one that results in one or more of the following: constitutive activation of a PDGRFA receptor molecule, constitutive PDGRFA phosphorylation, constitutive AKT activation, overexpression of a PDGRFA receptor molecule, or increased activity of a PDGRFA receptor molecule. For example, in some embodiments the oncogenic PDGFRA mutation may comprise a PDGFRA gene amplification, such as a focal amplification of the human PDGFRA locus on human chromosome 4q12. In some embodiments the oncogenic PDGFRA mutation may be a mutation in the extracellular domain of PDGRFA, such as within the third IG-like domain or within the region spanning amino acids 202-306 of human PDGRFA. In some embodiments the oncogenic PDGFRA mutation may be a G228V missense mutation, or a P250S mutation, or a D842V mutation. In some embodiments the oncogenic PDGFRA mutation comprises a deletion of a portion of the PDGFRA extracellular domain.

In some of the embodiments described herein that involve a PI3K inhibitor, the PI3K inhibitor may be an inhibitor of a Class I PI3K, such as a p110α class I PI3K. In some such embodiments the PI3K inhibitor may be selected from the group consisting of SAR245409, SAR245408, BYL-719, GDC-0980, GDC-0941, wortmannin, Ly294002, demethoxyviridin, perifosine, delalisib, idelaisib, PX-866, IPI-145, BAY 80-6946, BEZ235, RP6530, TGR 1202, RP5264, SF1126, INK1117, BKM120, Palomid 529, GSK1059615, ZSTK474, PWT33597, IC87114, TG100-115, CAL263, RP6503, PI-103, GNE-477, CUDC-907, AEZS-136, and analogues, variants, and derivatives thereof. In other such embodiments any other suitable PI3K inhibitor known in the art may be used.

In some of the embodiments described herein that involve a PI3K inhibitor, the PI3K inhibitor may be a dual PI3-kinase/mTOR inhibitor selected from the group consisting of SAR245409, PWT33597, PI-103, GNE-477, NVP-BEZ235, BGT226, SF1126, PKI-587, XL765, PF-04691502, PF-05212384, LY3023414 and analogues, variants, and derivatives thereof. In other embodiments any other suitable dual PI3-kinase/mTOR inhibitor known in the art may be used.

In some of the embodiments described herein that involve an mTOR inhibitor, the mTOR inhibitor may be selected from the group consisting of SAR245409, PWT33597, PI-103, GNE-477, NVP-BEZ235, BGT226, SF1126, PKI-587, XL765, PF-04691502, PF-05212384, LY3023414 and analogues, variants, and derivatives thereof. In other embodiments any other suitable mTOR inhibitor known in the art may be used.

In some of the embodiments described herein that involve an Akt inhibitor, the Akt inhibitor may be selected from the group consisting of MK-2206, perifosine, GSK690693, ipatasertib (GDC-0068), AZD5365, afuresertib (GSK2110183), At13148, PF-04691502, AT7867, triciribine, CCT128930, A-674563, PHT0427, miltefosine, honokiol, TIC10, and analogues, variants, and derivatives thereof. In other embodiments any other suitable Akt inhibitor known in the art may be used.

A variety of living subjects may be treated or diagnosed with the methods and compositions of the present invention. In some embodiments the subject is a mammal, for example a rodent (e.g. a mouse), a dog, a non-human primate, or a human. In some embodiments the subjects may have cancer, such as a PDGRF-driven cancer. In some embodiments the subject may have a cancer selected from the group consisting of glioma, melanoma, lung cancer, non-small cell lung cancer (NSCLC), breast cancer and gastrointestinal stromal tumor (GIST). In some embodiments the subject has glioblastoma, such as recurrent glioblastoma. In some such embodiments the glioblastoma has recurred following treatment using chemotherapy, radiation therapy, or surgical resection, or any combination thereof. Similarly, in those embodiments described herein that involve tumors or tumor cells, the tumors or tumor cells may be those of a PDGRF-driven tumor. For example, in some such embodiments the tumor or tumor cell may be, or may be from or within, a tumor selected from the group consisting of glioma, melanoma, lung cancer, non-small cell lung cancer (NSCLC), breast cancer and gastrointestinal stromal tumor (GIST). In some such embodiments the tumor or tumor cells may be, or may be from or within, a glioblastoma, such as recurrent glioblastoma. In some such embodiments the glioblastoma may be one that has recurred following treatment using chemotherapy, radiation therapy, or surgical resection, or any combination thereof.

In some embodiments the present invention provides various methods of determining whether a subject is a candidate for treatment using the methods or compositions described herein, as well as compositions and kits that can be used in performing such diagnostic methods. Similarly, in some embodiments the present invention provides various methods for monitoring the progression of disease and/or the efficacy of a treatment. All of such methods generally comprise determining whether a sample contains cells having an oncogenic PDGFRA mutation, or how many of such cells are present, or how the number of such cells is changing over time. In some embodiments, if the sample does contain such an oncogenic PDGFRA mutation, the subject may be a candidate for treatment using the methods and compositions provided herein. In some embodiments, if the number of such cells is decreasing over time, the subject's disease may be regressing and/or the treatment may be effective. Conversely, if the number of such cells is increasing over time, the subject's disease may be progressing and/or the treatment may be in effective or require adjustment (e.g. adjustment of dosages or supplementation with other agents or other treatment methodologies, etc.).

For example, in some embodiments the present invention provides a method of determining whether a subject is a candidate for treatment with the methods and compositions described herein, wherein the method comprises determining whether a nucleic acid from the subject comprises an oncogenic PDGFRA mutation, wherein if the nucleic acid comprises the oncogenic PDGFRA mutation the subject may be a candidate for treatment. In some such embodiments the method also comprises performing an assay on a sample (e.g. tumor sample) obtained from the subject, wherein the sample comprises a PDGFRA nucleic acid sequence. In some such embodiments the method may also comprise a step of obtaining a sample (e.g. tumor sample) from the subject, wherein the sample comprises a PDGFRA nucleic acid sequence. In some embodiments such methods may comprise a step of contacting the sample with a primer or probe, such as a sequencing primer and/or a primer or probe capable of binding to or hybridizing with a PDGFRA nucleic acid sequence. In some such embodiments the primer or probe binds to, or hybridizes with, the nucleic acid sequence to form a complex, and the assay involves determining whether the PDGFRA nucleic acid sequence in the complex comprises the oncogenic PDGFRA mutation. Such methods may comprise a subsequent step of treating the subject using one of the treatment methods provided herein.

In other embodiments the present invention provides a method of monitoring the progress of disease in a subject or monitoring the efficacy of a treatment in a subject, wherein the method comprises determining the number of cells comprising an oncogenic PDGFRA mutation that are present in a sample from the subject, or in a tumor of the subject, at a first time point and second (later) time point, wherein if the number of cells increases from the first to the second time point, the subject's disease may be progressing, or (if the subject is being treated) the subject's treatment may not be effective or may require adjustment, and wherein if the number of cells decreases from the first to the second time point, the subject's disease may be regressing or (if the subject is being treated) the subject's treatment may be effective.

In other embodiments the present invention provides kits for use in performing methods as described above (and elsewhere herein). For example, in one such embodiment the kit comprises one or more reagents selected from the group consisting of (a) positive-control comprising a nucleic acid molecule, wherein the nucleic acid molecule comprises an oncogenic PDGFRA mutation, (b) a negative-control comprising a nucleic acid molecule, wherein the nucleic acid molecule does not comprise the oncogenic PDGFRA mutation present in the positive-control, (c) a sequencing primer, and (d) a primer or probe capable of binding to or hybridizing with a PDGFRA nucleic acid sequence.

In other embodiments the present invention provides in vitro and in vivo model systems for identifying, or testing the activity of candidate molecules that may be useful in the treatment of PDGFR-driven tumors. For example, in some embodiments such model systems comprise cells that either (a) comprise an oncogenic PDGFRA mutation, or (b) overexpress the PDGFR ligand PDGF-B. In some such model systems the cells are glioma or glioblastoma cells, such as TS543 or S5472 cells. In some such model systems the cells are non-small cell lung cancer cells, such as H1703 human non-small cell lung cancer cells. In some embodiments the models are in vivo mouse models, for example mouse models wherein the mouse comprises TS543 glioblastoma cells, S5472 glioma cells or H1703 non-small cell lung cancer cells. In some such embodiments the model system is an in vivo orthotopic glioma model, such as a model in which the mouse comprises glioma cells that overexpress PDGF-B. Such methods may be made using intracranial injection of a virus comprising a PDGF-B sequence operatively linked to a suitable promoter.

In other embodiments the present invention provides methods for identifying candidate molecules that may be useful in the treatment of PDGFR-driven tumors. For example, in some embodiments the present invention provides a method for identifying a molecule having anti-tumor activity, wherein the method comprises (a) contacting test cells that comprise an oncogenic PDGFRA mutation with a candidate molecule, (b) contacting control cells that do not comprise the oncogenic PDGFRA mutation with the candidate molecule, and comparing the effect of the candidate molecule on the test cells and the control cells, wherein if the candidate molecule causes more cell death in the test cells as compared to the control cells, the candidate molecule could be useful as an anti-tumor agent. Several variations on such a screening method are envisioned and are within the scope of the present invention.

In other embodiments the present invention provides compositions, such as pharmaceutical compositions, for use in the methods provided by the present invention. In some embodiments such a composition comprises an Akt inhibitor, a PI3K inhibitor, a PI3K inhibitor and an mTOR inhibitor, or a dual PI3K/mTOR inhibitor. In yet other embodiments the present invention provides compositions for use in determining whether a subject is a candidate for treatment using the methods described herein, or for monitoring the efficacy of such treatment, the composition comprising a primer or probe capable of hybridizing to a PDGFRA nucleic acid sequence.

These and other embodiments are described elsewhere in this patent application, including in the Drawings, Brief Description of the Drawings, Detailed Description, Examples, and Claims sections of this application. Furthermore, it should be understood that variations and combinations of each of the embodiments described herein are contemplated and are intended to fall within the scope of the present invention.

BRIEF DESCRIPTION OF THE DRAWINGS

FIGS. 1A-1E: SAR408 and SAR409 inhibit PI3K/mTOR in GBM tumor samples. (A) Clinical trial design. See Examples for details. (B) Tumor concentrations of SAR408 (left panel) and SAR409 (right panel). Each data point represents one patient. The horizontal bar indicates the median drug concentration. Samples were taken at trough ($C_{min}$) for the SAR408 200 mg QD and SAR409 50 mg BID patient cohorts. Samples from patients on the SAR409 90 mg QD cohort were taken around the plasma tmax (~3 h post-dosing) ($C_{max}$). (C) Phosphorylation (mean±SEM) of Akt (Ser473) and S6RP (Ser240/4) in TS603 GBM tumor spheres treated for four hours with SAR409. $C_{max}$ concentrations of SAR409 (see FIG. 1B) are highlighted as a shaded box (range) and arrow (median). (D) Cartoon of PI3K/mTOR pathway. Pathway members PRAS40, S6K1, S6RP and 4E-BP1 were included in the IHC-based quantification. (E) PI3K pathway activity (upper panel) and tumor cell proliferation (lower panel) in matched Surgery 1/Surgery 2 biopsy pairs. The Spearman correlation coefficient between the number of markers with reduction versus Ki-67 is 0.65, with p-value 0.0026.

FIGS. 23A-23B: PI3K inhibition induces cell death in a PDGFR driven glioma line. (A) TS543 cells were treated with pan-Class I PI3K inhibitor GDC-0941 for four hours, then lysed and blotted with indicated antibodies (upper panel). Cells were treated with GDC-0941 for five days, then analyzed for induction of cell death (lower panel). (B) TS543 cells were treated with p110α specific inhibitor BYL-719 for four hours, then lysed and blotted with indicated antibodies (upper panel). Cells were treated with BYL-719 for five days, then analyzed for induction of cell death (lower panel). All graphs depict mean±SEM.

DETAILED DESCRIPTION

Figure 1D:
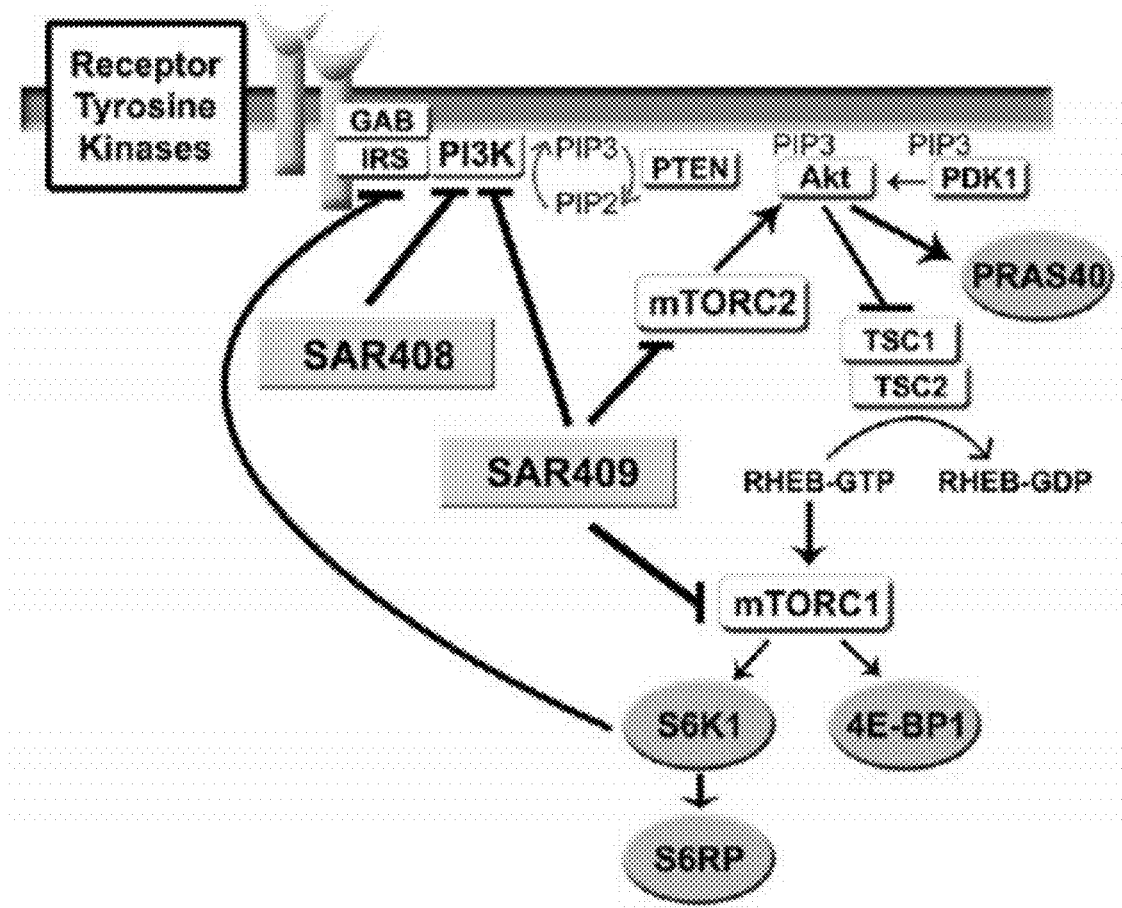

Some of the main embodiments of the present invention are described in the above Summary of the Invention section of this patent application, as well as in the Figures, Brief Description or the Figures, Examples, and Claims sections of this application. This Detailed Description section provides certain additional description relating to the compositions and methods of the present invention, and is intended to be read in conjunction with all other sections of the present patent application. As used herein, the terms "about" and "approximately," when used in relation to numerical values, mean within + or −20% of the stated value. Other terms are defined elsewhere in this patent specification, or else are used in accordance with their usual meaning in the art.

Pi3K Inhibitors.

Several embodiments of the present invention involve PI3K inhibitors. In some of such embodiments, any suitable PI3K inhibitor can be used. In some embodiments the suitability of a PI3K inhibitor for use in accordance with the methods of the present invention may be ascertained from the literature (for example from published studies demonstrating anti-PI3K activity), or may be ascertained by employing various assays for PI3K activity known in the art, or may be ascertained by employing one of the assays described in the Examples section of the present patent application to demonstrate cell killing, anti-tumor activity, and the like. Several PI3K inhibitors that are known in the art can be used in conjunction with the present invention, including but not limited to, inhibitors of class I PI3Ks or inhibitors of p110α class I PI3Ks. For example, in some embodiments, any one or more of the following PI3K inhibitors (or classes of inhibitors) may be used: SAR245409 (voxtalisib, XL765), SAR245408 (pilaralisib, XL147), BYL-719, GDC-0980, GDC-0941, wortmannin, Ly294002, demethoxyviridin, perifosine, delalisib, PX-866, IPI-145, BAY 80-6946, BEZ235, RP6530, TGR1202, RP5264, SF1126, INK1117, BKM120 (NVP-BKM120, buparlisib), idelaisib, Palomid 529, GSK1059615, ZSTK474, PWT33597, IC87114, TG100-115, CAL263, RP6503, PI-103, GNE-477, CUDC-907, and AEZS-136. In some embodiments, any suitable variant, analogue or derivative of any one of such PI3K inhibitors may be used. In some embodiments the PI3K inhibitor may be a small molecule, or an antibody, or any other suitable agent that has PI3K inhibitory activity. In some embodiments the PI3K inhibitor used is one that can permeate the blood brain barrier. In some embodiments the PI3K inhibitor may be linked to, or capable of co-delivery with, another agent that can confer upon the PI3K inhibitor the ability to permeate the blood-brain barrier. In some embodiments, the PI3K inhibitor used is SAR245408, or an analogue, variant, or derivative thereof. In some embodiments, the PI3K inhibitor used is SAR245409, or an analogue, variant, or derivative thereof.

mTOR Inhibitors.

Several embodiments of the present invention involve mTOR inhibitors. In some of such embodiments, any suitable mTOR inhibitor can be used. In some embodiments the suitability of a mTOR inhibitor for use in accordance with the methods of the present invention may be ascertained from the literature (for example from published studies demonstrating anti-mTOR activity), or may be ascertained by employing various assays for mTOR activity known in the art, or may be ascertained by employing one of the assays described in the Examples section of the present patent application to demonstrate cell killing and/or anti-tumor activity, and the like. Several mTOR inhibitors that are known in the art can be used in conjunction with the present invention. For example, in some embodiments, any one or more of the following mTOR inhibitors (or classes of inhibitors) may be used: SAR245409, GDC-0980, CCI-779, KU-0063794, rapamycin, epigallocatechin gallate (EGCG), caffeine, curcumin, resveratrol, sirolimus, temsirolimus, everolimus, and ridaforolimus. In some embodiments, any suitable variant, analogue or derivative of any one of such mTOR inhibitors may be used. In some embodiments the mTOR inhibitor may be a small molecule, or an antibody, or any other suitable agent that has mTOR inhibitory activity. In some embodiments the mTOR inhibitor used is one that can permeate the blood brain barrier. In some embodiments the mTOR inhibitor may be linked to, or capable of co-delivery with, another agent that can confer upon the mTOR inhibitor the ability to permeate the blood-brain barrier.

Dual PI3K/mTOR Inhibitors.

Several embodiments of the present invention involve dual PI3K/mTOR inhibitors. In some of such embodiments, any suitable dual PI3K/mTOR inhibitor can be used. In some embodiments the suitability of a dual PI3K/mTOR inhibitor for use in accordance with the methods of the present invention may be ascertained from the literature (for example from published studies demonstrating anti-PI3K and anti-mTOR activity), or may be ascertained by employing various assays for mTOR activity and PI3K activity known in the art, or may be ascertained by employing one of the assays described in the Examples section of the present patent application. Several dual PI3K/mTOR inhibitors that are known in the art can be used in conjunction with the present invention. For example, in some embodiments, any one or more of the following dual PI3K/mTOR inhibitors may be used: SAR245409, PWT33597, PI-103, GNE-477, NVP-BEZ235, BGT226, SF1126, PKI-587, XL765, PF-04691502, PF-05212384, and LY3023414. In some embodiments, any suitable variant, analogue or derivative of any one of such dual PI3K/mTOR inhibitors may be used. In some embodiments the dual PI3K/mTOR inhibitor may be a small molecule, or an antibody, or any other suitable agent that has PI3K inhibitory activity and mTOR inhibitory activity. In some embodiments the dual PI3K/mTOR inhibitor used is one that can permeate the blood brain barrier. In some embodiments the dual PI3K/mTOR inhibitor may be linked to, or capable of co-delivery with, another agent that can confer upon the dual PI3K/mTOR inhibitor the ability to permeate the blood-brain barrier. In some embodiments, the dual PI3K/mTOR inhibitor used is SAR245409, or an analogue, variant, or derivative thereof.

Akt Inhibitors.

Several embodiments of the present invention involve Akt inhibitors. In some of such embodiments, any suitable Akt inhibitor can be used. In some embodiments the suitability of an Akt inhibitor for use in accordance with the methods of the present invention may be ascertained from the literature (for example from published studies demonstrating anti-Akt activity), or may be ascertained by employing various assays for Akt activity known in the art, or may be ascertained by employing one of the assays described in the Examples section of the present patent application. Several Akt inhibitors that are known in the art can be used in conjunction with the present invention. For example, in some embodiments, any one or more of the following Akt inhibitors (or classes of inhibitors) may be used: MK-2206, perifosine, GSK690693, ipatasertib (GDC-0068), AZD5365, afuresertib (GSK2110183), At13148, PF-04691502, AT7867, triciribine, CCT128930, A-674563, PHT0427, miltefosine, honokiol, and TIC10. In some embodiments, any suitable variant, analogue or derivative of any one of such Akt inhibitors may be used. In some embodiments the Akt inhibitor may be a small molecule, or an antibody, or any other suitable agent that has Akt inhibitory activity. In some embodiments the Akt inhibitor used is one that can permeate the blood brain barrier. In some embodiments the Akt inhibitor may be linked to, or capable of co-delivery with, another agent that can confer upon the Akt inhibitor the ability to permeate the blood-brain barrier. In some embodiments, the Akt inhibitor used is MK-2206, or an analogue, variant, or derivative thereof.

Methods of Treatment.

In certain embodiments the present invention provides methods of treatment. As used herein, the terms "treat," "treating," and "treatment" encompass a variety of activities aimed at achieving a detectable improvement in one or more clinical indicators or symptoms associated with a tumor (such as a glioma, e.g. a glioblastoma, or a PDFGR-driven tumor). For example, such terms include, but are not limited to, reducing the rate of growth of a tumor (or of tumor cells), halting the growth of a tumor (or of tumor cells), causing regression of a tumor (or of tumor cells), reducing the size of a tumor (for example as measured in terms of tumor volume or tumor mass), reducing the grade of a tumor, eliminating a tumor (or tumor cells), preventing, delaying, or slowing recurrence (rebound) of a tumor, improving symptoms associated with tumor, improving survival from a tumor, inhibiting or reducing spreading of a tumor (e.g. metastases), and the like.

The term "tumor" is used herein in accordance with its normal usage in the art and includes a variety of different tumor types, including, but not limited to gliomas, glioblastoma multiforme (GBM), astrocytomas, oligodendrogliomas, and the various other tumor types mentioned in the present patent specification.

In carrying out the treatment methods described herein, any suitable method or route of administration can be used to deliver the active agents (e.g. the P13K inhibitors, mTOR inhibitors, Akt inhibitors and/or dual PI3K/mTOR inhibitors). In some embodiments systemic administration may be employed, for example, oral or intravenous administration, or any other suitable method or route of systemic administration known in the art. In some embodiments (including, but not limited to, those in which one or more of the agents used is not able to permeate the blood-brain barrier), intracranial (e.g. intracerebral) delivery may be employed. For example, pressure-driven infusion through an intracranial catheter, also known as convection-enhanced delivery (CED) may be used.

As used herein the terms "effective amount" or "therapeutically effective amount" refer to an amount of an active agent (e.g. a P13K inhibitor, mTOR inhibitor, Akt inhibitor and/or dual PI3K/mTOR inhibitors) as described herein that is sufficient to achieve, or contribute towards achieving, one or more desirable clinical outcomes, such as those described in the "treatment" description above. An appropriate "effective" amount in any individual case may be determined using standard techniques known in the art, such as dose escalation studies, and may be determined taking into account such factors as the desired route of administration (e.g. systemic vs. intracranial), desired frequency of dosing, etc. Furthermore, an "effective amount" may be determined in the context of any co-administration method to be used. For example, rather than perform dosing studies using an PI3K inhibitor alone, or a mTOR inhibitor alone, dosing studies may be performed using both a PI3K inhibitor and an mTOR inhibitor, because, as described herein, the effects of such agents may be synergistic. One of skill in the art can readily perform such dosing studies (whether using single agents or combinations of agents) to determine appropriate doses to use, for example using assays such as those described in the Examples section of this patent application—which involve administration of a PI3K inhibitor or a dual PI3K/mTOR inhibitor to humans.

For example, in some embodiments the dose of an active agent of the invention may be calculated based on studies in humans or other mammals carried out to determine efficacy and/or effective amounts of the active agent. The dose amount and frequency or timing of administration may be determined by methods known in the art and may depend on factors such as pharmaceutical form of the active agent, route of administration, whether only one active agent is used or multiple active agents (for example, the dosage of a first active agent required may be lower when such agent is used in combination with a second active agent), and patient characteristics including age, body weight or the presence of any medical conditions affecting drug metabolism.

In one embodiment of the invention, the dose of an active agent as described herein (such as, for example, a PI3K inhibitor, an Akt inhibitor, a mTOR inhibitor, and/or a dual PI3K/mTOR inhibitor) is at least 1 mg, at least 5 mg, at least 10 mg, at least 20 mg, at least 30 mg, at least 40 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, at least 850 mg, at least 900 mg, at least 950 mg or at least 1000 mg. In some such embodiments the above dosages are mg/kg. In some such embodiments the above dosages are mg/kg/day. In some embodiments the dose of active agent is in the range of 1 to 1000 mg, 1 to 750 mg, 1 to 500 mg, 1 to 250 mg, 1 to 100 mg, 1 to 50 mg, 1 to 25 mg, 25 to 1000 mg, 25 to 500 mg, 25 to 100 mg, 25 to 50 mg, 50 to 1000 mg, 50 to 500 mg, 50 to 100 mg. In some embodiments the above dosages are mg/kg/day. In some embodiments of the invention the dose of active agent is at least 0.1 mg/kg, at least 0.5 mg/kg, at least 1 mg/kg, at least 5 mg/kg, at least 10 mg/kg, at least 20 mg/kg, at least 30 mg/kg, at least 40 mg/kg, at least 50 mg/kg, at least 75 mg/kg, at least 100 mg/kg, at least 125 mg/kg, at least 150 mg/kg, at least 175 mg/kg, at least 200 mg/kg, at least 225 mg/kg, at least 250 mg/kg, at least 275 mg/kg, at least 300 mg/kg, at least 325 mg/kg, at least 350 mg/kg, at least 375 mg/kg, at least 400 mg/kg, at least 425 mg/kg, at least 450 mg/kg, at least 475 mg/kg, at least 500 mg/kg, at least 550 mg/kg, at least 600 mg/kg, at least 650 mg/kg, at least 700 mg/kg, at least 750 mg/kg, at least 800 mg/kg, at least 850 mg/kg, at least 900 mg/kg, at least 950 mg/kg or at least 1000 mg/kg. In some such embodiments the above dosages are mg/kg/day. In another embodiment, the dose of active agent is in the range of 1 to 1000 mg/kg, 1 to 750 mg/kg, 1 to 500 mg/kg, 1 to 250 mg/kg, 1 to 100 mg/kg, 1 to 50 mg/kg, 1 to 25 mg/kg, 25 to 1000 mg/kg, 25 to 500 mg/kg, 25 to 100 mg/kg, 25 to 50 mg/kg, 50 to 1000 mg/kg, 50 to 500 mg/kg, or 50 to 100 mg/kg. In some embodiments the above dosages are mg/kg/day. In some embodiments a single dose may be administered. In some embodiments multiple doses may be administered over a period of time, for example, at specified intervals, such as, four times per day, twice per day, once a day, weekly, monthly, and the like. In some embodiments the dose of SAR409 is about 90 mg administered once a day or about 50 mg administered twice a day. In some embodiments the dose of SAR408 is about 200 mg administered once a day.

In certain embodiments the methods of treatment provided herein may be employed together with other treatment methods, including, but not limited to, surgical methods (e.g. for tumor resection), radiation therapy methods, treatment with chemotherapeutic agents (e.g. temozolomide, carmustine (BCNU), or cisplatin), treatment with antiangiogenic agents (e.g. bevacizumab), or treatment with tyrosine kinase inhibitors (such as gefitinib or erlotinib). Similarly, in certain embodiments the methods of treatment provided herein may be employed together with procedures used to monitor disease status/progression, such as biopsy methods and diagnostic methods (e.g. MRI methods or other imaging methods).

For example, in some embodiments the PI3K inhibitor and mTOR inhibitor, or the dual PI3K/mTOR inhibitor, or the Akt inhibitor, may be administered to a subject prior to performing surgical resection of a tumor. In such embodiments the PI3K inhibitor and mTOR inhibitor, or the dual PI3K/mTOR inhibitor, or the Akt inhibitor, are administered for a period of 10-28 days prior to performing surgical resection. In other such embodiments the PI3K inhibitor and mTOR inhibitor, or the dual PI3K/mTOR inhibitor, or the Akt inhibitor, are administered for a period of about 5, about 10, about 15, about 20, about 25, about 30, about 35, about 40, about 45, or about 50 days prior to performing surgical resection. In other such embodiments the PI3K inhibitor and mTOR inhibitor, or the dual PI3K/mTOR inhibitor, or the Akt inhibitor, are administered for a period of less than 60 days, less than 50 days, less than 40 days, less than 30 days, less than 25 days, less than 20 days, less than 15 days, or less than 10 days prior to performing surgical resection.

In other such embodiments the PI3K inhibitor and mTOR inhibitor, or the dual PI3K/mTOR inhibitor, or the Akt inhibitor, are administered for a period of at least 5 days, at least 10 days, at least 15 days, at least 20 days, at least 25 days, at least 30 days, or at least 40 days prior to performing surgical resection. In other such embodiments the PI3K inhibitor and mTOR inhibitor, or the dual PI3K/mTOR inhibitor, or the Akt inhibitor, are administered for a period of about 5-50 days, about 5-40 days, about 5-30 days, or about 5-20 days, or about 5-10 days prior to performing surgical resection. In other embodiments the PI3K inhibitor and mTOR inhibitor, or the dual PI3K/mTOR inhibitor, or the Akt inhibitor, are administered after performing surgical resection. In other such embodiments the PI3K inhibitor and mTOR inhibitor, or the dual PI3K/mTOR inhibitor, or the Akt inhibitor, are administered for a period of at least 1 week, at least 5 weeks, at least 10 weeks, at least 15 weeks, at least 20 weeks, at least 25 weeks, at least 30 weeks, at least 35 weeks, at least 40 weeks, at least 50 weeks, or at least 60 weeks after the surgical resection. In other such embodiments the PI3K inhibitor and mTOR inhibitor, or the dual PI3K/mTOR inhibitor, or the Akt inhibitor, are administered for a period of at least 15-20 weeks, 15-30 weeks, 15-40 weeks, 15-50 weeks, or 15-60 weeks after the surgical resection. In other such embodiments the PI3K inhibitor and mTOR inhibitor, or the dual PI3K/mTOR inhibitor, or the Akt inhibitor, are administered for a period of at least 20-35 weeks after the surgical resection.

In other embodiments the PI3K inhibitor and mTOR inhibitor, or the dual PI3K/mTOR inhibitor, or the Akt inhibitor, are administered both before and after performing surgical resection of a tumor. In other embodiments the subject has no tumor recurrence after the surgical resection. In other embodiments the subject has no tumor recurrence for at least 1 month, at least 2 months, at least 3 months, at least 4 months, at least 5 months, at least 6 months, at least 7 months, at least 8 months, at least 9 months, at least 10 months, at least 11 months, at least 1 year, or at least 2 years after the surgical resection.

Subjects.

As used herein the term "subject" encompasses mammals, including, but not limited to, humans, non-human primates, dogs, rodents (such as rats, mice and guinea pigs), and the like. In some embodiments of the invention the subject is a human.

In some embodiments the subject has cancer, for example, a PDGFR-driven cancer. In some embodiments the subject has a cancer selected from the group consisting of glioma, melanoma, lung cancer, non-small cell lung cancer (NSCLC), breast cancer and gastrointestinal stromal tumor (GIST). In some embodiments the glioma is a glioblastoma, for example, recurrent glioblastoma. In some such embodiments the glioblastoma has recurred following treatment using chemotherapy, radiation therapy, or surgical resection, or any combination thereof.

PDGFRA Mutations.

In each of the embodiments described herein that involve oncogenic PDGFRA mutations, the oncogenic PDGFRA mutation in a subject or a cell may be one that results in one or more of the following: constitutive activation of a PDGRFA receptor molecule, constitutive PDGRFA phosphorylation, constitutive AKT activation, overexpression of a PDGRFA receptor molecule, or increased activity of a PDGRFA receptor molecule. For example, in some embodiments the oncogenic PDGFRA mutation may comprise a PDGFRA gene amplification, such as a focal amplification of the human PDGFRA locus on human chromosome 4q12. In some embodiments the oncogenic PDGFRA mutation may be a mutation in the extracellular domain of PDGRFA, such as within the third IG-like domain or within the region spanning amino acids 202-306 of human PDGRFA. In some embodiments the oncogenic PDGFRA mutation may be a G228V missense mutation, or a D842V mutation. In some embodiments the oncogenic PDGFRA mutation comprises a deletion of a portion of the PDGFRA extracellular domain.

Compositions and Methods for Detection of PDGFRA Mutations.

In each of the embodiments described herein that involve a PDGFRA primer or probe, the primer or probe may be one that is capable of binding to, or hybridizing with, a PDGFRA nucleic acid comprising an oncogenic PDGFRA mutation. In some embodiments the primer or probe may be one that binds to or hybridizes with a PDGFRA nucleic acid that comprises the oncogenic PDGFRA mutation, but that does not bind to or hybridize with a PDGFRA nucleic acid that does not comprise the oncogenic PDGFRA mutation. In some embodiments the primer or probe may be one that binds to, or hybridizes with, a PDGFRA nucleic acid comprising an oncogenic PDGFRA mutation with a higher affinity than that with which it binds to, or hybridizes with, a PDGFRA nucleic acid that does not comprise that oncogenic PDGFRA mutation. In each of the embodiments described herein that relate to primers and probes, the primer or probe may be contacted with the sample, or with the PDGFRA nucleic acid sequence within the sample, under conditions such that the primer or probe will bind to or hybridize with the PDGFRA nucleic acid sequence. Such conditions are well known in the art and/or can readily be determined by one of ordinary skill in the art without undue experimentation. In some embodiments, the primer or probe is specifically designed to distinguish between nucleic acids that comprise an oncogenic PDGFRA mutation and nucleic acids that do not comprise that oncogenic PDGFRA mutation. In some embodiments the primer or probe is specifically designed to distinguish between nucleic acids that comprise a single copy of a PDGRFA sequence and those that comprise an amplification of a PDGFRA sequence. In some embodiments the probe is a fluorescent in situ hybridization (FISH) probe, such as a fluorescent in situ hybridization (FISH) probe for human chromosome 4 (CFP4). In some embodiments multiple primers or probes may be used. For example, in one embodiment at least two fluorescent in situ hybridization (FISH) probes are used, including a FISH probe for human chromosome 4 (CFP4) and a FISH probe for PDGFRA.

In some of the embodiments described herein, an "assay" step or a "determining" step (e.g. for determining the presence of a PDGFRA mutation) may be performed using any suitable method known in the art. In one embodiment fluorescent in situ hybridization (FISH) may be used, such as quantitative fluorescent in situ hybridization (FISH). Similarly, the "assay" step or the "determining" step may comprise performing PCR (such as quantitative PCR), nucleic acid sequencing, comparative genomic hybridization (CGH), or any other suitable method known in the art. For example, in one embodiment the "assay" step or the "determining" step may comprise performing comparative genomic hybridization to analyze variations in copy number of the PDGFRA gene between the sample and a control known to have no PDGFRA amplifications. Such CGH methods may comprise using a human probe array (such as the 1 million probe Agilent array) and/or using a PDGFRA probe.

Compositions.

In certain embodiments, the present invention provides pharmaceutical compositions. The term "pharmaceutical composition," as used herein, refers to a composition comprising at least one active agent as described herein (such as, for example, a PI3K inhibitor, an Akt inhibitor, a mTOR inhibitor, and/or a dual PI3K/mTOR inhibitor), and one or more other components useful in formulating a composition for delivery to a subject, such as diluents, buffers, carriers, stabilizers, dispersing agents, suspending agents, thickening agents, excipients, preservatives, and the like.

EXAMPLES

The invention is further described in the following non-limiting Examples.

Example 1

Clinical Trial

A clinical trial of a PI3K inhibitor and a dual PI3K/mTOR inhibitor in glioma patients was performed. The trial was designed to allow examination of potential clinical and biological effects of drug treatment, changes in cell proliferation, changes in time to progression (TIP) and also to measure concentrations of drug in patient plasma and tumors, to determine the genotype of the tumors, and assess pharmacodynamic inhibition of the drug targets in the tumor itself.

Trial Objectives and Summary.

The open-label, nonrandomized study "Exploratory Pharmacodynamic Study of SAR409 (XL765) or SAR408 (XL147) Administered as Single Agents in Subjects With Recurrent Glioblastoma Who Are Candidates for Surgical Resection" was registered with www.ClinicalTrials.gov (# NCT01240460).

The primary objective of the trial was to explore the biological effect of SAR245408 and SAR245409 measured by modulation of PI3K/mTOR pathway readouts in glioblastoma tumor tissues. Other objectives were to examine the safety profile of oral administration of SAR245408 and SAR245409 in subjects with recurrent glioblastoma, to determine the levels of SAR245408 and SAR245409 in plasma and tumor tissue, to assess any anti-proliferative or pro-apoptotic effects of SAR245408 and SAR245409 on tumor cells, to measure changes in tumor after surgery in subjects receiving SAR245408 and SAR245409, to conduct genetic analysis of tumor tissue comparing, when possible, tumor tissue removed during the on-study with tumor tissue removed in a prior surgery, to evaluate the pharmacodynamic effects of SAR245408 and SAR245409 in blood and/or blood cells for identification and characterization of surrogate biomarkers associated with biological effects of SAR245408 and SAR490, and to explore the relationship between clinical response and genomic or proteomic biomarkers in the PI3K and EGFR pathways.

Patients for the study were selected with several specific criteria. They had to have a recurrent primary GBM, be candidates for surgical resection, have Karnofsky performance status (KPS)>60, and have archival tumor tissue available from their first surgical resection. Twenty one patients were selected for the study and placed into three groups. There were no significant differences in the ages or number of prior treatments between the groups (Table 1). Patients were treated with either 200 mg of SAR245408 once daily, 50 mg of SAR245409 twice daily, or 90 mg of SAR245409 once daily. These drugs are selective inhibitors of Class I PI3Ks (see Table 2 for a comparison of PI3K/mTOR inhibitor compounds), and do not significantly inhibit a panel of 130 other kinases (Cloughesy et al., 2013). SAR245408 is a pan-Class I PI3K inhibitor, while SAR245409 is a dual Class I PI3K/mTOR inhibitor (FIG. 1D). Table 3 shows the number of available patients to meet the trial objectives.

TABLE 1

Demographic and baseline characteristics

| Parameter | SAR409 50 mg twice daily (N = 8) | SAR408 200 mg once daily (N = 6) | SAR409 90 mg once daily (N = 7) | Overall (N = 21) |
|---|---|---|---|---|
| Age (years) | | | | |
| Median (Range) | 58.5 (37-71) | 54.0 (41-70) | 51.0 (37-74) | 56.0 (37-74) |
| Age category (years) | | | | |
| 18 to <65 | 5 (62.5%) | 4 (66.7%) | 6 (85.7%) | 15 (71.4%) |
| >65 | 3 (37.5%) | 2 (33.3%) | 1 (14.3%) | 6 (28.6%) |
| Sex | | | | |
| Male | 7 (87.5%) | 3 (50.0%) | 4 (57.1%) | 14 (66.7%) |
| Female | 1 (12.5) | 3 (50.0%) | 3 (42.9%) | 7 (33.3%) |
| Karnofsky performance status | | | | |
| ≥90 | 3 (37.5%) | 5 (83.3%) | 5 (71.4%) | 13 (61.9%) |
| 60 to 80 | 5 (62.5%) | 1 (16.7%) | 2 (28.6%) | 8 (38.1%) |
| Number of prior regimens | | | | |
| Median (Range) | 2.0 (1-5) | 2.5 (1-5) | 2.0 (1-5) | 2.0 (1-5) |

SD = standard deviation.

TABLE 2

Kinase inhibitors of the PI3K and mTOR family. Values are IC50s in nM.

| Compound (type) | PI3Kα | PI3Kβ | PI3Kδ | PI3Kγ | mTOR |
|---|---|---|---|---|---|
| BKM-120 (Class I PI3K) | 52 | 166 | 116 | 262 | 4600 |
| BYL719 (PI3Kα specific) | 5 | 1156 | 290 | 250 | >9100 |
| GDC-0941 (Class I PI3K) | 3 | 33 | 3 | 75 | 580 |
| GDC-0980 (dual PI3K/mTOR) | 4.8 | 27 | 6.7 | 14 | 17 |
| KU-0063794 (mTOR kinase) | >10,000 | >10,000 | — | — | 10 |
| SAR408 (Class I PI3K) | 48 | 617 | 10 | 260 | >15,000 |
| SAR409 (dual PI3K/mTOR) | 101 | 128 | 91 | 43 | 190 |

TABLE 3

Evaluation of clinical trial objectives

| | Patient # | Drug concentrations (FIG. 1B) | PI3K/mTOR inhibition (FIG. 1E) | Clinical outcome (FIG. 2A) |
|---|---|---|---|---|
| SAR409 90 mg once daily | 2027 | X | X | X |
| | 2026 | X | X | X |
| | 2025 | X | X | X |
| | 2024 | X | X | X |
| | 2023 | X | X | No post-op drug |
| | 2022 | X | X | X |
| | 2021 | X | X | X |
| SAR409 50 mg twice daily | 2008 | X | X | X |
| | 2007 | X | Tissue inadequate | |
| | 2006 | X | X | X |
| | 2005 | X | Tissue inadequate | |
| | 2004 | X | X | X |
| | 2003 | X | X | No post-op drug |
| | 2002 | X | X | X |
| | 2001 | X | X | X |

TABLE 3-continued

Evaluation of clinical trial objectives

| | Patient # | Drug concentrations (FIG. 1B) | PI3K/mTOR inhibition (FIG. 1E) | Clinical outcome (FIG. 2A) |
|---|---|---|---|---|
| SAR408 200 mg once daily | 2016 | X | X | X |
| | 2015 | X | X | X |
| | 2014 | X | X | X |
| | 2013 | X | X | X |
| | 2012 | X | X | X |
| | 2011 | X | X | X |
| Total no. patiemts | | 21 | 19 | 17 |

Trial Description and Results.

GBM patients who required tumor resection for recurrent disease received either SAR409 or SAR408 for 10-28 days prior to surgery. Tumor tissue collected during this operation (Surgery 2) was used to measure intratumoral drug concentrations, PI3K and mTOR-pathway activity, and tumor cell proliferation. Patients resumed drug treatment after recovery from surgery until clinical or radiographic evidence for further tumor progression (FIG. 1A). Twenty-one patients enrolled into the study and were assigned to one of three treatment cohorts (Table 1). The first cohort of patients (n=6) received SAR408, 200 mg once daily, the second cohort received SAR409, 90 mg HCl salt capsule (API=79.2 mg) once daily (n=7) and the third cohort received SAR409 50 mg HC; salt capsule (API=44 mg) twice daily (n=8). Tumor resection was performed at defined time intervals after the last pre-operative drug dose: at 24 h for the SAR408 cohort due to a longer plasma half-life of SAR408; at the Cmax (3 h) for the SAR409 90 mg daily cohort; and at the Cmin (12 h) for the SAR409 50 mg twice daily cohort. Cmax and Cmin timepoints were estimated based on plasma concentrations in previous studies with these agents. The median intratumoral drug concentration of SAR408 was 20.7 µM (range 12.4-29.2 µM) (FIG. 1B, left panel), well above the half maximal inhibitory concentration (IC50) for inhibition of PI3Ks ($\alpha$:48 nM, $\beta$:617 nM; $\delta$:10 nM; $\gamma$:260 nM; mTOR>15,000 nM). For patients treated with SAR409 90 mg QD, the median intratumoral Cmax concentration was 0.17 µM (range 0.0231-0.751 µM) (FIG. 1B, right panel), a drug concentration that is near the in-vitro IC50 for inhibition of PI3K and mTOR ($\alpha$:101 nM, $\beta$:128 nM; $\delta$:91 nM; $\gamma$:43 nM; mTOR:190 nM) and reduced phosphorylation of Akt and S6 Ribosomal Protein in a human GBM tumor sphere cell line by about 50% (FIG. 1C).

Figure 1E:
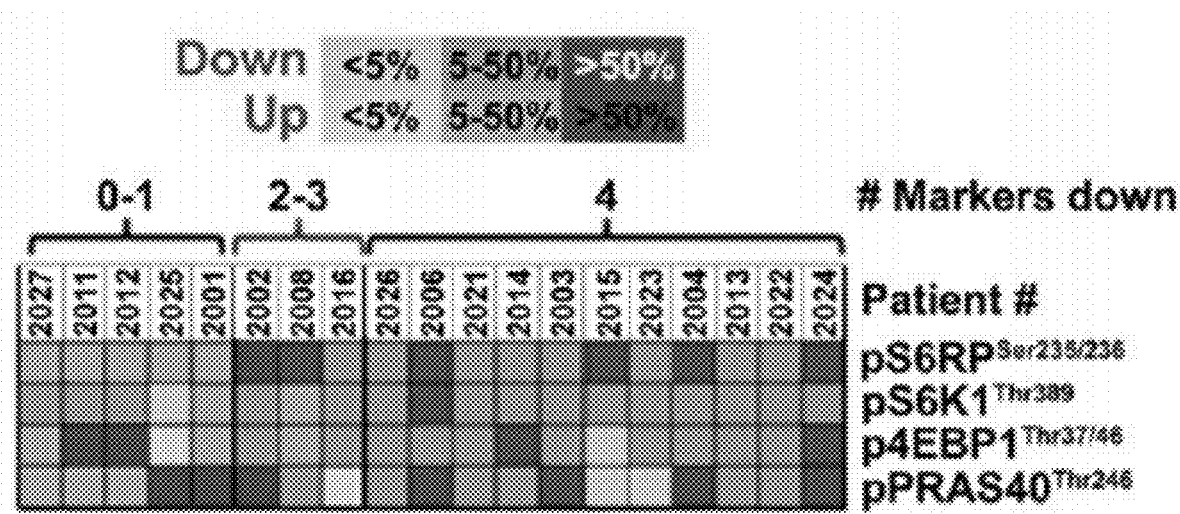
Figure 1E:
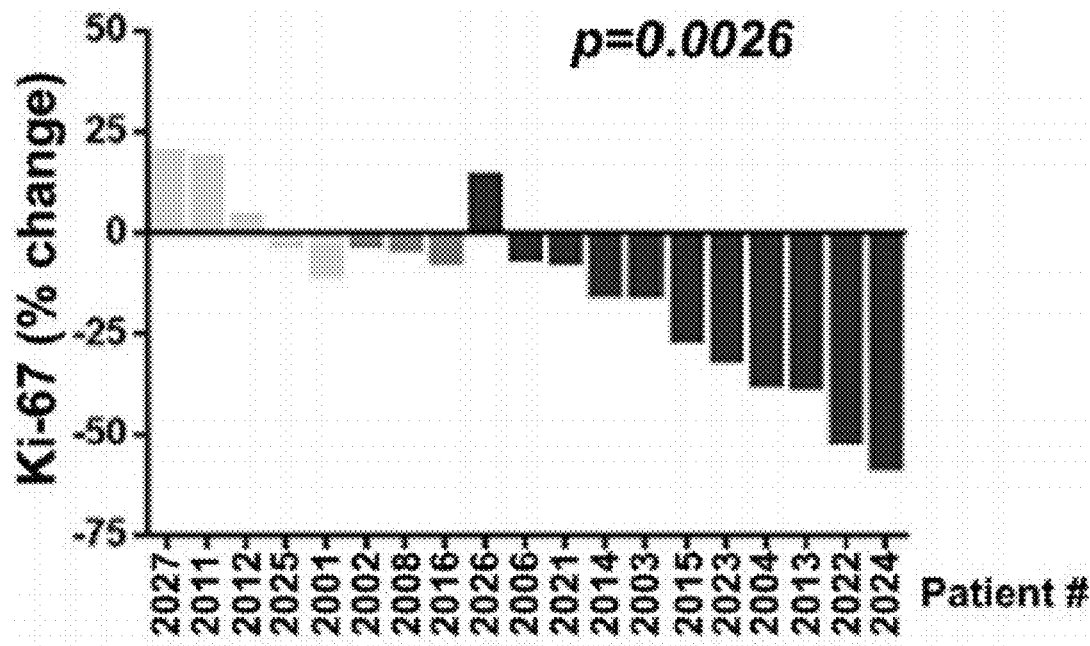

To evaluate pharmacodynamic effects in tumor tissue, immuno-histochemistry (IHC) was performed with phosphorylation-site specific antibodies against four PI3K/mTOR pathway components: Proline-Rich Akt Substrate of 40-kDa (PRAS40, threonine246), ribosomal protein S6 kinase 1 (S6K1, threonine 389), eukaryotic translation initiation factor 4E-binding protein 1 (4E-BP1, threonine 37/46), and S6 Ribosomal Protein (S6RP, serine 235/236) (FIG. 1D). For each marker staining of several thousand tumor cells was quantified and the staining intensity in the "on-treatment"-biopsy (Surgery 2) was compared with the staining intensity in the tumor sample collected from the same patient at diagnosis (Surgery 1). This "matched-pair" analysis included 19/21 evaluable patients (Table 3) who received at least one dose of study drug, had detectable phospho-S6RP in the pre-treatment sample (Surgery 1), and had tissue of sufficient quality collected on treatment (Surgery 2). The majority of patients showed evidence for PI3K/mTOR pathway inhibition. 14/19 (74%) examined tumors showed decreased staining for at least two PI3K/mTOR-pathway markers. 11/19 (58%) tumors showed decreased staining for all four examined pathway markers, including the Akt substrate PRAS-40 (FIG. 1E, upper panel). Additional staining with an antibody against the Ki-67 protein showed that pathway inhibition was correlated with inhibition of tumor cell proliferation (FIG. 1E, lower panel), consistent with the broad antiproliferative activity of PI3K inhibitors in cancer cell lines (Wallin et al., 2011).

Patients Treated with SAR245408 or SAR245409 had Inhibition of the PI3K/mTOR Pathway and Reduced Cellular Proliferation.

The design of the trial allowed comparison of the initial glioma (Surgery 1) in these patients to the recurrent glioma which was treated with drug before surgical resection (Surgery 2). Immunohistochemical staining (IHC) was performed on the samples and pathway inhibition was measured via pS6 Ser235/6, pS6K1 Thr389, p4E-BP1 Thr37/46, and pPRAS40 Thr246 (FIG. 1E, upper panel). Cellular proliferation was measured via Ki-67 IHC. These IHC measurements were compared to one another and reported as a percentage decrease or increase of Surgery2/Surgery 1. Samples which had reduction of all four phospho-protein measurements in Surgery 2 also had the greatest relative decreases in cellular proliferation (FIG. 1E, lower panel). Samples which had no inhibition of any pharmacodynamic biomarker or inhibition of only one pharmacodynamic biomarker were most likely to see a relative increase in proliferation.

Figures 12A, 12B:
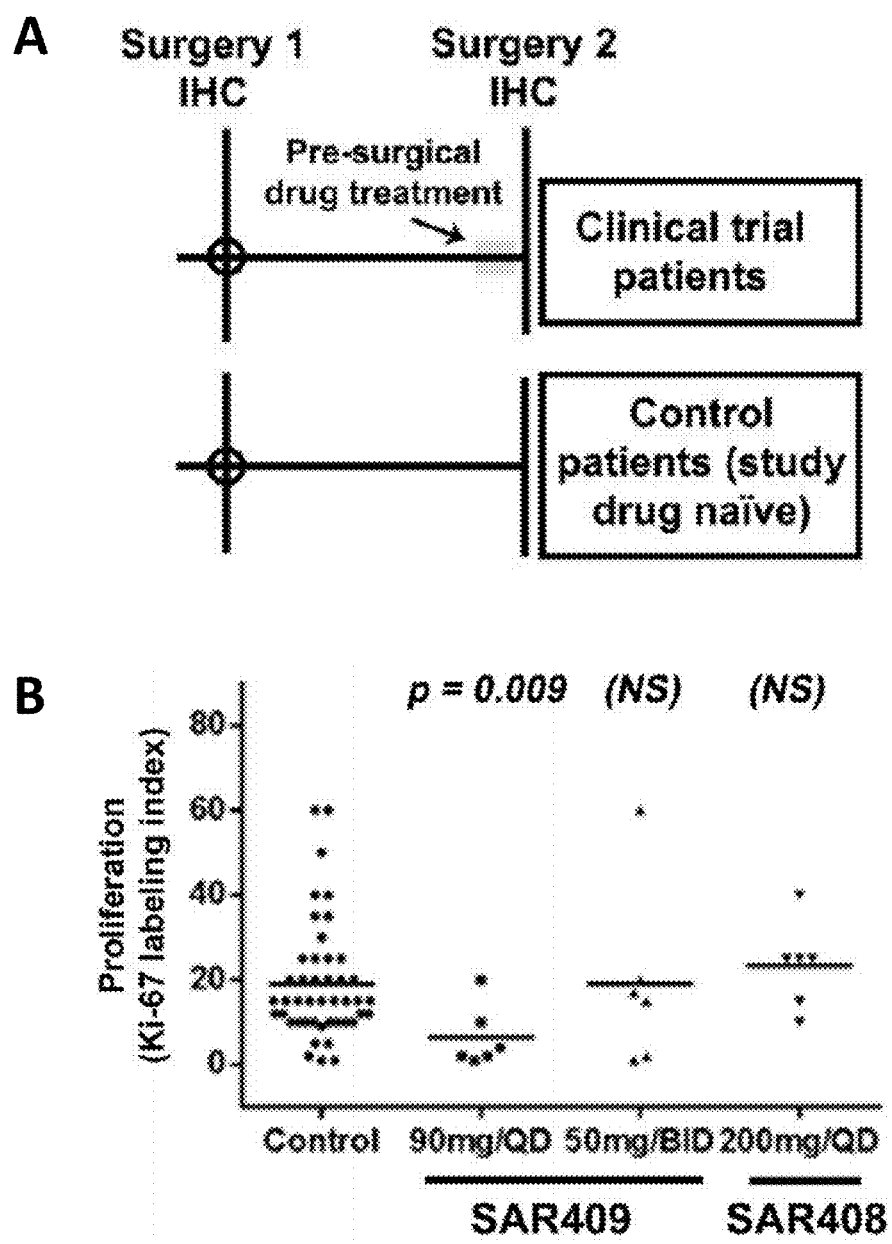
FIGS. 12A-12B: Cellular proliferation in patients treated with SAR245409 was decreased. (A) A control population of patients who were not treated with any PI3K inhibitor and had two surgical resections were stained with Ki-67 to measure cell proliferation. (B) This was compared to the three clinical trial arms of 90 mg/QD SAR245409, 50 mg/BID SAR245409, or 200 mg/QD SAR245408. Proliferation was statistically significantly reduced in the 90 mg/QD SAR245409 arm of the trial compared to control untreated patients (p=0.009). The other two arms were not significantly different than the control arm. NS: not significant

To compare the relative change in cellular proliferation in the three drug arms and a drug naïve population, a control population was formed of patients who had not been treated with any PI3K inhibitor and surgical samples available from two surgical resections and compared their relative proliferation via Ki-67 IHC (FIG. 12A). This control group was compared with the three arms of the trial. Patients who were given 90 mg of SAR245409 daily saw a statically significant decrease in proliferation when compared to the control population (FIG. 12B). There was no statistically significant change in proliferation between the control group and the other arms of the trial.

A Patient Who Responded to SAR245409 had Amplified Mutated PDGFRA.

Figure 2A:
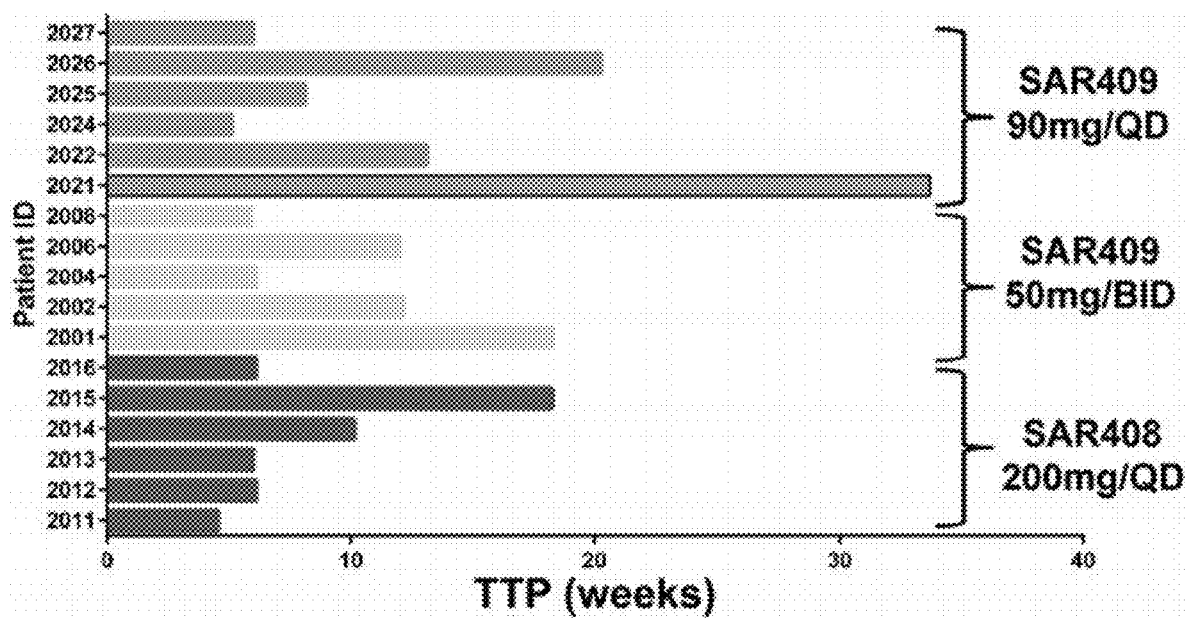
FIGS. 2A-2B: PDGFRA-mutant GBM shows "outlier response" to SAR409. (A) Time-to-Progression for all patients who resumed treatment with SAR409 or SAR408 after Surgery 2 (n=17). (B) PDGFRA amplification in patient #2021. Shown are array-cGH results from the "on-treatment" biopsy (Surgery 2). The sample for patient #2021 shows copy number gain (log 2: 0.8) spanning the PDGFRA gene locus on chromosome 4q12.

The endpoint for the clinical trial was an adverse event or progression of the disease. The median time to progression of a patient in this trial was 7.14 weeks (range 0-33.71). The medians of the individual arms were 6.14 weeks (range 4.57-18.29) for SAR245408, 9.07 weeks (range 0-18.29 weeks) for 50 mg BID SAR245409, and 8.14 weeks (range 0-33.71) for 90 mg QD SAR245409. There was not a statistically significant change in TTP progression in any arm of the trial (FIG. 2A). One patient in the 90 mg/QD SAR245409 arm of the trial was noted, patient #2021, who had a response to SAR245409 and a 33.71 week time to progression, nearly twice that of any other patient.

Figure 5:
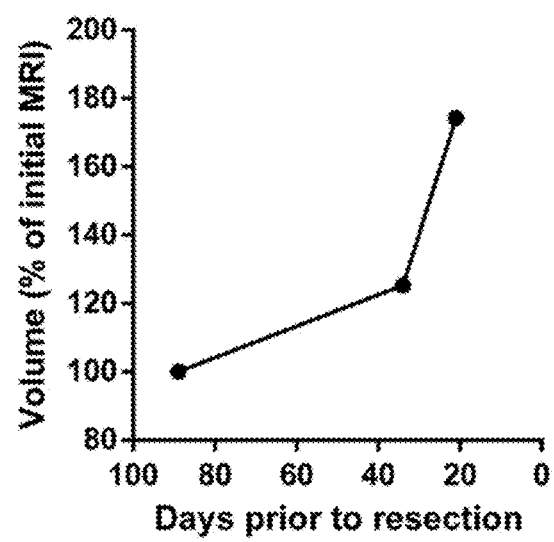
FIG. 5: Progressive Tumor Growth in Patient #2021 prior to study enrollment. Quantification of tumor volume determined from brain T1 post-contrast MRI images. Enhancing tumor volume was quantified by first manually defining the relative region of tumor burden, then thresholding post-contrast T1-weighted images within these regions, and then manually editing the resulting masks to exclude any non-tumor tissue. Tumor volumes were calculated by multiplying the total number of contrast-enhancing voxels by the voxel resolution. The percentage change in tumor volumes relative to baseline were calculated by (Vcurrent−Vbaseline)/Vbaseline×100%.

Seventeen patients resumed SAR408 or SAR409 postoperatively and tolerated it well (Tables 4 and 5, below); the remaining 2 patients did not resume the study drug following surgery due to disease-related complications. Among seventeen patients, 16 suffered tumor recurrence within six months (FIG. 2A). Patient #2021 whose recurrent tumor showed accelerating tumor growth prior to enrollment (FIG. 5) remained on study for about eight months. Since a complete tumor resection was not possible for this patient, the effects of postoperative SAR409 treatment on the residual tumor volume were monitored with consecutive brain MRIs which showed a complete regression of the target lesion. The on-treatment biopsy (Surgery 2) sample from this patient showed a decrease in tumor cell proliferation and all four PI3K/mTOR pathway markers on SAR409 treatment (see FIG. 1E). However, the tumor later developed acquired resistance to SAR409 with appearance of a new lesion near the midline of brain at which point patient #2021 was taken off the study.

Figure 2B:
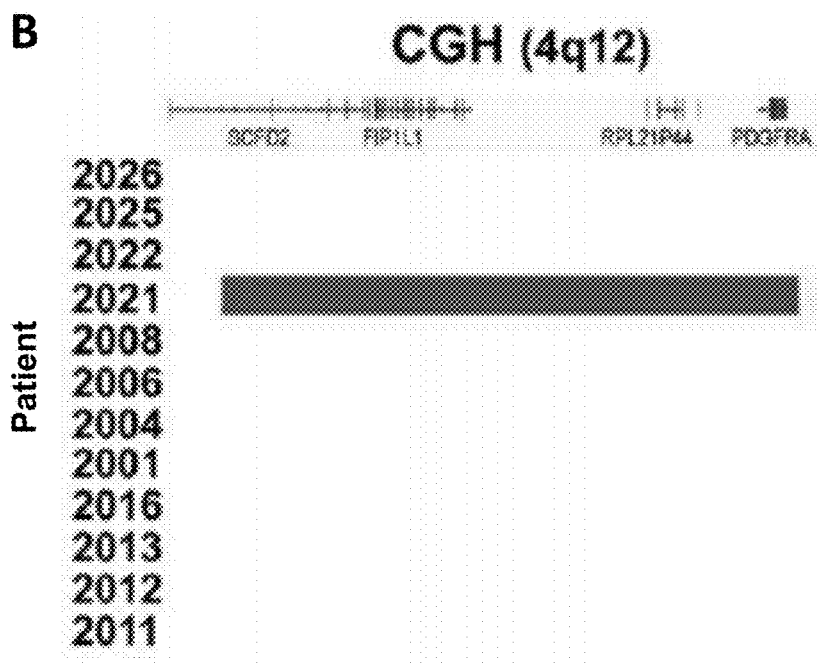
Figure 6:
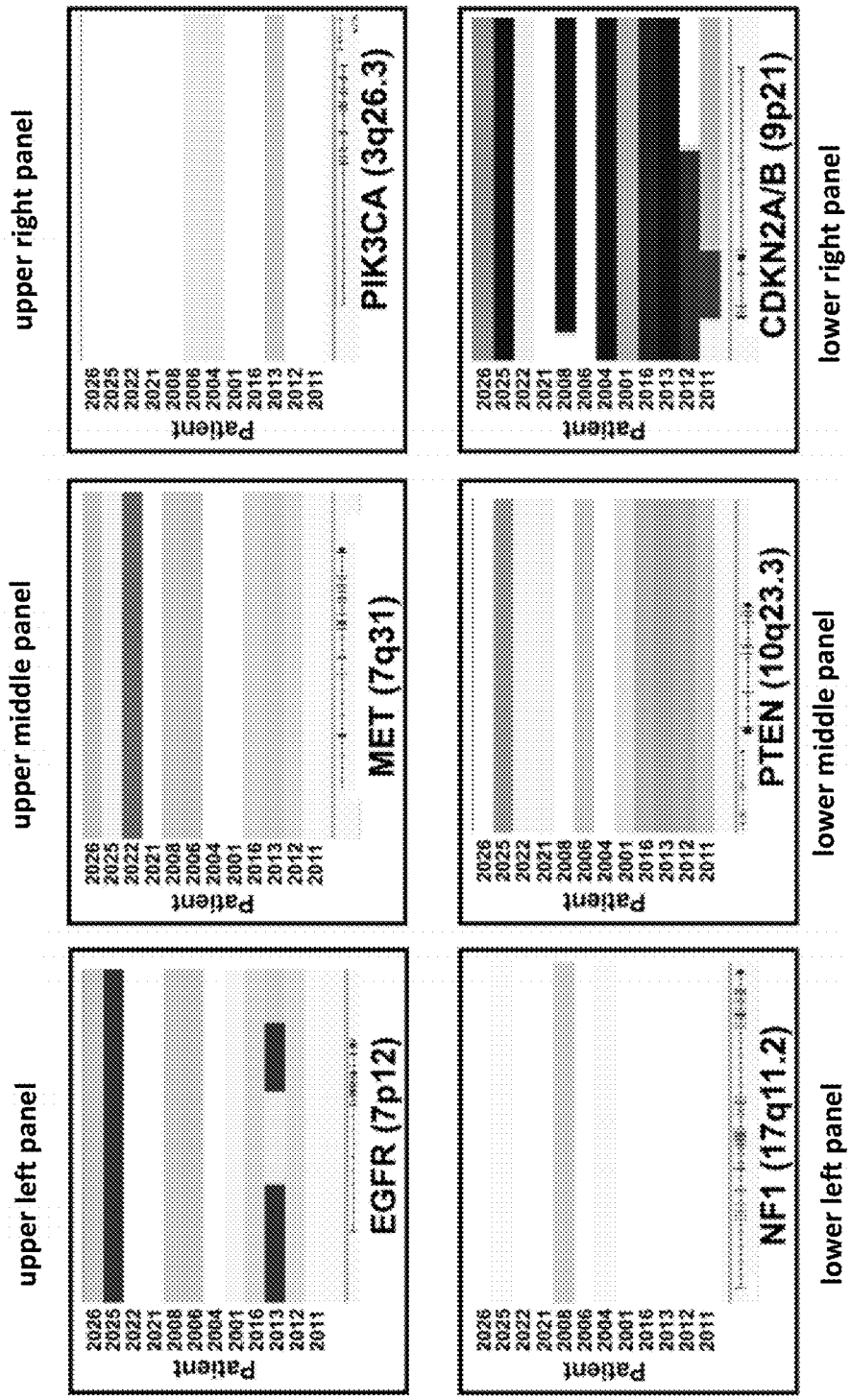
FIG. 6: Array-CGH analysis of "on-treatment" (surgery 2) frozen tumor samples. Shown are the genomic loci for EGFR (upper left panel), MET (upper middle panel), PIK3CA (upper right panel), NF1 (lower left panel), PTEN (lower middle panel), and CDKN2A/B (lower right panel) using the Integrative Genomics Viewer (IGV, Broad Institute). Genomic gains or losses were scored using CGH Analytics Software (Agilent). Aberrations of log 2 ratio less than −0.3 were considered as losses, and aberrations of log 2 ratio greater than 0.3 were considered gains.
Figures 7A, 7B, 7C:
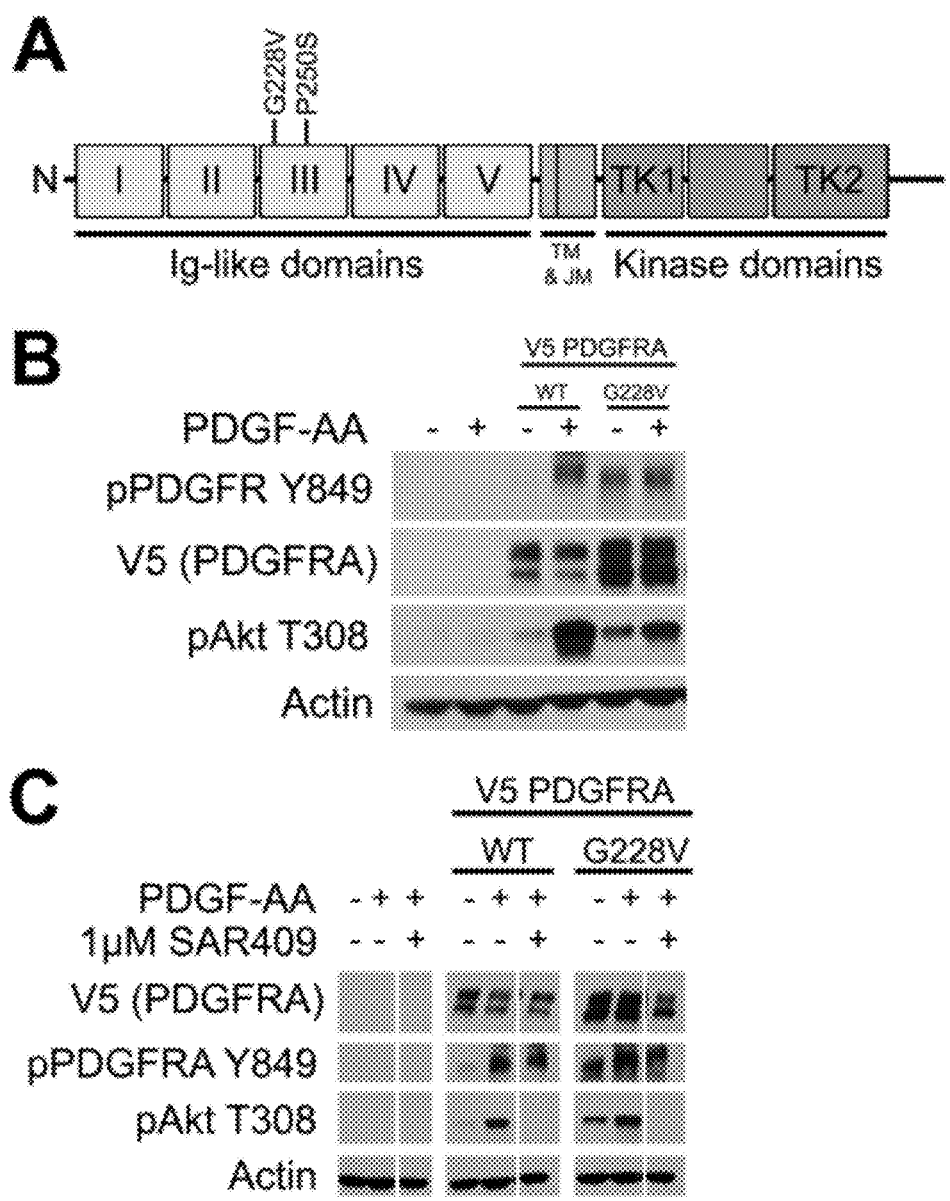
FIGS. 7A-7C: PDGFRA missense mutations in tumor #2021. (A) Cartoon of the PDGFRα protein domains and the location of the two somatic mutations in the extracellular domain of PDGFRA (G228V, P250S). (B) Western Blot of Pdgfra/Pdgfrb double knock-out MEFs transduced with V5-tagged wild-type PDGFRA (WT) or G228V PDGFRA. Cells were serum starved overnight and then stimulated for five minutes with PDGF-AA (5 ng/mL). (C) SAR409 blocks ligand induced AKT activation by WT-PDGFR and G228V-PDGFRA. Cells were pretreated for one hour with SAR409 (1 µM) prior to simulation with PDGF-AA (5 ng/mL) for five minutes.

To explore the molecular basis for the response of tumor #2021 to SAR409, the "on-treatment" frozen tissue biopsies were surveyed for alterations in the PI3K/mTOR pathway. Most tumors showed alterations in PI3K pathway members predicted to result in pathway activation, including silencing of PTEN or NF1 and gain-of-function lesions involving EGFR (EGFRvIII and EGFR missense mutations), PIK3CA, and MET (Table 4, below) (FIG. 6). The tumor from the outlier responder (#2021), but none of the other tumors, harbored an amplicon that included the PDGFRA coding region (FIG. 2B) and two missense mutations in the PDGFRA extracellular domain. The mutants were engineered and expressed in Pdgfra/Pdgfrb double knockout cells, and examined their ability to activate PDGFRA and the PI3K pathway in the absence of exogenous ligand. The G228V-PDGFRA mutant was constitutively phosphorylated and resulted in aberrant Akt activation which could be inhibited by SAR409 (FIG. 7C).

genomic hybridization array (aCGH). PDGFRA was found to be amplified in patient #2021 (log 2=0.7786). This is the only patient found to have amplification in this gene. There were no gains or losses detected in EGFR, MET, NF1, the FGFR family, PTEN, or PIK3R1 in patient #2021 (FIG. 2B). Fluorescent in situ hybridization (FISH) was performed on tumor samples removed from both surgeries of patient

TABLE 4

PI3K pathway alterations in "surgery 2" samples.

| Patient ID | Drug | TTP (wks) | Sequencing | PDGFRA chr. 4q12 array CGH | EGFRVIII (IHC) | EGFR chr. 7p12 (FISH) | EGFR chr. 7p12 (array CGH) | MET, chr. 7q31 (array CGH) | PTEN, chr. 10q23.3 (aCGH) | PTEN Mutation | PTEN Protein IHC |
|---|---|---|---|---|---|---|---|---|---|---|---|
| 2027 Surgery 2 | SAR409 90 mg/QD | 6 | N/D | N/D | NEG | NEG | N/D | N/D | N/D | NON MUT | NORMAL |
| 2026 Surgery 2 | SAR409 90 mg/QD | 20.29 | PIK3CA MUT (M1043V) | NORMAL | NEG | NEG | GAIN | GAIN | NORMAL | NON MUT | HETEROGENOUS |
| 2025 Surgery 2 | SAR409 90 mg/QD | 8.14 | EGFR MUT (S123Y, A298T, A289V) | NORMAL | NEG | AMP | AMP | NORMAL | LOSS | NON MUT | LOSS OF STAINING |
| 2024 Surgery 2 | SAR409 90 mg/QD | 5.14 | N/D | N/D | NEG | NEG | N/D | N/D | N/D | N/D | HETEROGENOUS |
| 2022 Surgery 2 | SAR409 90 mg/QD | 13.14 | No mutation detected | NORMAL | NEG | NEG | NORMAL | AMP | NORMAL | NON MUT | HETEROGENOUS |
| 2021 Surgery 2 | SAR409 90 mg/QD | 33.71 | PDGFRA MUT (G228V, P250S) | AMP | NEG | N/A | NORMAL | NORMAL | NORMAL | NON MUT | N/D |
| 2008 Surgery 2 | SAR409 50 mg/BID | 6 | NF1 Loss and 2bp DEL | NORMAL | NEG | NEG | GAIN | GAIN | NORMAL | MUT | NORMAL |
| 2006 Surgery 2 | SAR409 50 mg/BID | 12 | No mutation detected | NORMAL | NEG | NEG | GAIN | GAIN | LOSS | NON MUT | NORMAL |
| 2004 Surgery 2 | SAR409 50 mg/BID | 6.14 | PI3KR1 Loss | NORMAL | NEG | NEG | NORMAL | NORMAL | NORMAL | NON MUT | HETEROGENOUS |
| 2002 Surgery 2 | SAR409 50 mg/BID | 12.14 | N/D | N/D | NEG | NEG | N/D | N/D | N/D | N/D | HETEROGENOUS |
| 2001 Surgery 2 | SAR409 50 mg/BID | 18.29 | No mutation detected | NORMAL | NEG | NEG | NORMAL | NORMAL | NORMAL | MUT | LOSS OF STAINING |
| 2016 Surgery 2 | SAR408 200 mg/QD | 6.14 | EGFR MUT (P596L) | NORMAL | NEG | NEG | GAIN | GAIN | LOSS | MUT | HETEROGENOUS |
| 2015 Surgery 2 | SAR408 200 mg/QD | 18.29 | N/D | N/D | NEG | NEG | N/D | N/D | N/D | N/D | HETEROGENOUS |
| 2014 Surgery 2 | SAR408 200 mg/QD | 10.14 | N/D | N/D | POS | AMP | N/D | N/D | N/D | N/D | LOSS OF STAINING |
| 2013 Surgery 2 | SAR408 200 mg/QD | 6 | No mutation detected | NORMAL | POS | AMP | AMP | GAIN | LOSS | NON MUT | HETEROGENOUS |
| 2012 Surgery 2 | SAR408 200 mg/QD | 6.14 | No mutation detected | NORMAL | NEG | NEG | NORMAL | NORMAL | LOSS | MUT | HETEROGENOUS |
| 2011 Surgery 2 | SAR408 200 mg/QD | 4.57 | No mutation detected | NORMAL | NEG | NEG | NORMAL | NORMAL | LOSS | NON MUT | LOSS OF STAINING |

Abbreviations:
N/D = not determined due to insufficient frozen tumor tissue;
AMP = amplified;
PTEN IHC Normal is defined as ≥90% tumor cells with 2+ staining (see Methods);
PTEN IHC LOSS OF STAINING is defined as ≥90% tumor cells with 0-1+ staining.

DNA samples were obtained when possible from the surgical samples of all patients in the trial. Genetic gain or loss was analyzed using a 1 million probe comparative #2021 (briefly, tumor samples from the first and second surgeries were fixed and analyzed for PDGFRA and a chromosome enumeration probe (CFP) for the chromosome 4 centromere), and amplification of PDGFRA was present. A reduction in PDGFRA amplification was also observed after treatment with SAR245409 in the FISH from the second surgery, although some amplification was still detected. The reduction of amplification of PDGFRA after treatment was also observed in patient #2014. Amplification of EGFR in patient #2014 was unchanged by treatment.

Novel PDGFRA Mutations Discovered in Patient #2021.

DNA extracted from the surgery 2 sample was sequenced using the MiSeq platform. DNA was also extracted from blood samples from each patient as a control. Two novel PDGFRA mutations were found in patient #2021 tumor DNA at G228 to K and at P250 to S (FIG. 7A). A different substitution at amino acid 250 (P250H) has been reported in COSMIC, but no mutations at amino acid 228 have previously been reported. Both mutations were found in the extracellular ligand binding domain of PDGFRA. MiSeq reads of G228V and P250S mutations revealed the mutant mutation rate of G228V mutation is 13%, and the rate of P250S mutation was 20%. Further analysis of the MiSeq reads revealed that the mutations are on separate alleles and the patient did not express any double 228/250 mutant PDGFRA. It has previously been described that point mutations in high grade pediatric glioma in the same domain as the mutations described here, although the prior studied did not characterize the mutations (Paugh et al., 2013). Using site directed mutagenesis the mutations were made and expressed them alongside wild-type (WT) PDGFRA in a Pdgfra/Pdgfrb knock-out immortalized MEF system (FMEFs). The G228V mutation shows ligand independent phosphorylation of the receptor (FIG. 7B). The P250S mutation was also analyzed and did not have any ligand-independent receptor activity and appeared to respond to ligand with similar duration and magnitude as WT PDGFRA.

Analysis of Patient Tumor Cells.

Figure 8:
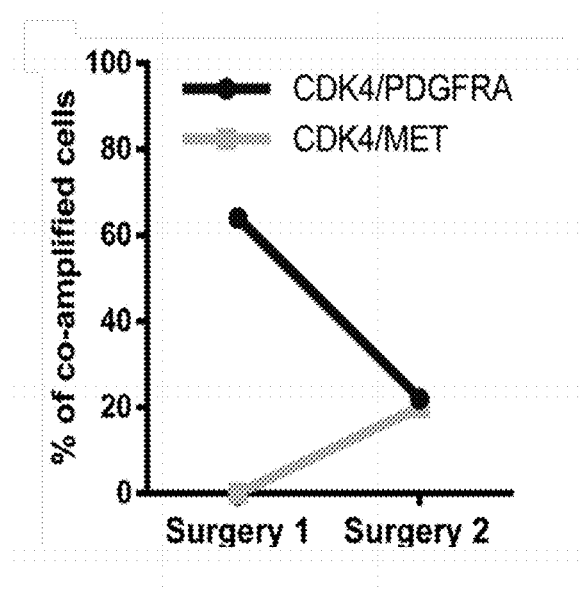
FIG. 8: Depletion of the PDGFRA-amplified GBM tumor cell population following PI3K/mTOR blockade. A graphical depiction of the percentage of cells with co-amplification of CDK4/PDGFRA or CDK4/MET in FISH samples from a GBM patient who was enrolled in a Phase I clinical trial with SAR409, received single agent SAR409 for 27 months, and then underwent a second tumor resection at the time of tumor recurrence (Surgery 2). FISH analysis of the initial surgical tumor sample (Surgery 1) showed numerous tumor cells with amplification of both PDGFRA and CDK4. This tumor cell population was markedly reduced in the recurrent tumor (Surgery 2) which revealed the emergence of another tumor cell population with co-amplification of both CDK4 and MET. Cells were labeled with markers for gene loci of CDK4, PDGFRA, and MET.

To more fully characterize the relationship between PDGFRA gene dosage and clinical response to PI3K/mTOR blockade, the status of PDGFRA in the tumor tissue was analyzed by fluorescence in situ hybridization (FISH) for all patients who had received postoperative drug treatment (n=17). The pretreatment tumor specimen of three patients (#2014, #2021, and #2022) contained tumor cells with PDGFRA gene amplification. These cells represented the majority of tumor cells in patient #2021, but only a subpopulation in patients #2014 and #2022. In patient #2021, PI3K/mTOR blockade by SAR409 led to tumor regression and a depletion of PDGFRA-amplified tumor cells in the "on-treatment" biopsy (Surgery 2). Patient #2014 harbored two distinct tumor cell populations, one harboring PDGFRA amplification and the other harboring EGFR amplification, a mosaic pattern that has been reported in other glioblastomas (Snuderl et al., 2011; Szerlip et al., 2012). A depletion of the PDGFRA amplified tumor cells was observed after SAR409 treatment. In contrast, there was no reduction of the EGFR amplified tumor cells. Patient #2022 showed scattered PDGFRA-amplified tumor cells (4/300 cells) in the pre-treatment (Surgery 1) specimen but these were no longer detectable in on-treatment biopsy (Surgery 2) (Table 5, below). The impact of SAR409 was also examined in a patient with PDGFRA amplified GBM enrolled in another SAR409 Phase I clinical trial (NCT00704080) (Wen et al, 2015). This patient started SAR409 with concurrent temozolomide following radiation, remained on single-agent SAR409 for 27 months, and underwent a second tumor resection at the time of tumor relapse. Compared to the original tumor sample (Surgery 1), the recurrence specimen (Surgery 2) showed a marked reduction in PDGFRA amplified tumor cells and the emergence of a new tumor cell population with MET gene amplification (FIG. 8).

TABLE 5

PDGFRA FISH in "surgery 1" and "surgery 2" tumor samples.

| Patient ID | Amplification of PDGFR (FISH 4q12 region) | PDGFRA, chr. 4q12 (aCGH) |
|---|---|---|
| 2021 Surgery 1 | POSITIVE | |
| 2021 Surgery 2 | FOCAL (6/300 cells) | AMP (log 2: 0.7789) |
| 2014 Surgery 1 | POSITIVE | |
| 2014 Surgery 2 | NEGATIVE | N/D |
| 2022 Surgery 1 | FOCAL (4/300 cells) | |
| 2022 Surgery 2 | NEGATIVE | NORMAL |
| 2027 Surgery 1 | NEGATIVE | |
| 2027 Surgery 2 | NEGATIVE | N/D |
| 2026 Surgery 1 | NEGATIVE | |
| 2026 Surgery 2 | NEGATIVE | NORMAL |
| 2025 Surgery 1 | NEGATIVE | |
| 2025 Surgery 2 | NEGATIVE | NORMAL |
| 2024 Surgery 1 | NEGATIVE | |
| 2024 Surgery 2 | NEGATIVE | N/D |
| 2008 Surgery 1 | NEGATIVE | |
| 2008 Surgery 2 | NEGATIVE | NORMAL |
| 2006 Surgery 1 | NEGATIVE | |
| 2006 Surgery 2 | NEGATIVE | NORMAL |
| 2004 Surgery 1 | NEGATIVE | |
| 2004 Surgery 2 | NEGATIVE | NORMAL |
| 2002 Surgery 1 | NEGATIVE | |
| 2002 Surgery 2 | NEGATIVE | N/D |
| 2001 Surgery 1 | NEGATIVE | |
| 2001 Surgery 2 | NEGATIVE | NORMAL |
| 2016 Surgery 1 | NEGATIVE | |
| 2016 Surgery 2 | NEGATIVE | NORMAL |
| 2015 Surgery 1 | NEGATIVE | |
| 2015 Surgery 2 | N/A | N/D |
| 2013 Surgery 1 | NEGATIVE | |
| 2013 Surgery 2 | NEGATIVE | NORMAL |
| 2012 Surgery 1 | NEGATIVE | |
| 2012 Surgery 2 | NEGATIVE | NORMAL |
| 2011 Surgery 1 | NEGATIVE | |
| 2011 Surgery 2 | NEGATIVE | NORMAL |

Safety.

Adverse events were graded using NCI Common Terminology Criteria for Adverse Events (CTCAE) version 4.0. Adverse events were recorded from first study treatment intake to 30 days post last dose of study drug. All 21 patients experienced one or more Treatment-Emergent Adverse Events (TEAE), with Grade 3 or 4 TEAEs reported for 7 patients (87.5%) in the SAR409 twice daily cohort, 2 patients (33.3%) in the SAR408 once daily cohort, and 4 patients (57.1%) in the SAR409 once daily cohort. Treatment-emergent AEs that were assessed by the investigator to be related to study drug (possibly related or probably related) were reported for 8 patients (100.0%) in the SAR409 twice daily cohort, 3 patients (50.0%) in the SAR408 once daily cohort, and 7 patients (100.0%) in the SAR409 once daily cohort.

Treatment-emergent SAEs were reported for 5 patients (62.5%) in the SAR409 twice daily cohort, 1 patient (16.7%) in the SAR408 once daily cohort, and 1 patient (14.3%) in the SAR409 once daily cohort, with study drug-related treatment-emergent SAEs reported for 1 patient (12.5%) in the SAR409 twice daily cohort, and 1 patient (14.3%) in the SAR409 once daily cohort. Two deaths in the SAR409 twice daily cohort (25.0%) were attributed to a TEAE (Patient #2008, respiratory failure, not related to study drug and Patient #2003, subdural hematoma, not related to study drug). There were no deaths attributed to TEAEs in the other 2 treatment cohorts.

Treatment-emergent AEs are summarized in the Table 6 below.

TABLE 6

Overview of treatment-emergent adverse events.

| Patients with | SAR409 50 mg twice daily (N = 8) n (%) | SAR408 200 mg once daily (N = 6) n (%) | SAR409 90 mg once daily (N = 7) n (%) | Overall (N = 21) n (%) |
|---|---|---|---|---|
| Any TEAE[a] | 8 (100.0) | 6 (100.0) | 7 (100.0) | 21 (100.0) |
| Any Grade 3/4 TEAE[b] | 7 (87.5) | 2 (33.3) | 4 (57.1) | 13 (61.9) |
| Any related TEAE | 8 (100) | 3 (50.0) | 7 (100.0) | 18 (85.7) |
| Any related Grade 3/4 TEAE[c] | 4 (50.0) | 0 | 4 (57.1) | 8 (38.1) |
| Any treatment emergent SAE | 5 (62.5) | 1 (16.7) | 1 (14.3) | 7 (33.3) |
| Any Grade 3/4 treatment-emergent SAE | 5 (62.5) | 1 (16.7) | 1 (14.3) | 7 (33.3) |
| Any related treatment-emergent SAE | 1 (12.5) | 0 | 1 (14.3) | 2 (9.5) |
| Any related Grade 3/4 treatment-emergent SAE | 1 (12.5) | 0 | 1 (14.3) | 2 (9.5) |
| Any TEAE leading to death | 2 (25.0) | 0 | 0 | 2 (9.5) |
| Any TEAE leading to permanent treatment discontinuation | 3 (37.5) | 0 | 2 (28.6) | 5 (23.8) |
| Patients with any TEAE leading to dose reduction or interruption | 6 (75.0) | 0 | 2 (28.6) | 8 (38.1) |

[a]Treatment-emergent adverse events were those with an onset date from first study treatment intake to 30 days after the last study treatment intake.
[b]Adverse events were graded according to the CTCAE v.4 scale.
[c]Related TEAEs were those that were assessed by the investigator to be either "possibly related" or "probably related" to study drug.
CTCAE = Common Terminology Criteria for Adverse Events;
SAE = serious adverse event;
TEAE = treatment-emergent adverse event.

All 21 patients discontinued treatment prior to receiving 1 year of postsurgery treatment. Time to tumor progression (TTP) for all patients is presented FIG. 2A. The reasons for treatment discontinuation are presented in Table 7 below.

TABLE 7

Primary reason for discontinuation from study treatment

| | SAR409 50 mg twice daily (N = 8) n (%) | SAR408 200 mg once daily (N = 6) n (%) | SAR409 90 mg once daily (N = 7) n (%) | Overall (N = 21) n (%) |
|---|---|---|---|---|
| Adverse Event or SAE unrelated to disease progression | 3 (37.5) | 0 | 2 (28.6) | 5 (23.8) |
| Disease progression per modified RANO | 4 (50.0) | 6 (100.0) | 4 (57.1) | 14 (66.7) |
| Clinical disease progression per principal investigator | 0 | 0 | 1 (14.3) | 1 (4.8) |
| Investigator decision | 1 (12.5) | 0 | 0 | 1 (4.8) |

Abbreviations:
RANO = Response Assessment for Neuro-Oncology (Andrews et al., 1999);
SAE = serious adverse event.

Overall, the toxicity profile for both agents was as expected and consistent with previous studies (Cloughesy et al., 2008; Yu et al., 2014). SAR409-related (n=15 patients, 100%) TEAEs included fatigue (9 patients, 60%), ALT increased (6 patients, 40%), nausea (4 patients, 26.7%), hypophosphatemia (3 patients, 20%), lipase increased (3 patients, 20%), diarrhea (2 patients, 13.3%), and dysgeusia (2 patients, 13.3%). SAR408-related (n=3 patients, 50%) TEAEs included fatigue (2 patients, 33.3%). The only SAE that was reported for more than 1 patient was abdominal pain.

Two SAEs were found to be related to study drug: 1 patient in the SAR409 twice daily cohort (Grade 1 abdominal pain, Grade 1 nausea, and Grade 1 vomiting, and Grade 3 ALT increased, all considered related to study drug and all recovered) and 1 patient in the SAR409 once daily cohort (Grade 4 platelet count decreased, related, recovered).

There was some evidence for liver toxicity associated with SAR409, with study drug-related TEAEs of (a) ALT increased, reported for 4 patients (50.0%, 2 patients with Grade 3 or 4) in the SAR409 twice daily and 2 patients (28.6%, 1 with Grade 3 or Grade 4) in the SAR409 once daily cohort; (b) AST increased, reported for 1 patient (12.5%) in the SAR409 twice daily cohort and 1 patient (14.3%) in the SAR409 once daily cohort; (c) Blood bilirubin increased, reported for 1 patient (12.5%) in the SAR409 twice daily cohort; (d) Gamma-glutamyltransferase increased, reported for 1 patient (14.3%) in the SAR409 once daily cohort; (e) ALT increased, leading to: dose delays for 2 patients (25.0%) in the SAR409 twice daily cohort and 1 patient (14.3%) in the SAR409 once daily cohort, dose reductions for 3 patients (37.5%) in the SAR409 twice daily cohort, discontinuation from study drug for 1 patient (12.5%) in the SAR409 twice daily cohort and 1 patient (14.3%) in the SAR409 once daily cohort.

However, no patients met the criteria for drug-induced liver injury (Hy's Law: ALT>3×ULN or AST>3×ULN and total bilirubin >2×ULN). No TEAEs of ALT, increased, AST increased, blood bilirubin increased, or gamma-glutamyl-transferase increased were reported for the SAR408 once daily cohort. There was no evidence of cardiovascular toxicity.

PDGRF Mutations in Human Cancers.

Figures 25A, 25B:
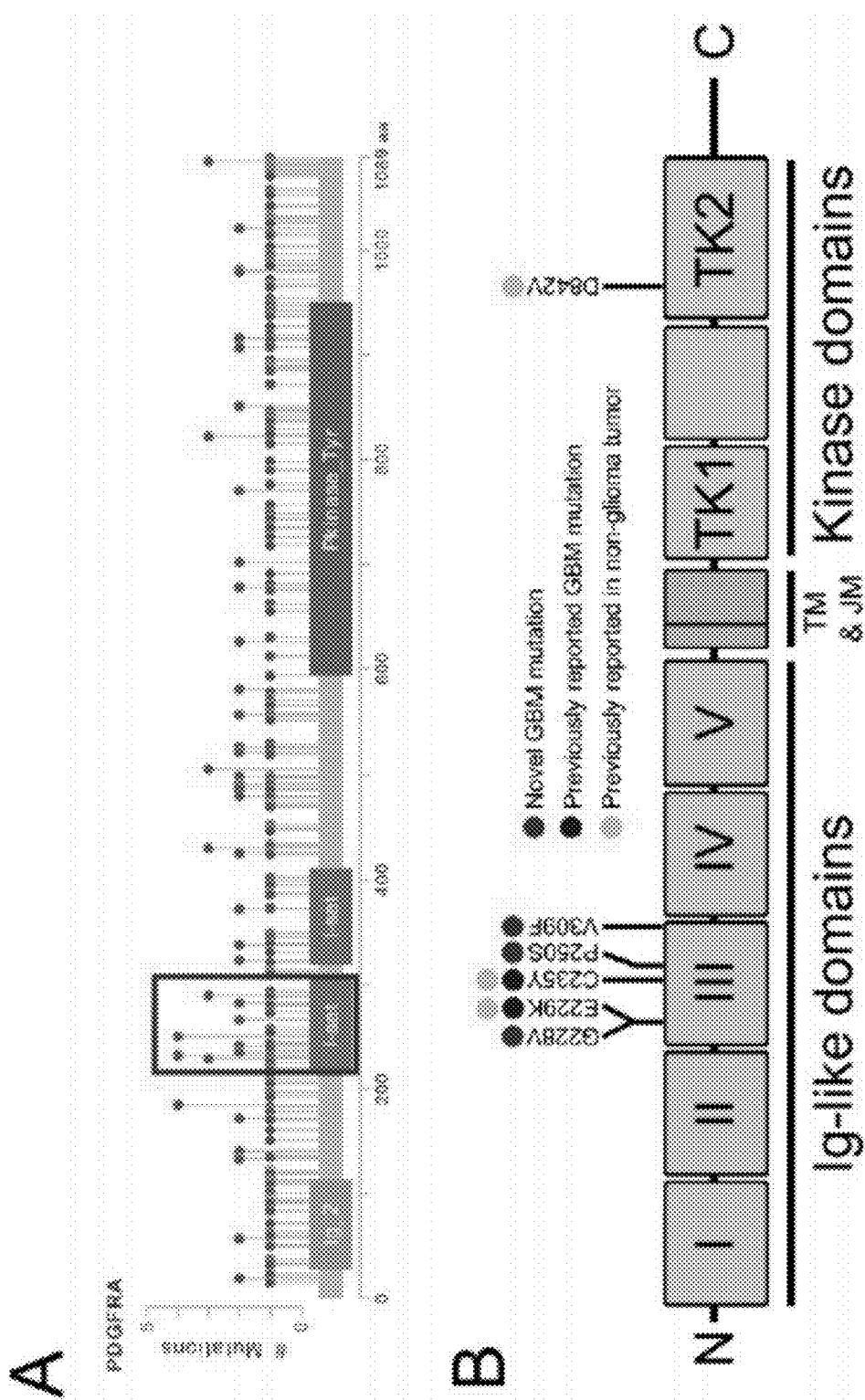
FIGS. 25A-25D: PDGFRA missense mutations in human cancers. (A) cBio Portal diagram of PDGFRA missense mutations in all currently available datasets. The third Ig-like domain is highlighted with a box. (B) Location of PDGFRA mutations. (C) Demonstration of FMEF cell line. FMEF cells were transduced with V5-tagged WT PDGFRA. Lines were serum starved overnight, then stimulated with PDGF-AA ligand for five minutes, then lysed and blotted. (D) Ligand sensitivity of extracellular mutations of PDGFRA. FMEF cells were transduced with indicated PDGFRA constructs, then serum starved overnight. Lines were stimulated with 5 ng/mL of PDGF-AA for five minutes, then lysed and blotted.
Figure 25C:
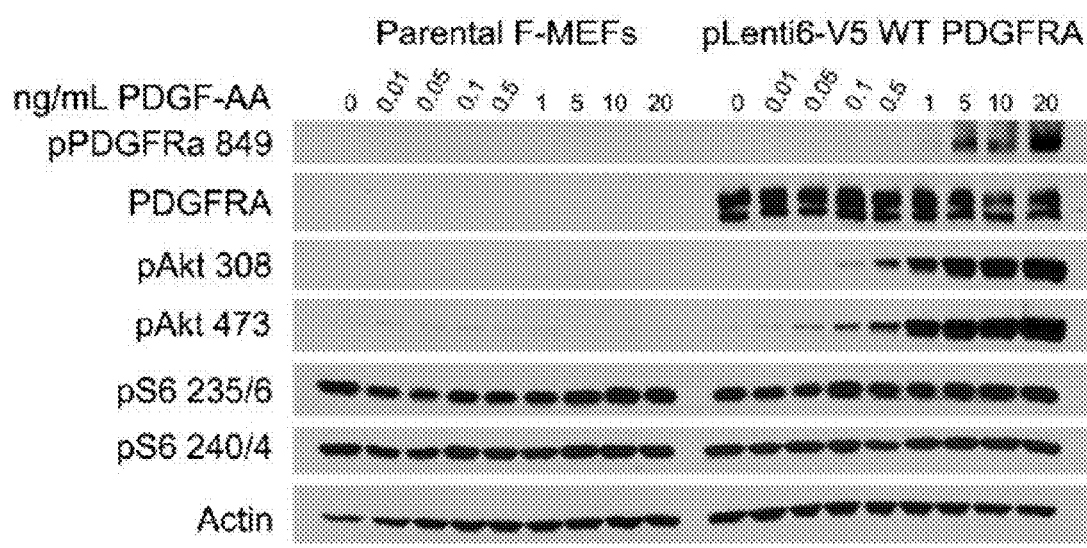
Figure 25D:
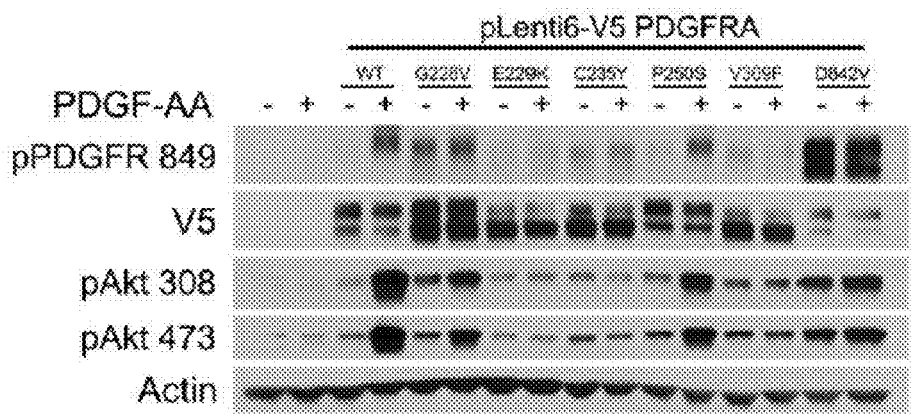

Based on sequencing efforts, data from the cBio portal, and mutations described (but uncategorized) previously (Paugh et al., 2013), an overview of PDGFRA mutations occurring in human cancers has been compiled. It was found that PDGFRA mutations in glioma tend to occur in the third IG-like domain of the extracellular portion of PDGFRA (amino acids 202-306) (FIGS. 25A and B). Mutations in this domain also occur sporadically in other cancer types, making this location the most frequent site for extracellular PDGFRA mutations. Several of these mutations (indicated in FIG. 25B) have been created and expressed in PDGFRA/PDGFRB null MEF cells, F-MEFs. These cells completely lack any response to PDGF ligand stimulation, unless a PDGFR is expressed (FIG. 25C). While the G228V mutation has ligand independent activity, much like the D842V mutation, and the P250S mutation seems to respond similarly to WT PDGFRA, the other mutations found in the extracellular domain do not have any ligand induced activity. In FMEF cells expressing E229K, C235Y, or V309F PDGFRA receptor phosphorylation was not detected nor any activation of any downstream members upon ligand stimulation. Sequence analysis of patients expressing these mutations shows that only a fraction (10-20%) of the PDGFRA receptor pool is mutant. Since PDGFRA signals as a dimer, aberrant activity of these mutations may only be revealed when expressed alongside WT PDGFRA. FMEF cells can be co-infected with both WT and mutant PDGFRA, or these mutations can be transduced into glioma lines with WT PDGFA such as S5472 or TS543.

Discussion.

Phase II clinical trials of novel agents for the treatment of glioblastoma typically use progression-free survival at 6 months as their primary endpoint. Extending patient survival and disease progression is the ultimate goal of all cancer therapeutics, but narrowly focusing on these outcomes may not be the best course of action for clinical trials of targeted therapies. Trials of agents which target rapidly dividing cells (such as chemotherapies or radiation treatment) are more easily generalizable to cancer patient populations, since it is fundamentally a disease of rapid unchecked cell growth. However, glioma can be a very heterogeneous disease both from patient to patient, and within a single tumor. Clinical trials which only examine tumor progression or survival may miss positive outcomes which occur in a fraction of patients. Treating glioblastoma has the added difficulty of drug delivery to the brain.

The trial described herein focused on pathway inhibition rather than patient outcomes. The tumor analysis revealed that measurable drug was getting to the tumor, and that the PI3K/mTOR pathway was inhibited in the majority of patients. Treatment with either a PI3K inhibitor or a dual PI3K did not result in feedback activation of PRAS40/Akt activity, which has been seen in patients treated with mTOR inhibitors (Cloughesy et al., 2008). In these studies, this reduction in PI3K pathway activation and cell proliferation did not result in a noticeable change in time to progression. Thus PI3K inhibition does not seem to be an effective treatment for the majority of glioma patients, despite pathway activation in most tumors (Brennan et al., 2013) and numerous studies demonstrating anti-proliferative and apoptotic effects of PI3K inhibitors in in vitro or in vivo models (Bagci-Onder et al., 2011; Koul et al., 2012; Liu et al., 2009; Prasad et al., 2011). However, in the present study, one outlier response (patient 2021) was observed. This patient had an amplified and mutated PDGFRA gene. This patient could represent a population of glioma patients who may benefit from treatment with PI3K inhibitors, mTOR inhibitors, or dual PI3K/mTOR inhibitors.

Despite the small number of patients in the clinical trial described here (n=21) and the low prevalence of PDGFRA amplification in adult GBM (5-10%) (Cerami et al., 2012), the approach indentified PDGFRA gene amplification as candidate marker of PI3K inhibitor sensitivity in GBM, a finding also confirmed in experimental model systems (see Example 2).

Example 2

Testing in Model Systems

The previous Example describes the results of a clinical trial of PI3K inhibitors in the treatment of human glioblastomas. Although the compounds were capable of reaching the tumor and inhibiting the PI3K/mTOR pathway, there was no noticeable change in the time to progression of the majority of patients. The only patient who responded to treatment was found to have mutations and genomic amplification of PDGRA, and this amplification was reduced after treatment with a dual PI3K/mTOR inhibitor SAR245409. The studies described in this Example examine the effects of inhibiting the PI3K/mTOR pathway in several in vitro and in vivo PDGFR driven models.

In Vitro Models of PDGFR Driven Cancer.

Figures 3A, 3B, 3C, 3D:
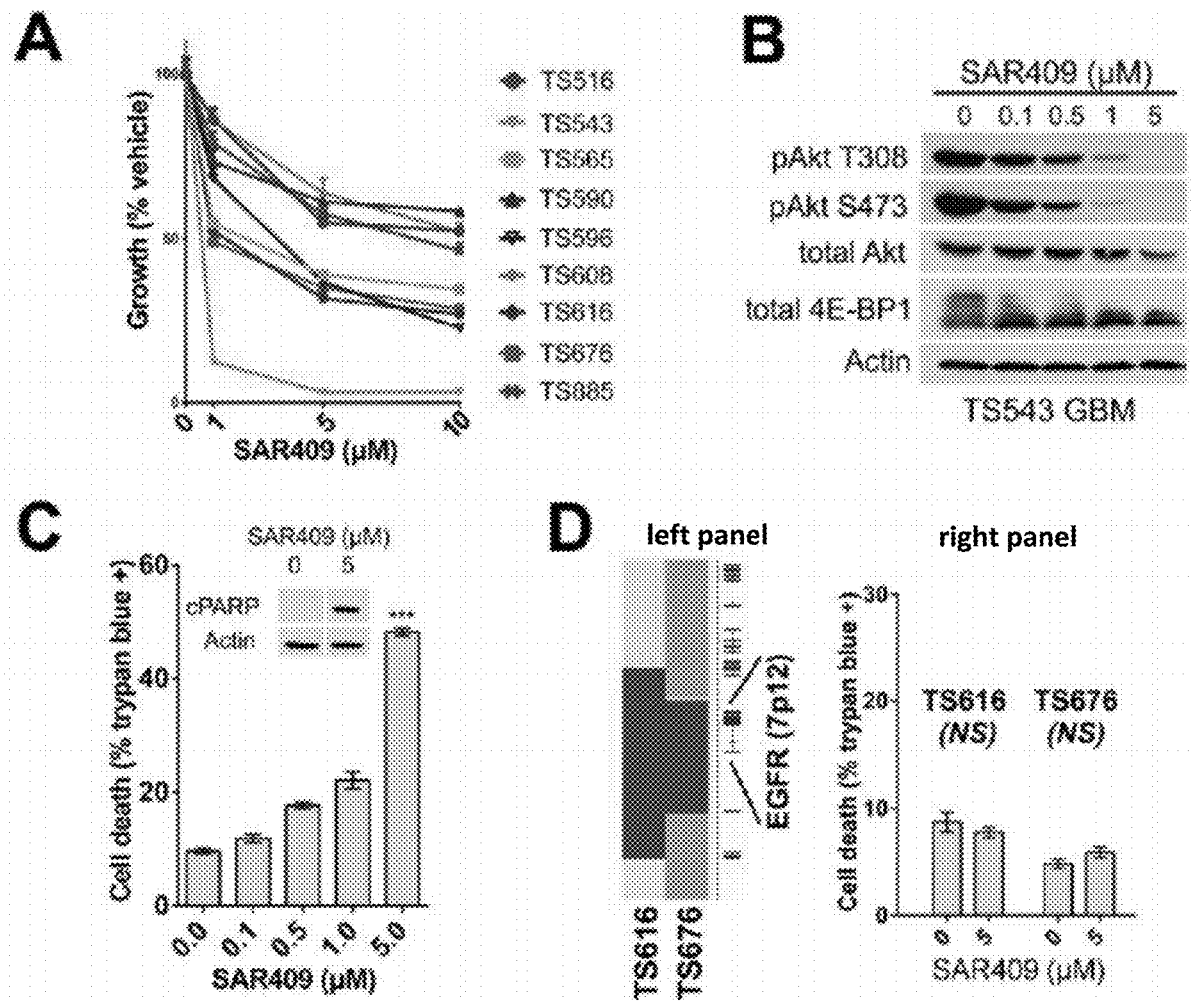
FIGS. 3A-3H: Dual PI3K/mTOR blockade induces death in GBM cells with PDGFR activation (A) Growth inhibition (% vehicle) of patient-derived GBM tumor spheres after five day treatment. Bars represent mean±SEM. TS543 GBM cells harbor PDGFRA gene amplification; TS516/TS596/TS608/TS616/TS676 harbor EGFR amplification; TS565/TS590/TS885 harbor NF-1 loss or mutation (B) Western Blot of TS543 GBM cells after four hour treatment with SAR409. (C) SAR409 induces cell death in PDGFRA-amplified TS543 GBM cells. % Trypan blue positive cells after five day drug treatment. Inset: Western Blot for cleaved PARP. (D) SAR409 does not induce cell death in EGFR-amplified GBM tumor sphere lines. Left panel, aCGH plots showing increased EGFR gene dosage in TS616 (log 2: 2.1) and TS676 (log 2:3.0) GBM cells. Right panel, % Trypan blue positive cells after five day treatment with SAR409 (5 µM). Graph depicts mean±SEM. (E) GDC-0980 inhibits PI3K/mTOR signaling (left panel) and tumor cell proliferation (middle panel) in TS543 GBM cells and induces cell death (right panel). Experimental conditions were as described under panel A. (F) Doxycyline-regulated expression of PDGF-B expression in S5472 GBM cells. See Examples for details. Left panel, doxycyline turns off PDGFB transgene expression in S472 GBM cells. Middle panel, Western Blot of S5472 cells following 48 hour treatment with doxycycline (0.5 ng/mL). Right panel, % Trypan blue positive S5472 cells after five day treatment with doxycycline. (G) Dual PI3K/mTOR blockade with SAR409 and GDC-0980 results in dose-dependent PI3K inhibition and cell death in S5472 GBM cells. Left and middle panels, % Trypan blue positive S5472 cells after five day treatment with the indicated drug (mean±SEM). Right panel, Western Blot after four hour drug treatment. (H) SAR409 inhibits growth of PDGF-B-induced gliomas in mice. Left panel, cartoon of experimental design (see Examples for details). Right panel, fold change in MRI-based tumor volume between the start and end of treatment with vehicle (n=9) or 60 mg/kg/day SAR409 (n=8) (p=0.006, unpaired t-test with Welch's correction, error bars indicate SEM). p-values are as indicated: p≤0.01, *p≤0.001, ****p≤0.0001, NS: not significant.
Figures 3E, 3F:
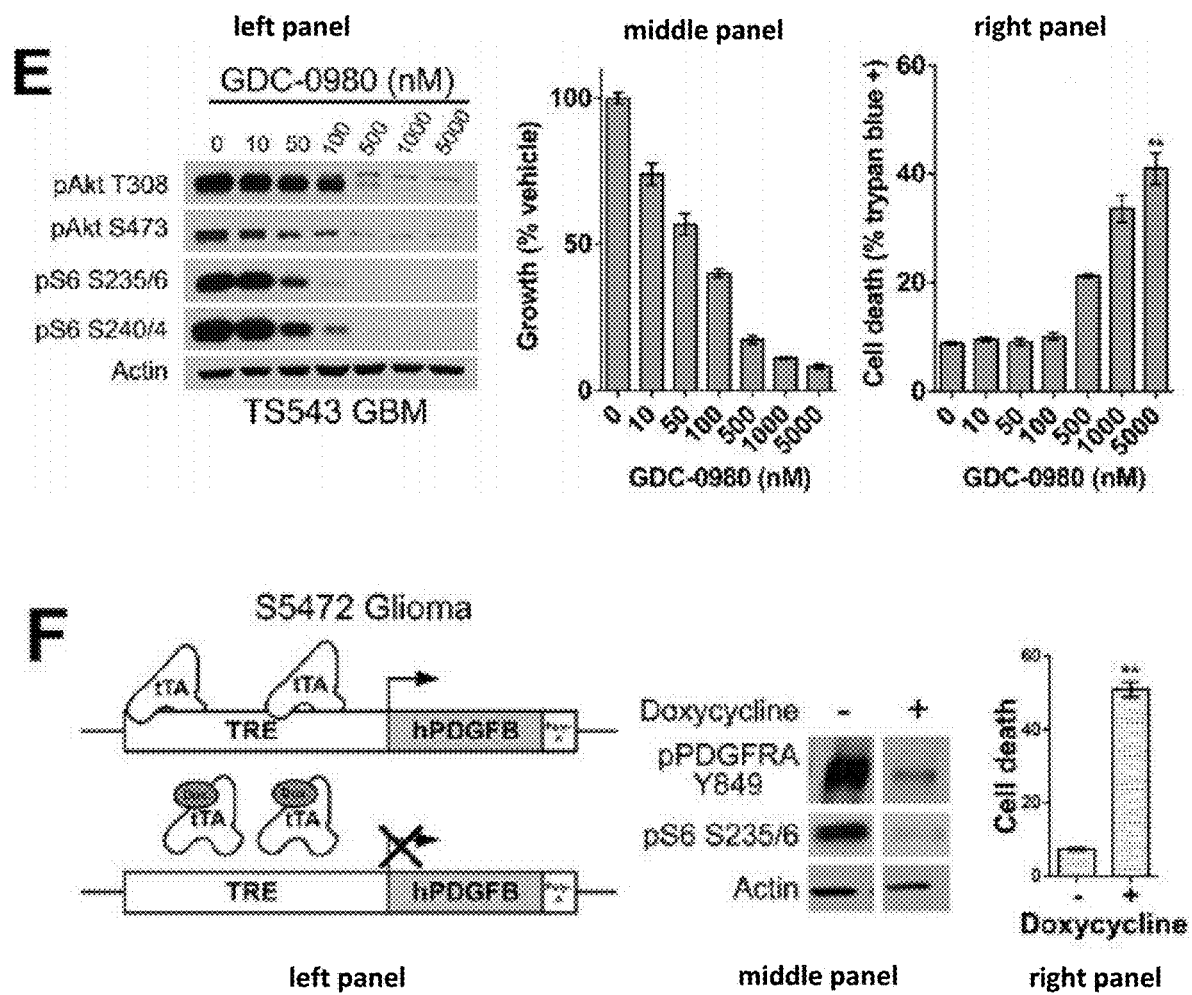
Figures 9A, 9B, 9C:
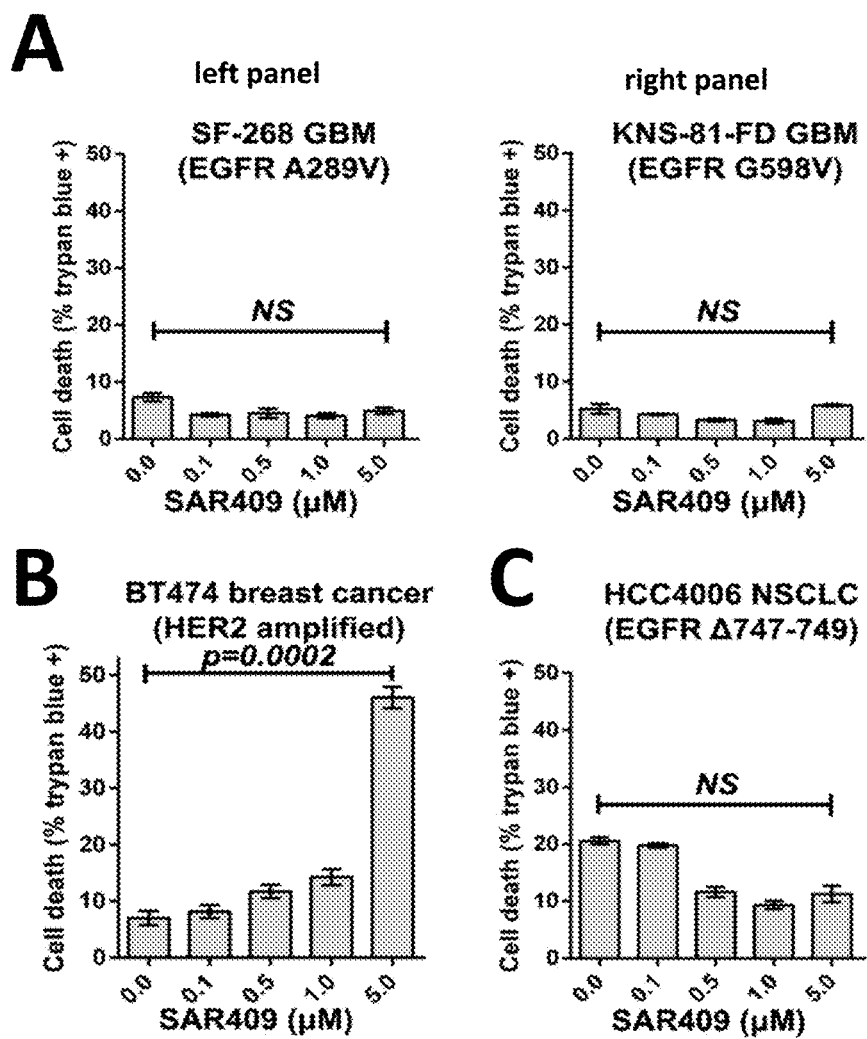
FIG. 9A-9D: PDGFRA-amplified, but not EGFR mutant cancer cell lines undergo cell death in response to PI3K/mTOR blockade. The graphs show % Trypan blue positive cells after five day SAR409 treatment. All graphs depict mean values±SEM. (A) EGFR mutant GBM cells (left panel, SF-268: EGFR A289V; right panel, KNS-81-FD: EGFR G598V). (B) HER2-amplified BT-474 breast cancer cells (C) EGFR-mutant (EGFRΔ747-749) HCC4006 human non-small cell lung cancer cells. (D) PDGFRA amplified H1703 human non-small cell lung cancer cells. The upper panel shows copy gain at the PDGFRA gene locus by array-CGH, as previously reported (Holland et al., 1998). The graphs show % Trypan blue positive cells after five day treatment with the PI3K/mTOR inhibitors SAR409 (left panel) or GDC-0980 (right panel). The inset shows Western Blots of H1703 whole cell lysates after 36 hours of treatment with SAR409 (5 µM).
Figure 9D:
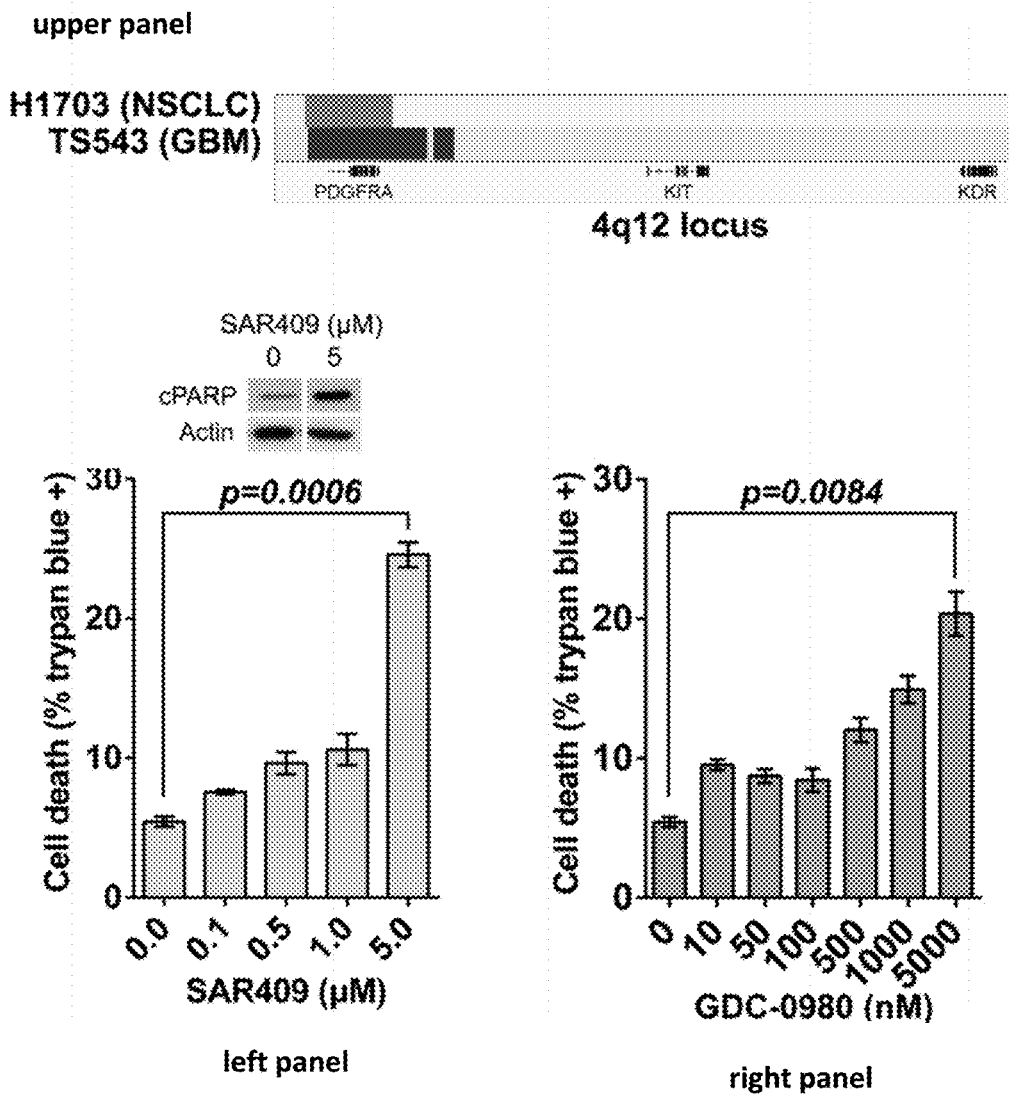
Figures 13A, 13B:
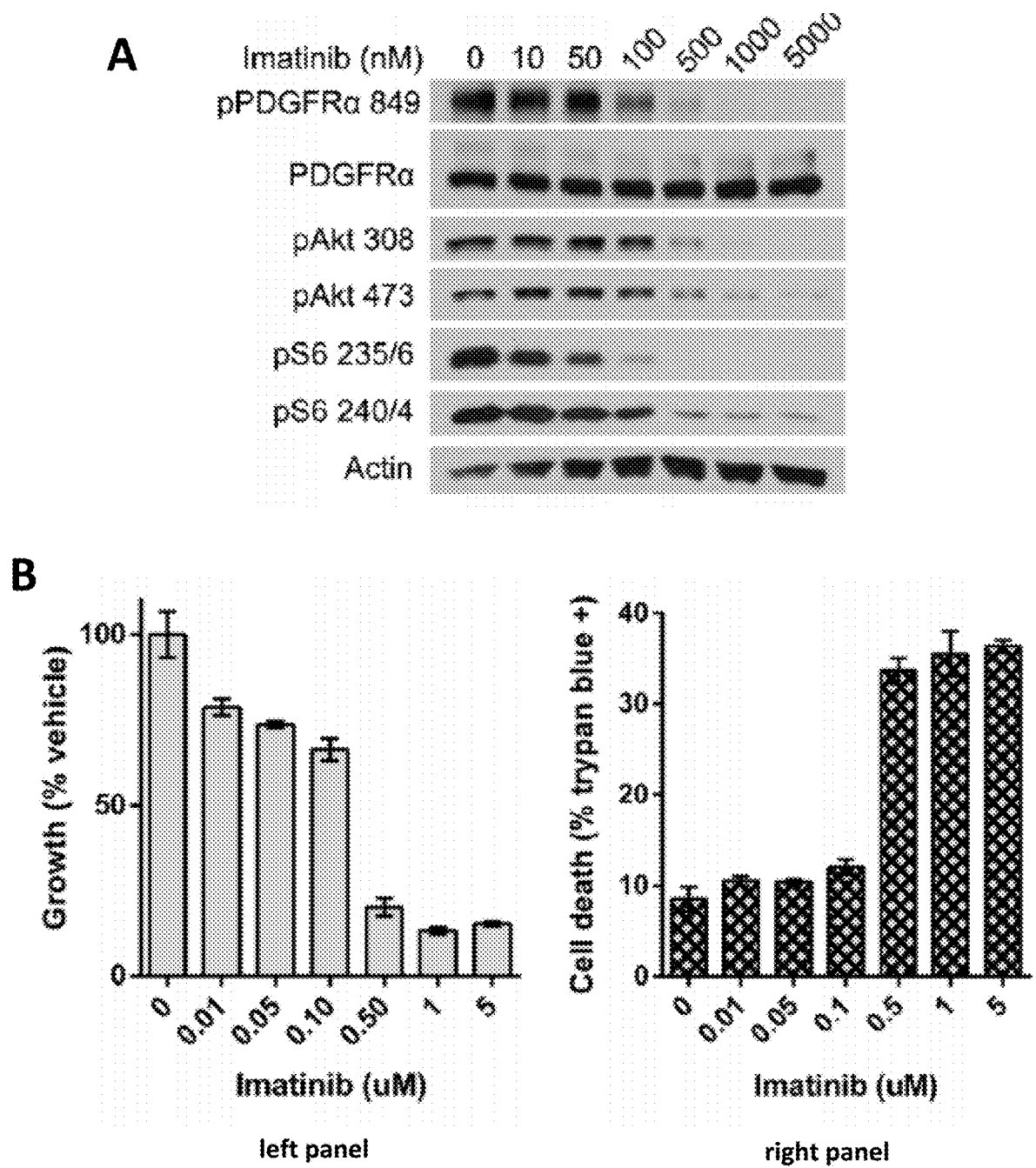
FIGS. 13A-13B: TS543 is a PDGFRA amplified and addicted neurosphere line. (A) Imatinib treatment inhibits PDGFRA and downstream signaling. (B) Cells were treated with drug for five days, then analyzed for proliferation (left panel) and death (right panel). Graphs depict average±standard error of the mean (SEM).
Figure 14:
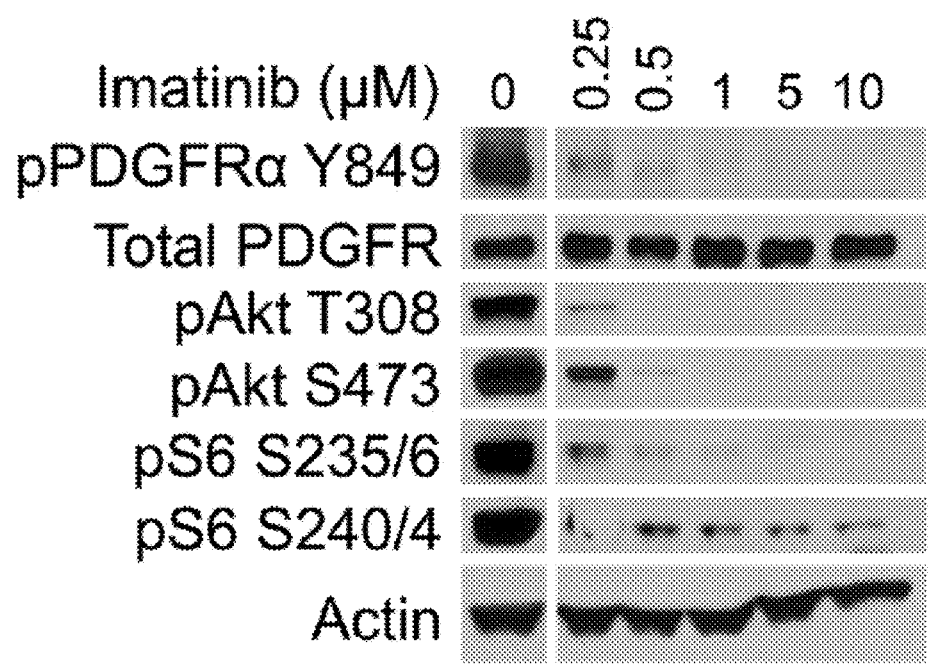
FIG. 14: H1703 is a PDGFRA amplified driven line. H1703 cells were treated with imatinib for 4 hours, then lysed and blotted with indicated antibodies.
Figure 15A:
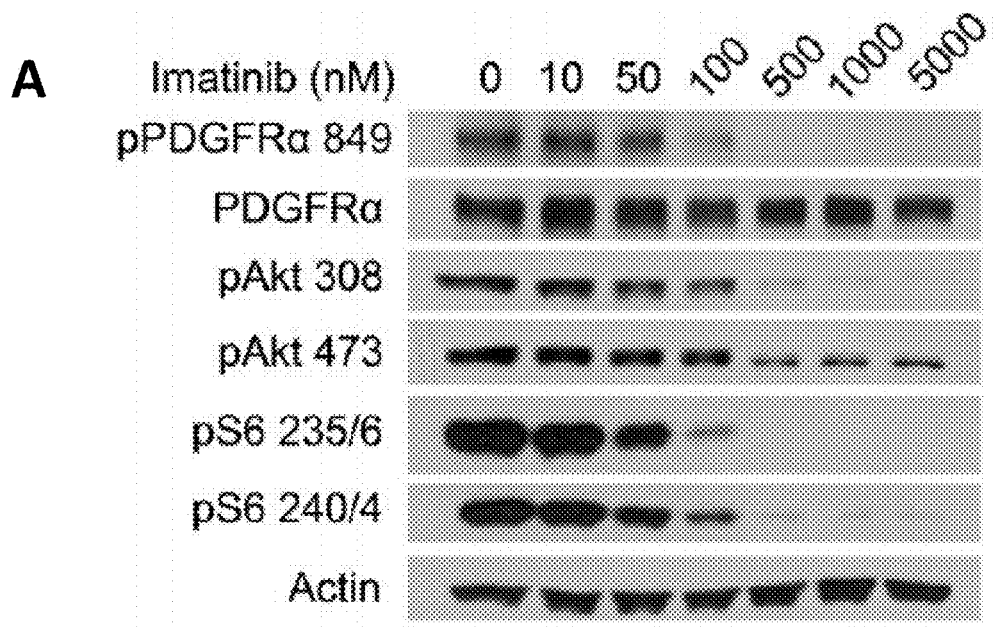
FIGS. 15A-15B: S5472 is a PDGF ligand driven model of glioma. (A) Imatinib treatment inhibits PDGFRA and downstream signaling. Cells were treated with imatinib for four hours, then lysed and blotted for designated proteins. (B) Imatinib inhibits cell growth (left panel) and induces cell death (right panel) in S5472 cells. Cells were treated with drug for five days, then analyzed. Graphs depict average±SEM.
Figure 15B:
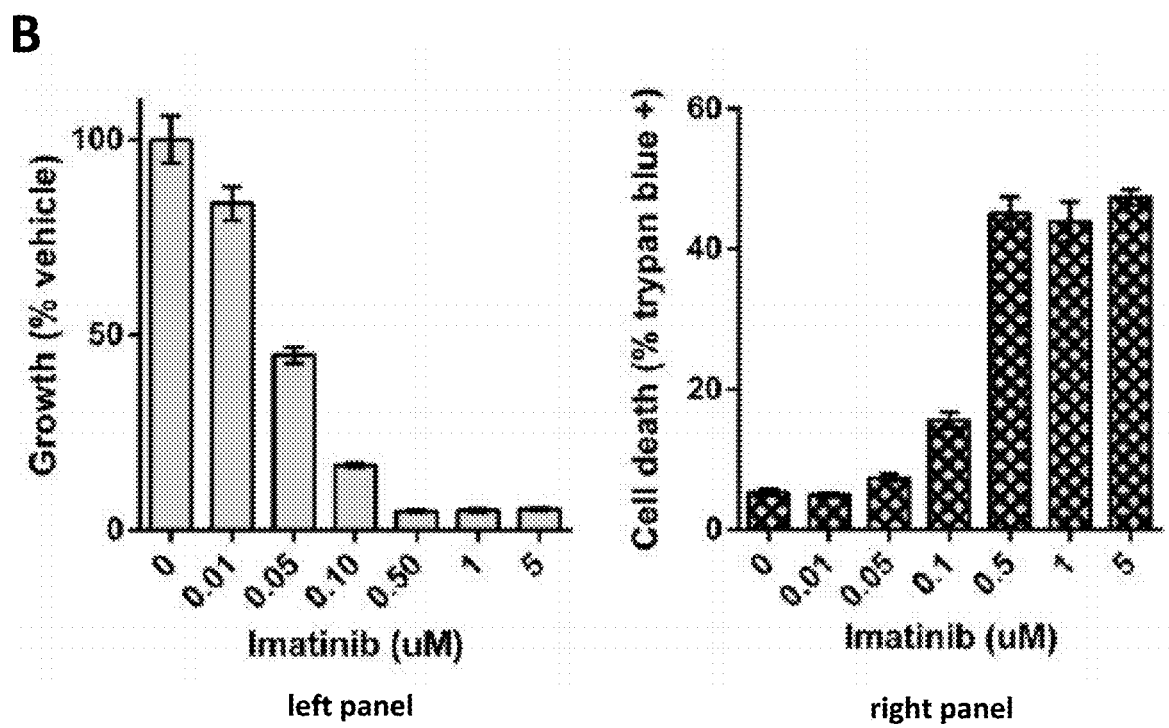

The cell line TS543 has amplified PDGFRA (FIG. 9D) and is addicted to PDGFRA signaling. When PDGFRA signaling is inhibited using imatinib (a PDGFRA inhibitor) a robust induction of cell death is seen (FIGS. 13A and 13B). The H1703 cell line is derived from a non-small cell lung cancer (NSCLC) tumor. It has genetic gain of PDGFRA (FIG. 9D, upper panel). It was noted in a screen for sunitinib sensitive lines that H1703 is sensitive to both sunitinib and imatinib inhibition (McDermott et al., 2009). Treatment of H1703 with imatinib results in robust inhibition of PGDFRA and downstream signaling (FIG. 14). S5472 cells were derived from a mouse model of glioma (Hitoshi et al., 2008). A mouse line expressing doxycycline (dox) repressible human PDGFB was crossed with a GFAP/tTA line to create a mouse line with PDGFB expression in GFAP positive cells of the brain (FIG. 3F, left panel). If not treated with dox, these mice quickly succumb to tumors of the spinal cord and brain. S5472 is a cell line derived from a brain tumor which formed in one of these transgenic mice. It is addicted to PDGFB and dies when given dox (FIG. 3F). It is also sensitive to inhibition of PDGFR and will die when treated with imatinib (FIGS. 15A-15B).

The data in Example 1 demonstrated that PDGFRA amplified GBM cells may be more sensitive to PI3K pathway blockade than GBM cells harboring other lesions in the PI3K pathway. This was tested using a panel of patient-derived GBM tumor spheres and other human cancer cell lines. TS543 GBM cells, which harbor a PDGFRA gene amplification and an oncogenic in-frame-deletion of the PDGFRA extracellular domain (Clarke and Dirks, 2003; Ozawa et al., 2010), were more sensitive to growth inhibition by SAR409 than GBM tumor sphere lines with inactivation of neurofibromin-1 (NF1) or EGFR gene amplification (FIG. 3A). At concentrations that inhibited the PI3K/mTOR pathway almost completely (FIG. 3B), SAR409 induced cell death in TS543 cells (FIG. 3C). SAR409 failed to induce cell death in EGFR amplified (FIG. 3D) or EGFR mutant (FIG. 9A) GBM cells. SAR409 induced cell death in HER2-amplified BT474 breast cancer cells (FIG. 9B), but not EGFR mutant lung cancer cells (FIG. 9C), consistent with the reported activity of other PI3K pathway inhibitors in the latter two cell lines (She et al., 2008; Faber et al., 2009). Similar to these findings with SAR409, the dual PI3K/mTOR inhibitor GDC-0980 (Wallin et al., 2011) induced dose dependent cell death in PDGFRA-amplified TS543 GBM cells (FIG. 3E) and PDGFRA-amplified H1703 human lung cancer cells (FIG. 9D).

Figures 16A, 16B, 16C, 16D:
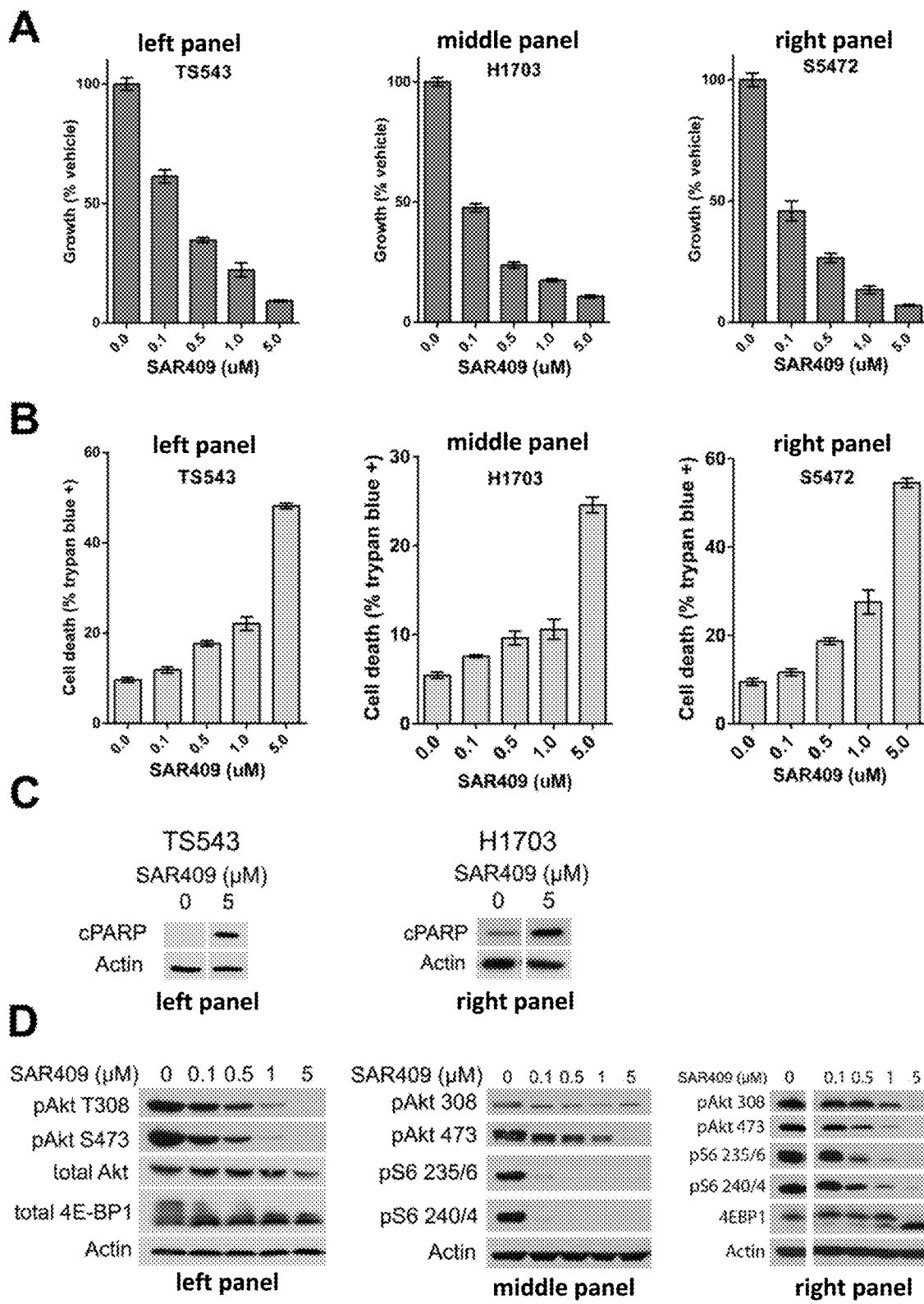
FIGS. 16A-16D: SAR245409 induces proliferation arrest and cell death in PDGFR driven cell lines. (A) Cells were treated with SAR245409 for five days then assayed for proliferation. Left panel, TS543; middle panel, H1703; right panel, S5472. Graph depicts average±SEM. (B) In the same assay as panel A, cells were analyzed for induction of cell death. Left panel, TS543; middle panel, H1703; right panel, S5472. Graph depicts average±SEM. (C) Cells were treated with SAR245409 for 12 hours (left panel, TS543) or 36 hours (right panel, H1703), then lysed and blotted with indicated antibodies. (D) Lines were treated with SAR245409 for 4 hours, then lysed and blotted with designated antibodies. Left panel, TS543; middle panel, H1703; right panel, S5472.

To address whether the amplification of PDGFRA detected in patient #2021 in the clinical trial (see Example 1, above) is a sensitizing lesion for inhibition with SAR245409, two PDGFRA amplified lines (TS543 and H1703) and a PDGFB driven line (S5472) were tested. Treatment of these lines with inhibitors of PDGFR activity resulted in robust inhibition of the PI3K/mTOR pathway, indicating that the PI3K pathway may be the main means by which these lines drive their growth and survival. The three lines were then treated with SAR245409 and changes in cell proliferation and survival were examined. Treatment with SAR245409 caused potent growth inhibition and induction of cell death (FIGS. 16A and 16B) in all three lines. This cell death was apoptotic in nature (FIG. 16C). Inhibition of the PI3K/mTOR pathway correlated with the induction of cell death (FIG. 16D).

Figure 17A:
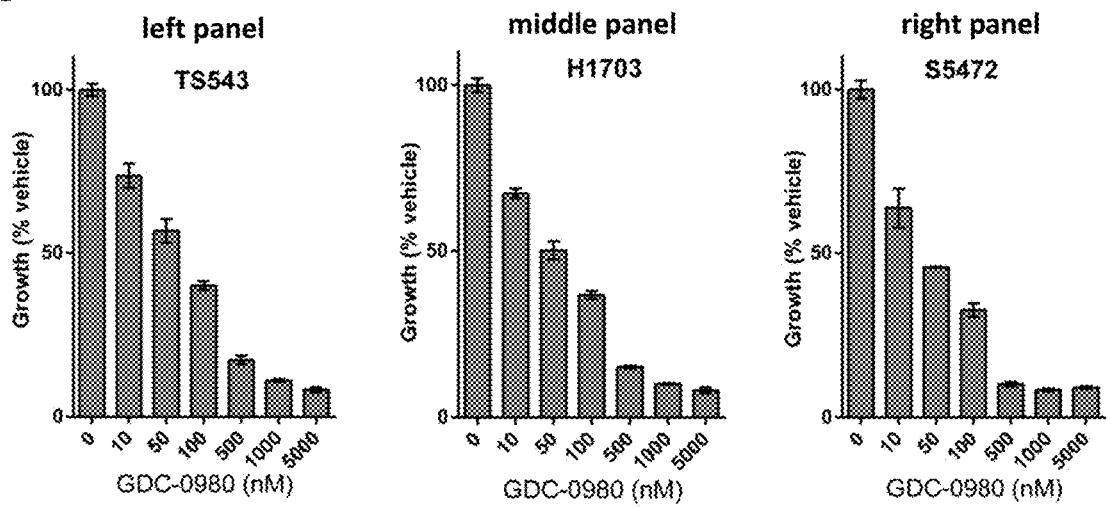
FIGS. 17A-17C: GDC-0980 induces proliferation arrest and cell death in PDGFR driven cell lines. (A) Cells were treated with SAR245409 for five days then assayed for proliferation. Left panel, TS543; middle panel, H1703; right panel, S5472. Graph depicts average±SEM. (B) In the same assay as panel A, cells were analyzed for induction of cell death. Left panel, TS543; middle panel, H1703; right panel, S5472. Graph depicts average±SEM. (C) Lines were treated with GDC-0980 for 4 hours, then lysed and blotted with depicted antibodies. Left panel, TS543; middle panel, H1703; right panel, S5472.
Figure 17B:
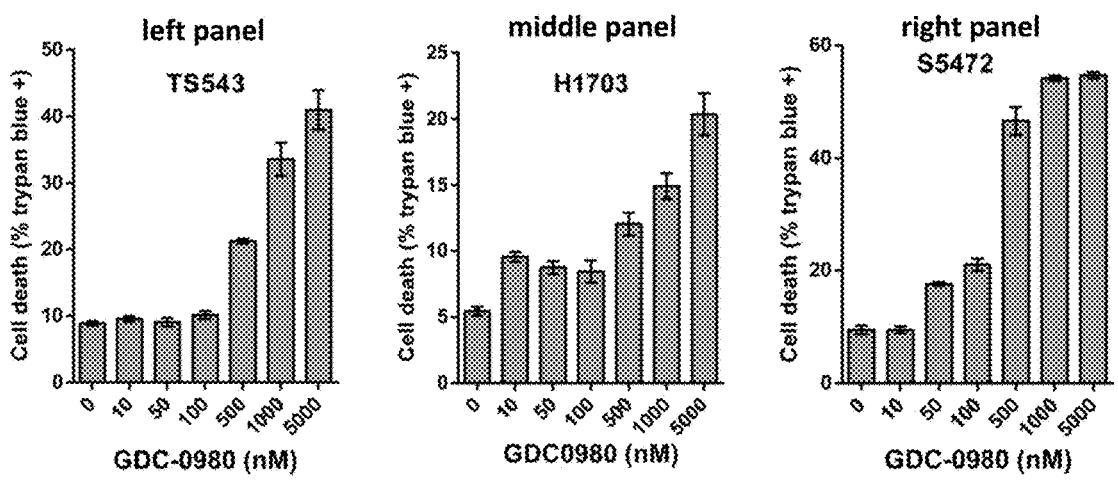
Figure 17C:
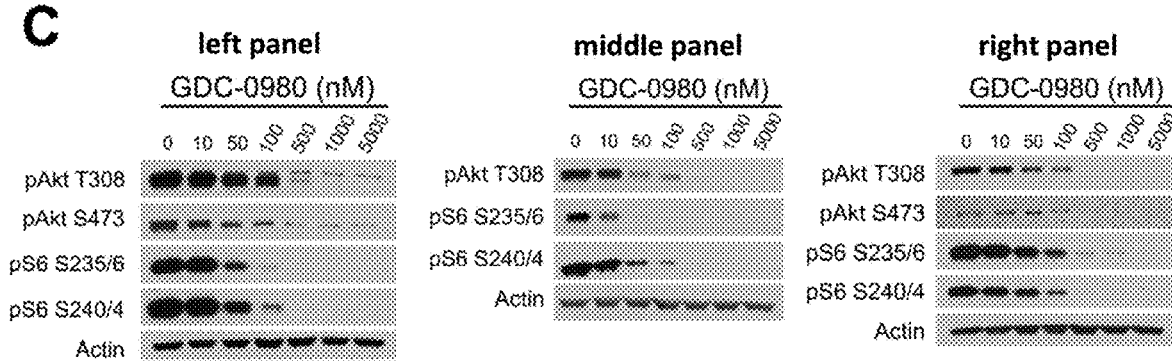

With any small molecular therapy there are questions of how precisely the agent is targeted and if the biological effects noted are due to its on target or off target effects. To address this, TS543, H1703, and S5472 cells were treated with an alternative dual Class I PI3K/mTOR inhibitor GDC-0980 (for IC50 information for this compound see Table 2 in Example 1). Similar to SAR245409 treatment, inhibition of proliferation (FIG. 17A) and induction of cell death (FIG. 17B) was detected. These biological effects correlated with the degree of pathway inhibition (FIG. 17C).

Figure 3G:
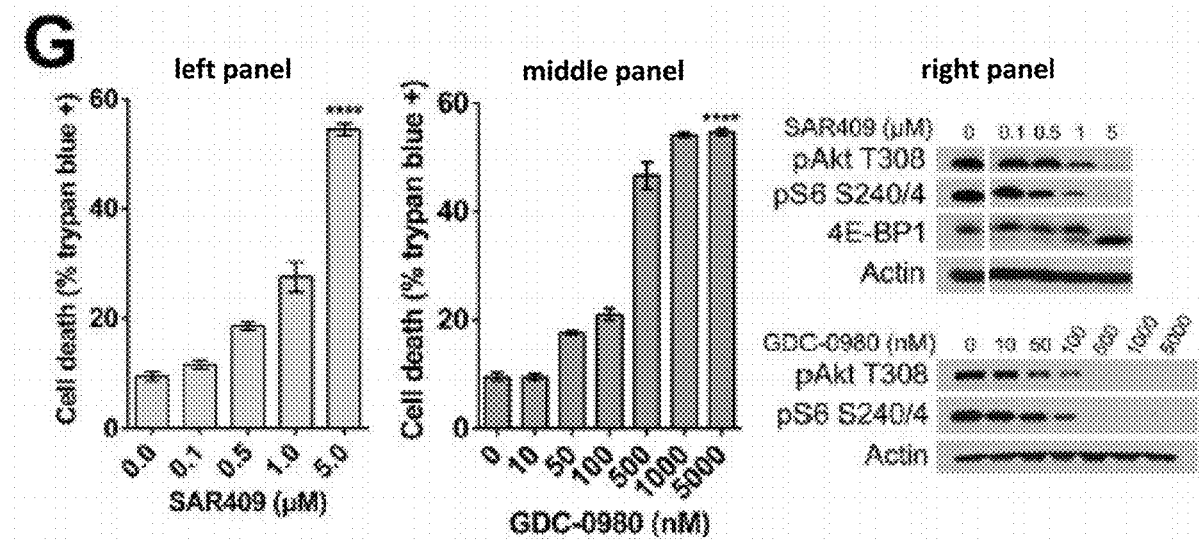

Aberrant activation of PDGFRA in cancer can result from overproduction of its cognate ligands (Heldin et al., 2012). Studies were conducted to determine whether GBM cells that were transformed through a PDGFR ligand required PI3K/mTOR signals for survival as had been observed with PDGFRA-amplified GBM cells. This question was addressed using S5472 cells which are derived from an intracranial GBM in mice with doxycycline-regulated expression of PDGF-B in neural stem cells (Hitoshi et al., 2008). Treatment of these cells with doxycycline blocks PDGF-B expression, abrogates PDGFR phosphorylation, and induces cell death (FIG. 3F). Both PI3K/mTOR inhibitors (SAR409, GDC-0980) induced cell death at levels of near complete PI3K pathway inhibition (FIG. 3G).

All of the PDGFR driven cell lines examined required PI3K/mTOR pathway activity for growth and survival.

In Vivo Models of PDGFR Driven Cancer.

Figure 18:
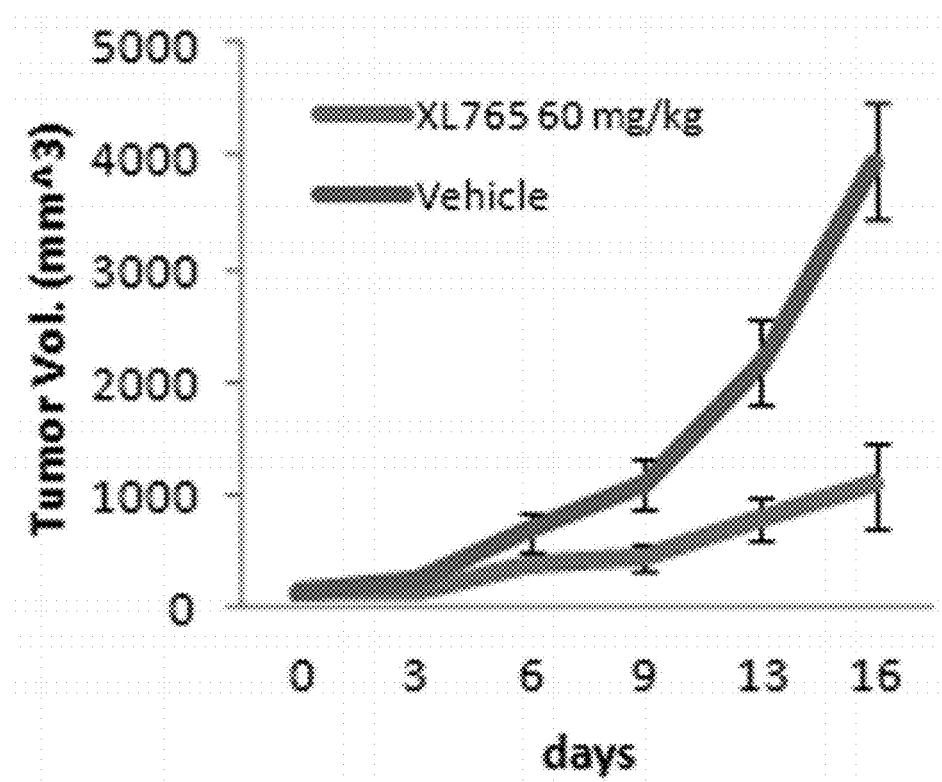
FIG. 18: In vivo subcutaneous model of TS543 treated with SAR245409. One million cells were injected into SCID mice. After palpable tumors formed, mice were randomized into either vehicle or treatment groups. Graph is average measured tumor volume±SEM.

To confirm the in vitro observations described above in vivo, one million TS543 cells were injected into the flank of a severe combined immune deficiency (SCID) mouse. Once tumors had formed, the mice were randomized into vehicle or 60 mg/kg/day SAR245409 treatment arms. Tumors were measured every three days. Mice treated with SAR245409 saw a marked reduction in tumor growth (FIG. 18). This reduction was statistically significant (unpaired t test with Welch's correction, p=0.0139).

Figure 19A:
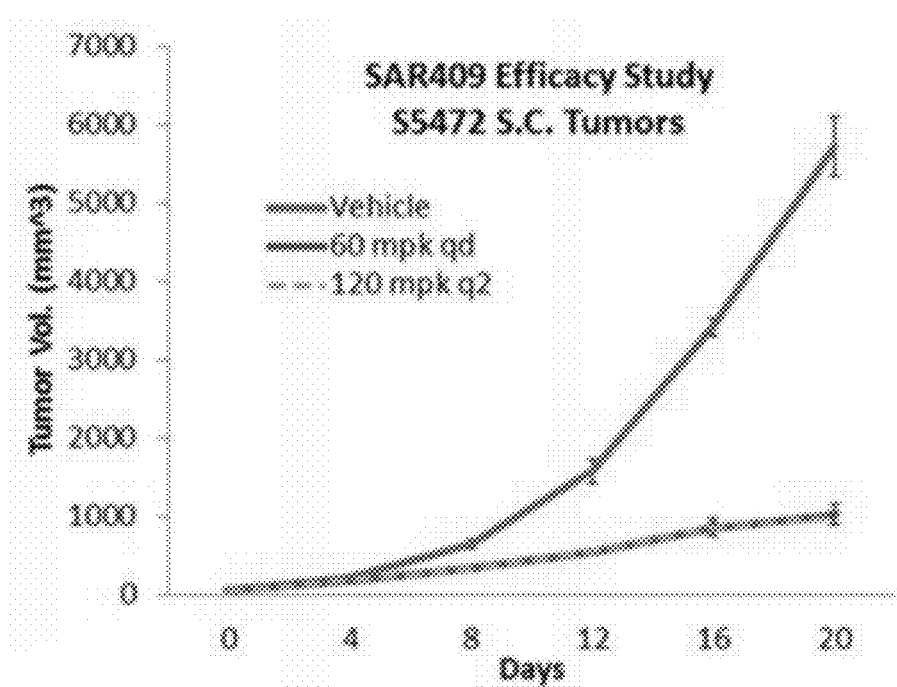
FIGS. 19A-19B: Only pathway and tumor growth is inhibited with in vivo SAR245409 treatment of S5472. (A) In vivo tumor growth assay of S5472 cells treated with SAR245409. Tumors were treated with vehicle, 60 mg/kg/day, or 120 mg/kg/every other day SAR245409. Graph depicts average tumor volume measurements±SEM (n=10 for each arm). (B) Electrochemiluminescent of phosphoproteins in S5472 tumor lysates. Tumor sections were lysed and assayed using the Meso Scale assay system for pAkt Ser473 (left panel) or pS6 Ser240/4 (right panel). Measurements are in chemical luminescence values. Treatment groups are statistically significantly lower than vehicle treated animals (p=0.0001, unpaired t-test with Welch's correction).
Figure 19B:
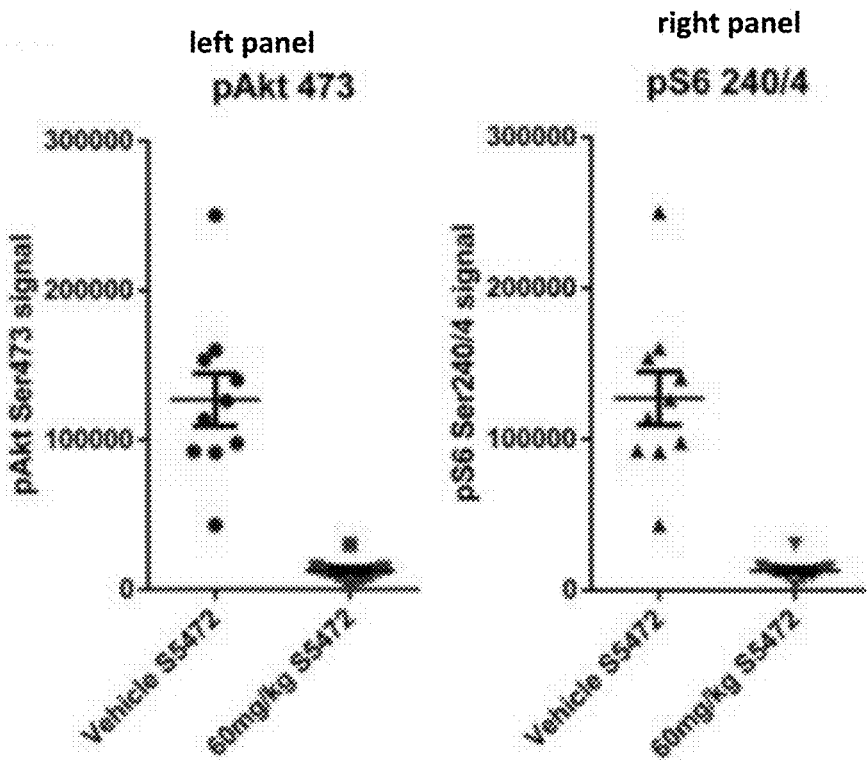

The in vivo effects of SAR245409 treatment were examined on the S5472 PDGF-β driven line. One million S5472 cells were injected subcutaneously into SCID mice flanks. After measurable tumor formation, mice were randomized into vehicle, 60 mg/kg/day, or 120 mg/kg/every other day treatment groups, ten mice per group. SAR245409 treatment markedly reduced tumor growth compared to vehicle treated animals. Both treatment groups of SAR245409 equally inhibited tumor growth (FIG. 19A). Tumors were removed from one hour after the last dose of treatment for analysis. Sections were IHC stained for biomarkers of pathway inhibition pAkt Ser473 and pS6 Ser235/6. Notable inhibition of both markers was present in the treated animals compared to vehicle controls, determined by IHC S5472 tumors carried out by sacrificing mice one hour after last dose of drug, and staining tumor sections were stained for pAkt Ser473 or pS6 Ser235/6. Portions of the tumor were lysed and pAkt Ser473 and pS6 Ser240/4 were measured using an electrochemiluminescent assay on the Meso Scale system (FIG. 19B). In the 60 mg/kg/day treatment arm levels of both phospoproteins were significantly down compared to vehicle treated tumors (both tests p=0.0001, unpaired t-test with Welch's correction).

Figure 3H:
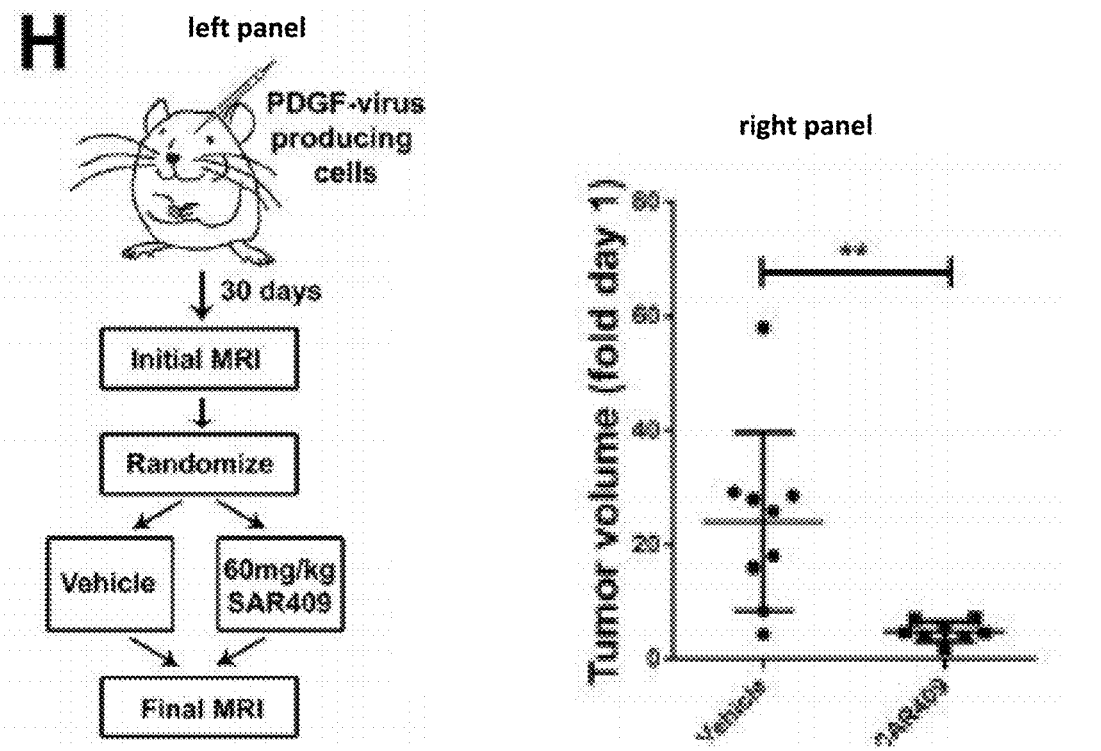

SAR409 also impaired the in-vivo growth of orthotopic gliomas induced by PDGF-B using the replication competent ALV splice acceptor (RCAS)/tv-a system. The replication-competent avian sarcoma-leukosis virus long terminal repeat with splice acceptor/tumor virus A (RCAS/tv-a) system allows for infection of specific cell populations in mice or other mammalian systems. Only cells expressing the tv-a receptor can be infected with avian RCAS type retroviruses. In mice, one can drive expression of the tv-a receptor under cell lineage specific promoters. The effects of SAR245409 inhibition were tested in an RCAS mouse glioma model. Ink4a/Arf−/− mice with tv-a expression driven by the brain specific nestin promoter were infected by intercranially injecting RCAS-human-PDGFB virus producing cells. Thirty days was allowed for tumor formation to initiate then all mice were imaged with an MRI. Mice with tumors evident were randomized into vehicle (n=9) or 60/mg/kg/day SAR245409 (n=8) treatment groups. After ten days of treatment tumors were measured by MRI again, and mice were sacrificed one hour after the last dose of compound. The initial and final sizes of the tumors in the vehicle and SAR245409 treated groups were compared and a fold growth was derived for each tumor. The fold change in tumor size in the SAR245409 treated group was statistically significantly smaller than that of the vehicle treatment group (FIG. 3H, right panel, p=0.006). IHC analysis of biomarkers of the PI3K/mTOR pathway (IHC pS6 Ser235/6 staining) revealed reduced activation in mice treated with SAR245409. Tumors in mice treated with SAR409 grew markedly slower and showed reduced staining with an antibody against phospho-S6 RP, documenting effective pathway blockade by SAR409 in this orthotopic glioma model.

SAR245409 Induces Proliferation Arrest but not Apoptosis in Glioma without PDGFR Alterations.

Figures 20A, 20B:
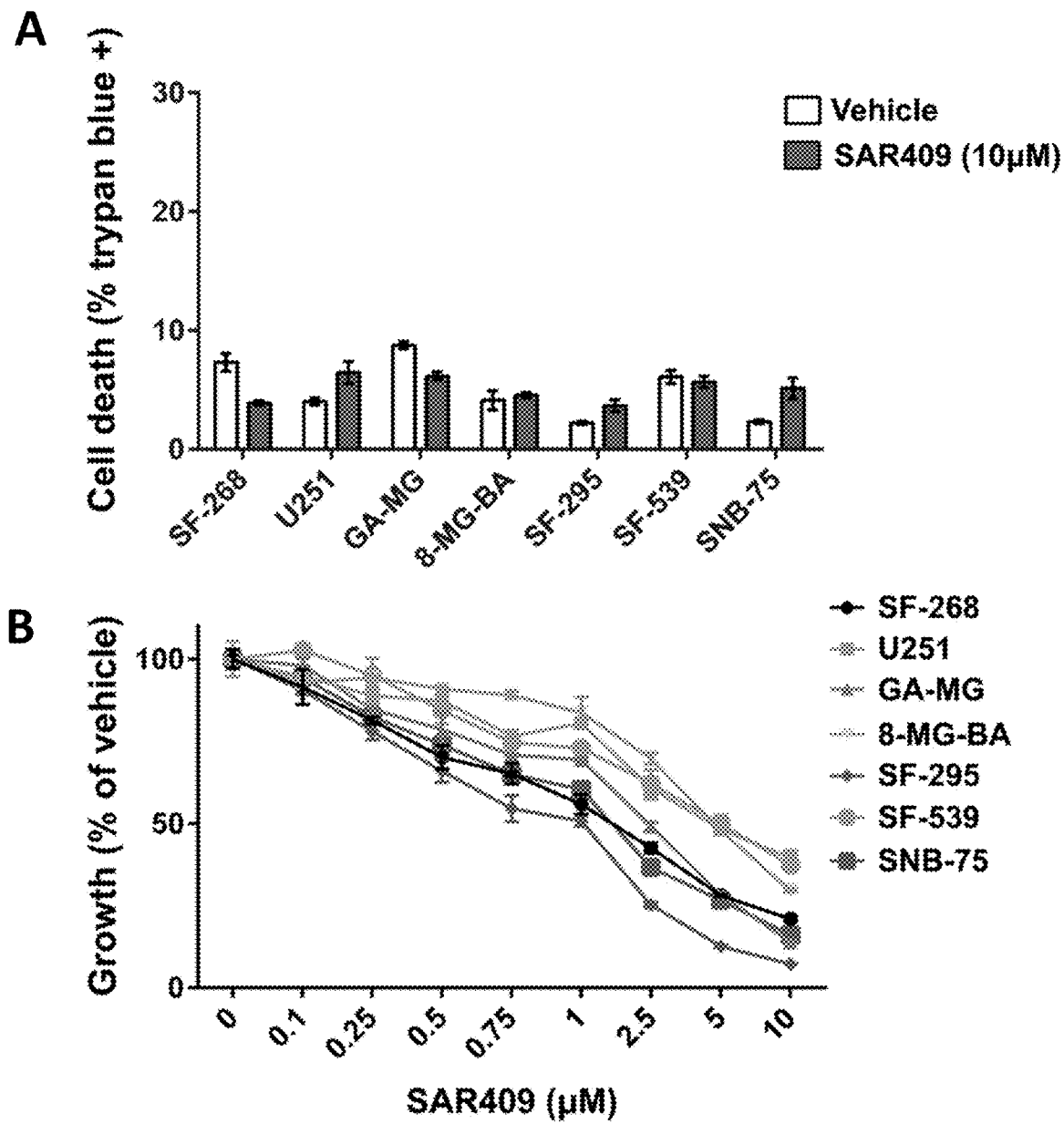
FIGS. 20A-20B: SAR245409 does not induce cell death in glioma lines without PDGFRA alterations. Cells were treated with SAR245409 for five days then analyzed for induction of cell death (A) and proliferation (B). Graphs depict mean±SEM.

The response of patient #2021 to SAR245409 (see Example 1) could be generalized to other PDGFR driven cell lines, as described above. To ensure that these cell line observations were not simply indiscriminant in vitro responses, a panel of glioma cell lines without any alterations in PDGFRA was assembled and their response to dual PI3K/mTOR inhibition was tested. Although all lines were growth inhibited by SAR245409 (FIG. 20B), there was little to no induction of cell death in these lines (FIG. 20A).

Figures 21A, 21B, 21C:
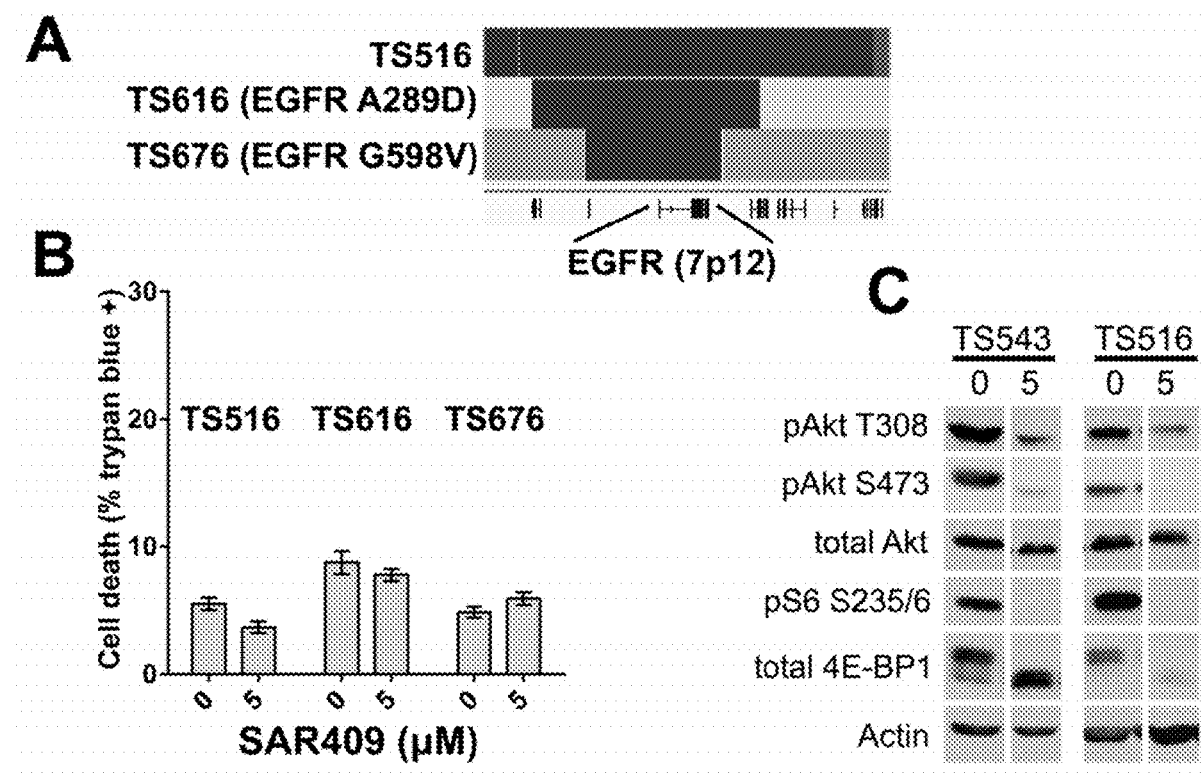
FIGS. 21A-21C: SAR245409 does not induce cell death in EGFR altered glioma lines. (A) aCGH analysis of the EGFR gene locus. Amplification is present in TS516 ($log_2$ ratio=2.7897) TS616 ($log_2$ ratio=2.1068) and TS676 ($log_2$ ratio=2.9697). (B) Cells were treated with SAR245409 for five days, then analyzed for induction of cell death. (C) Cells were treated with 5 µM SAR245409 for four hours, then lysed and blotted with indicated antibodies.

Next a panel of EGFR altered primary human neurosphere lines was examined. All lines had amplification of EGFR by aCGH, and two had point mutations in the extracellular domains: the TS616 line has a A289D mutation, and the TS676 line has a G598V mutation (FIG. 21A). SAR245409 treatment induced proliferation arrest, but not cell death induction in these lines (FIG. 21B). This is despite inhibition of the pathway to a similar degree as a PDGFRA driven primary glioma line, TS543 (FIG. 21C).

EGFR is the most commonly altered RTK in glioblastoma, over 50% of patients have either a mutation or amplification of the gene. To confirm the observation that cell lines with EGFR mutations do not rely on the PI3K/mTOR pathway for survival, three additional lines with EGFR mutations were treated: SF-268 (a glioma line with an A289V mutation), KNS-81-FD (a glioma line with the G598V mutation), and HCC4006 (a NSCLC line with a small in-frame deletion EGFRΔ747-749). A HER2 amplified breast cancer line, BT474, was also treated as a positive control. HER2 amplification has been shown to be a marker of sensitivity to PI3K and Akt inhibition (She et al., 2008). When these lines were treated with SAR245409, robust induction of cell death was only detected in the BT474 line (FIG. 9B).

mTOR Inhibition is not Sufficient to Induce Cell Death in PDGFRA Driven Lines.

Figure 22A:
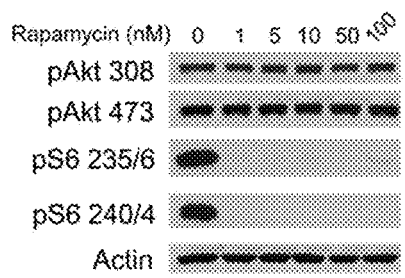
FIGS. 22A-22D: Inhibition of TORC1 and TORC2 result in proliferation arrest but not apoptosis in PDGFR driven lines. (A) TS543 was treated with rapamycin for four hours, then lysed and blotted with indicated antibodies. (B) H1703 was treated with 5 µM SAR245409, 5 µM KU-0063794, or 100 nM rapamycin for four hours, then lysed and blotted for indicated proteins. (C) Cells (TS543, panels (a) and (b); H1703, panels (c) and (d)) were treated with rapamycin for five days, then analyzed for proliferation (panels (a) and (c)) and induction of cell death (panels (b) and (d)). (D) Cells were treated with KU-0063794 for five days, then analyzed for proliferation (left panel) or induction of cell death (right panel). All graphs depict mean±SEM.
Figure 22B:
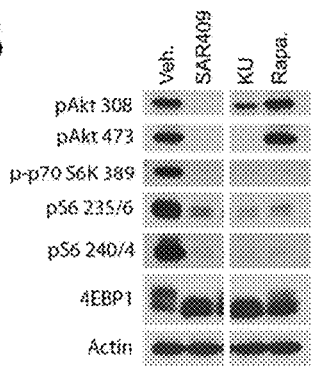
Figure 22C:
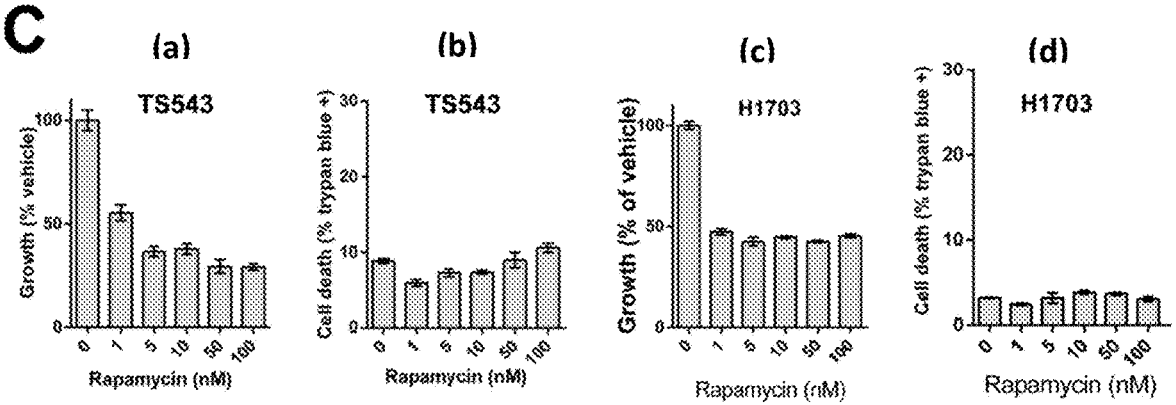

To determine if inhibition of mTOR alone is sufficient to induce cell death, the lines TS543 and H1703 were treated with rapamycin, an allosteric inhibitor of the TORC1 complex. With both lines, robust inhibition of TORC1 signaling (pS6 Ser235/6 and Ser240/4) was seen but not TORC2 functions (pAkt Ser473) (FIGS. 22A and 22B). Proliferation was inhibited in both lines, but there was no induction of cell death (FIG. 22C). H1703, S5472, and TS543 cells were treated with an mTOR kinase inhibitor KU-0063794, which inhibits both TORC1 and TORC2 complexes. both TORC1 (pS6 Ser235/6 and Ser 240/4) and TORC2 (pAkt Ser473) pathways (FIG. 22B) were inhibited in H1703 cells.

Figure 22D:
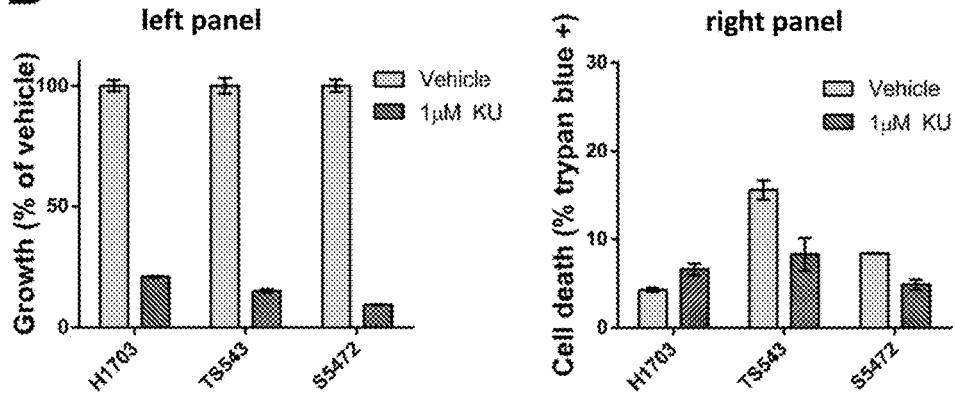

Although all three lines saw proliferation arrest, there was no induction of cell death (FIG. 22D).

p110α Drives Oncogenic Survival in a PDGFR Driven Glioma Line.

To determine if PI3K inhibition alone would be sufficient to induce cell death in PDGFR driven lines that are sensitive to combined PI3K/mTOR inhibition, TS543 cells were treated with pan-Class I PI3K inhibitor GDC-0941, or an alpha p110 specific PI3K inhibitor BYL-719. With both drugs the PI3K/mTOR pathway was inhibited and induction of cell death was observed (FIGS. 23A and B).

Oncogenic PDGFRA Signaling Requires PI3K.

Figures 24A, 24B, 24C:
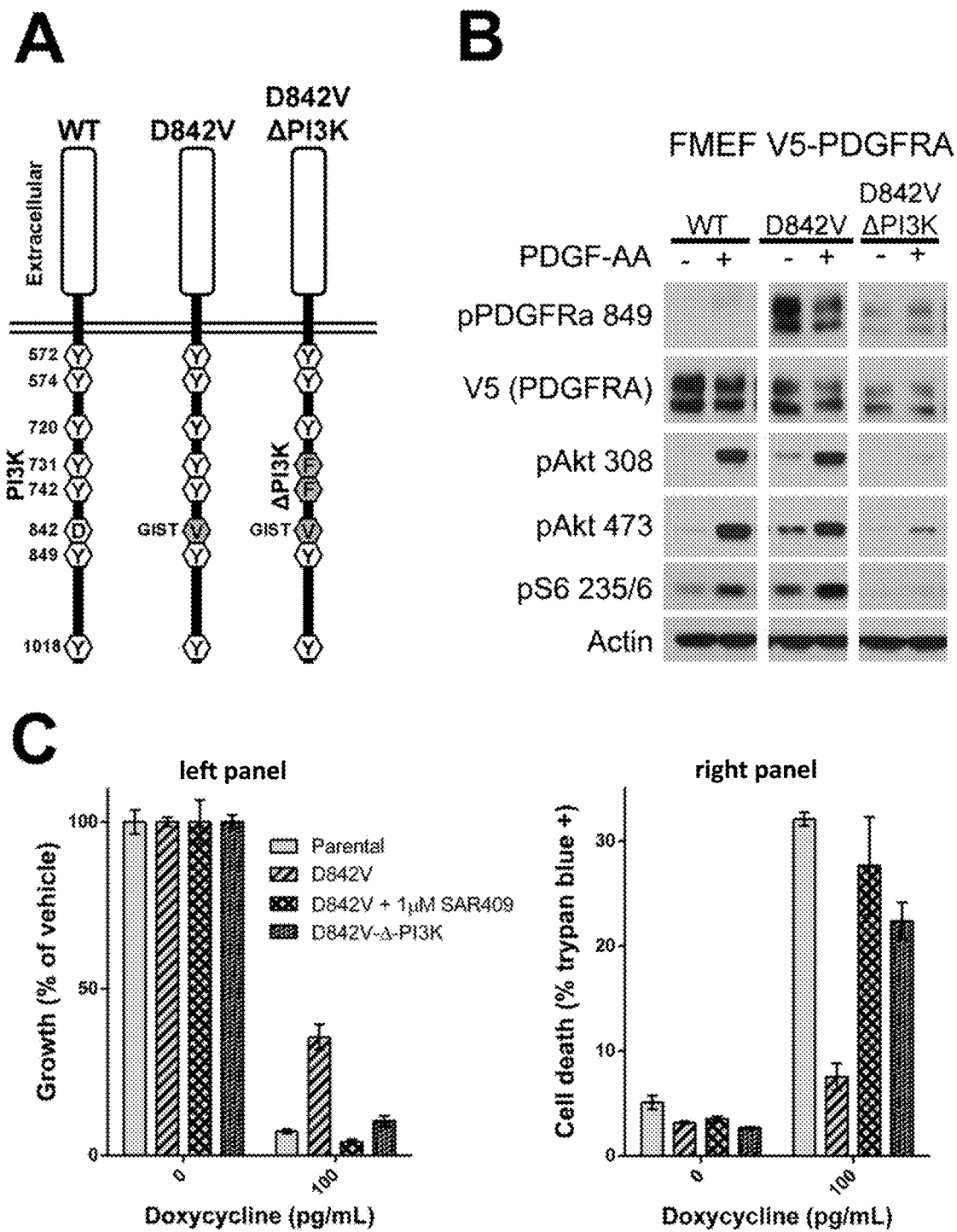
FIGS. 24A-24C: PI3K signaling is required for PDGFRA oncogenic signaling. (A) Cartoon depicting the location of the mutations made to PDGFRA. The GIST mutation is change of aspartic acid 842 to valine (D842V). The PI3K interaction sites of PDGFRA are at tyrosines 731 and 742, these amino acids were changed to phenylalanines (Y731F, Y742F, referred to as ΔPI3K). Mutations were created in a pLenti6 V5-tagged WT-PDGFRA plasmid. (B) Mutations were expressed in FMEF cells which are derived from PDGFRA/PDGFRB null mice. FMEF cells were transduced with lentivirus expressing the indicated V5-tagged PDGFRA receptor, then selected. Cells were serum starved overnight, then treated with 5 ng/mL of PDGF-AA ligand for five minutes, then lysed and blotted with indicated antibodies. WT PDGRA expressing cells only have activation of downstream PI3K/mTOR signaling in the presence of PDGF-AA ligand. D842V expressing cells have ligand-independent activity of the PDGFRA receptor and PI3K/mTOR pathway. D842VΔPI3K have ligand independent activity of the PDGFRA receptor, but do not have any ligand independent or ligand induced activity of downstream PI3K/mTOR signaling (C) PI3K signaling is necessary for PDGFRA oncogenic rescue. S5472 cells were infected with lentivirus containing either D842V or D842VΔPI3K PDGFRA, and selected. Lines were treated with doxycycline for five days, then analyzed for proliferation (left panel) and viability (right panel). Parental lines require ligand for growth and survival. D842V expression rescues this ligand dependence, but this rescue requires PI3K activity. Co-combinant treatment of D842V-S5472 cells with 1 µM SAR245409 and doxycycline ablates ligand-independent growth and survival. Lines expressing D842VΔPI3K PDGFRA cannot rescue ligand dependence.

By aligning mouse ad human PDGFRA sequences, it was determined that the tyrosines used to interact with PI3K were at identical locations in mice and humans. Site directed mutagenesis was used to change these two tyrosines to phenylalaines (FIG. 24A). These mutations are sufficient to block all ligand dependent and independent activation of PI3K in PDGFRA (FIG. 24B). These mutations were combined with a ligand independent PDGFRA mutation found in gastrointestinal stromal tumor patients (GIST): D842V (Heinrich et al., 2003). D842V mutant PDGFRA has ligand independent activity (Hirota et al., 2003). Expression of this mutation is sufficient to rescue ligand dependence in the S5472 line (FIG. 24C). When ligand withdrawal was combined with inhibition of PI3K and mTOR through co-combinant treatment with SAR245409 and doxycycline, expression of D842V is no longer sufficient to rescue dependence. Expression of D842V PDGFR incapable of interacting with PI3K (D842VΔPI3K) cannot rescue ligand dependence of S5472 cells. These results show that PDGFRA requires PI3K activity for growth and survival, and that ablation of this activity through targeted inhibition or ablation of PDGFRA/PI3K interaction can result in cessation of cell proliferation and viability.

Figures 4A, 4B:
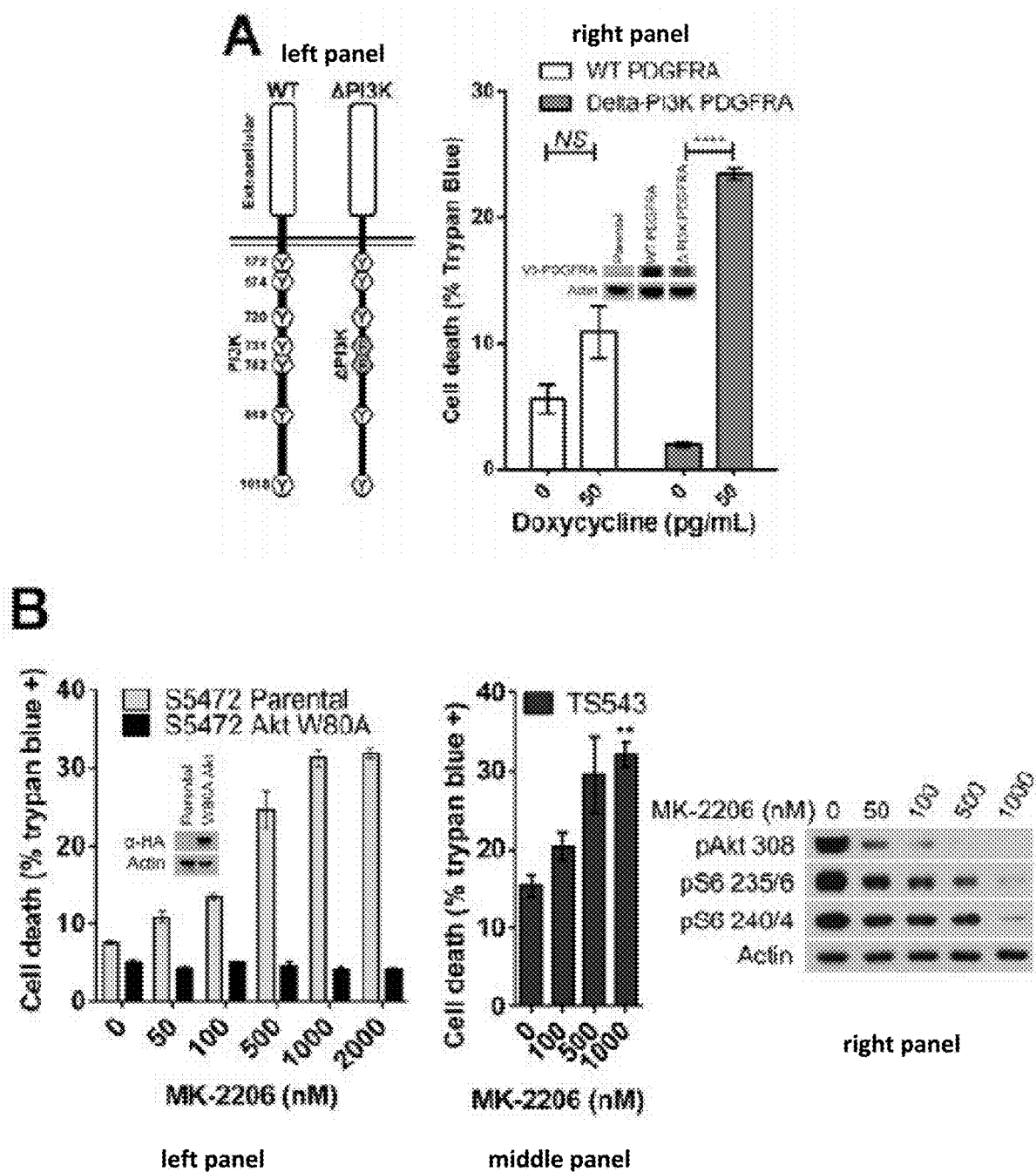
FIGS. 4A-4E: PI3K activity is required for tumor maintenance in PDGFR-driven GBM. (A) PDGFR ΔPI3K mutant cannot support survival of S5472 GBM cells. Left panel, cartoon of the PDGFR Y731F/Y742F double mutant which is unable to recruit PI3K. Right panel, % Trypan blue positive cells after five day doxycline treatment in S5472 cells engineered to overexpress wildtype PDGFRA (WT PDGFRA) or the PDGFR Y731F/Y742F mutant (delta-PI3K PDGFRA). Cells were treated with vehicle or doxycycline for five days to downregulate expression of the PDGFB ligand. Inset, Western of V5-epitope tagged exogenous PDGFRA. (B) Requirement of the serine-threonine kinase Akt for survival of GBM cells with oncogenic PDGFR. Left panel, % Trypan blue positive S5472 cells after five day treatment with the allosteric Akt inhibitor MK-2206 (mean±SEM). A drug-resistant, HA-epitope tagged AKT1 allele (W80-AKT1) (inset, Western Blot) protects from MK-2206 induced cell death. Middle panel, % Trypan blue positive TS543 cells after five day treatment with the allosteric Akt inhibitor MK-2206 (mean±SEM). Right panel, Western Blot of TS543 cells treated with MK-2206 for four hours. (C) Rapamycin inhibits tumor cell proliferation (left panel) and mTORC1 activity (right panel) in TS543 GBM cells, but does not induce cell death (middle panel). (D) Inhibition of mTOR (right panel, Western Blot) accompanies cell death induction (% Trypan-blue positive cells) by the PDGFR inhibitor imatinib (left panel) and the class I PI3K inhibitor GDC-0941 (Raynaud et al., 2009) (middle panel). (E) Synergistic cell death induction by combination of Akt and mTOR inhibition. Top panel, TS543 cells were treated with MK-2206 and vehicle or 10 nM rapamycin in combination. Cells were treated for five days, then analyzed for cell death via Trypan blue exclusion. Bottom panel, TS543 cells were treated with indicated compounds for four hours, then lysed and immunoblotted with indicated antibodies. Graphs depict mean values±SEM. P values for figure are indicated *≤0.05, ≤0.01, *≤0.001, NS not significant.
Figure 10:
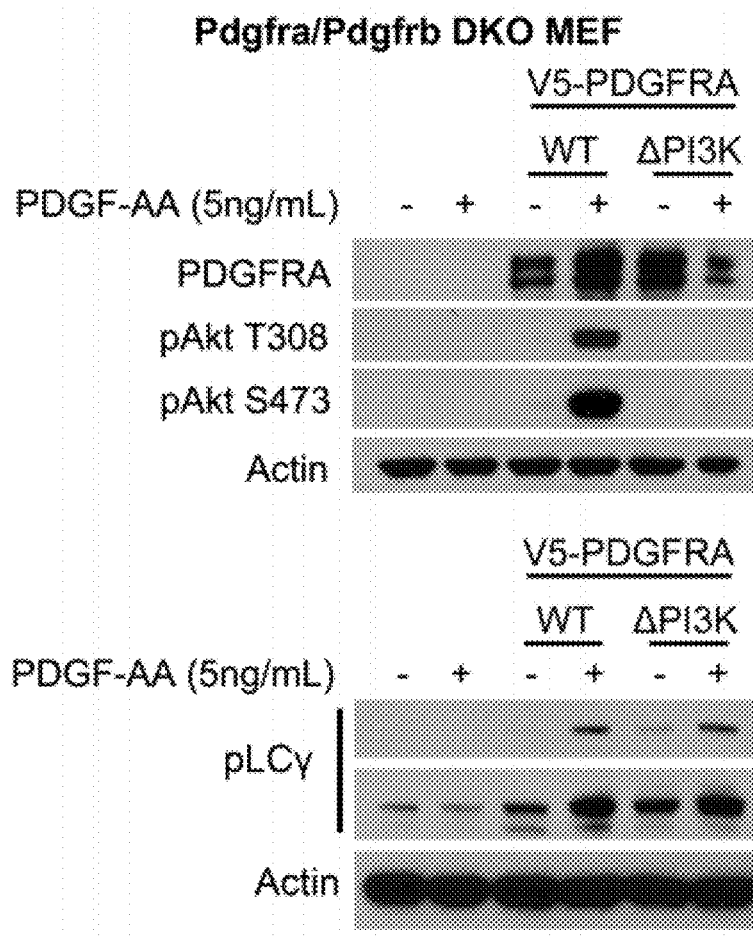
FIG. 10: The Y731F/Y742F PDGFRA mutant does not activate AKT, but is able to activate phospholipase C-γ. Human WT PDGFRA or Y731F/Y742F PDGFRA (labeled ΔPI3K PDGFRA) were stably expressed in mouse knockout MEFs lacking both PDGFRA and PDGFRB receptors. The lines were serum starved overnight, then stimulated with PDGF-AA ligand (5 ng/mL) for five minutes. Cells were lysed and blotted with the indicated antibodies.

To provide genetic evidence that PI3K is required for the survival of PDGFR-driven GBM cells, we took advantage of a previously characterized PDGFRA mutant with tyrosine to phenylalanine substitutions at the PI3K binding sites (Y731F/Y742F) (Kazlauskas and Cooper, 1989; Yu et al., 1991). In Pdgfra/Pdgfrb double knockout (DKO) mouse embryo fibroblasts, this mutant failed to activate Akt but was able to activate phospholipase C-γ, another branch of PDGFR signaling (Andrae et al., 2008) (FIG. 10). When expressed in S5472 GBM cells, this mutant—unlike wild-type PDGFRA—failed to protect them from cell death following doxycyline-induced downregulation of ligand (FIG. 4A).

Contribution of mTOR to GBM Cell Survival.

Figure 4C:
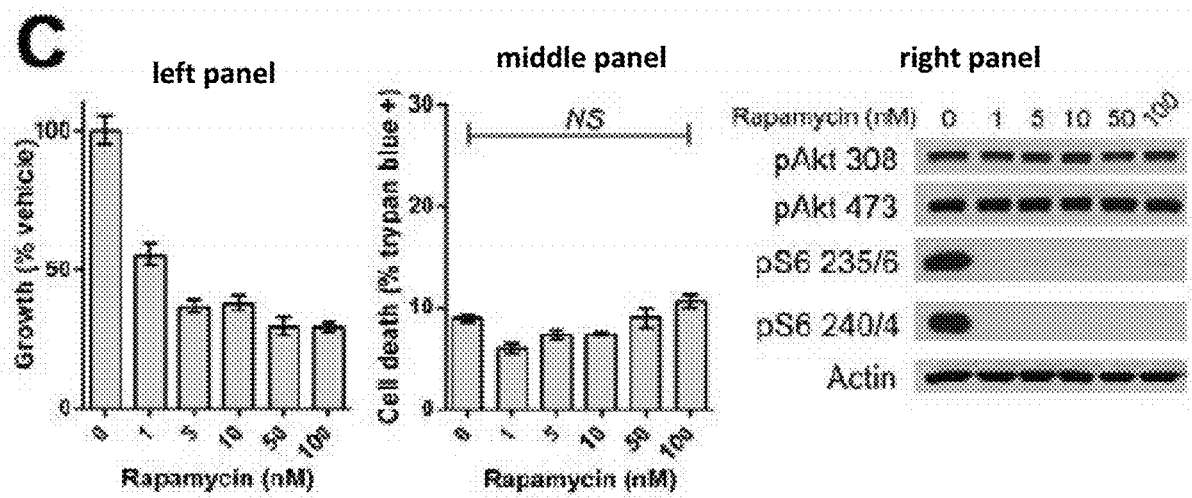
Figure 4D:
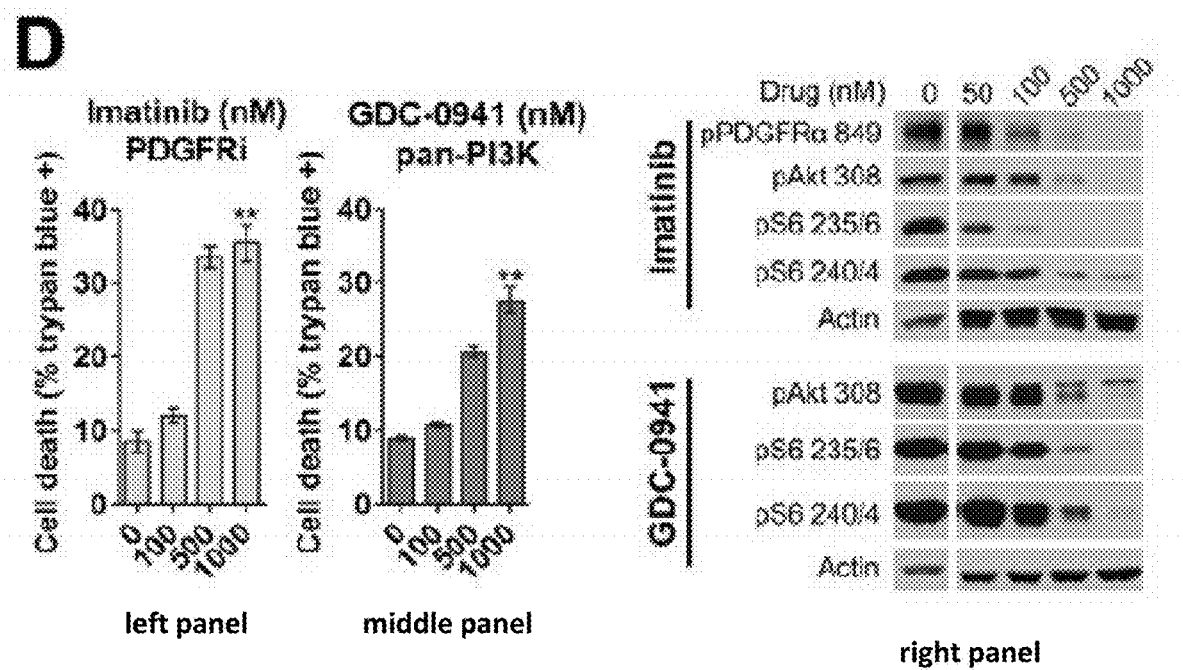
Figure 4E:
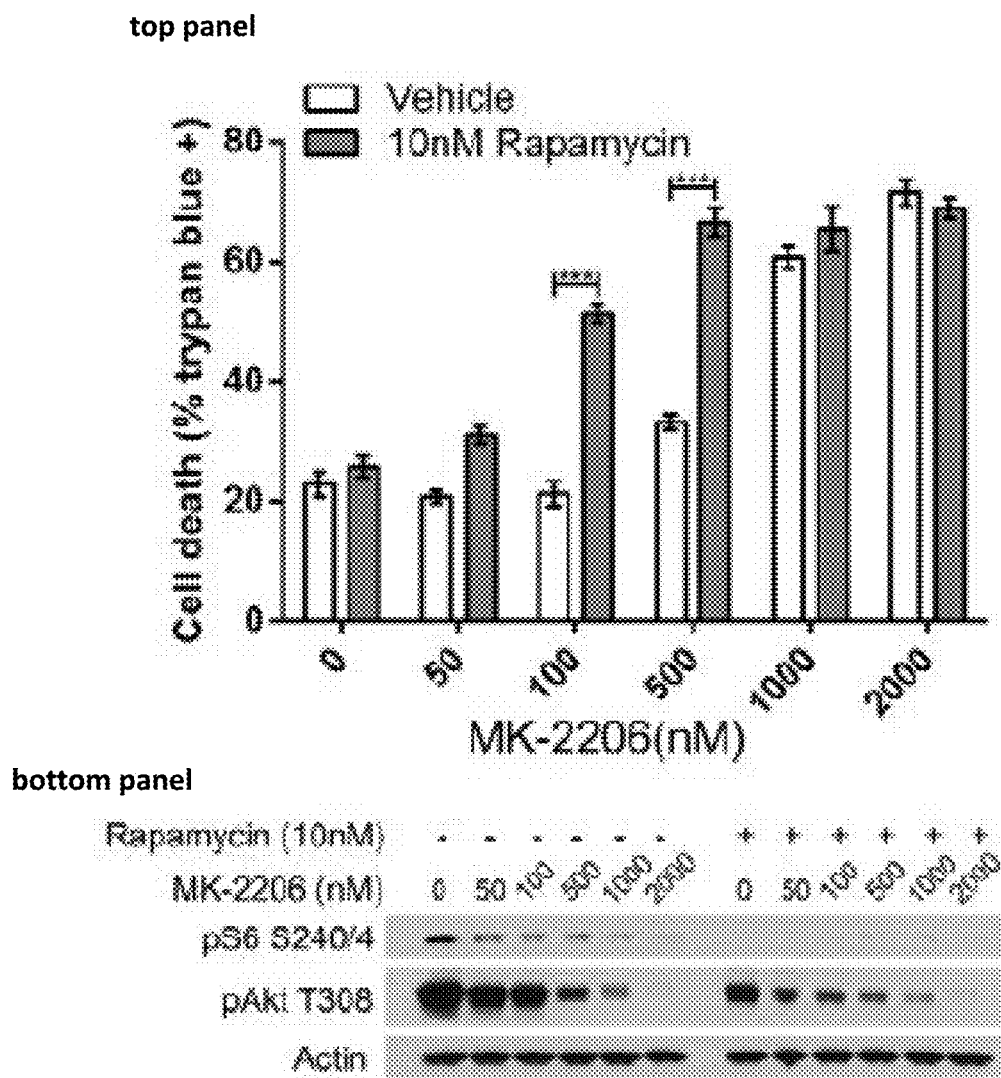
Figures 11A, 11B:
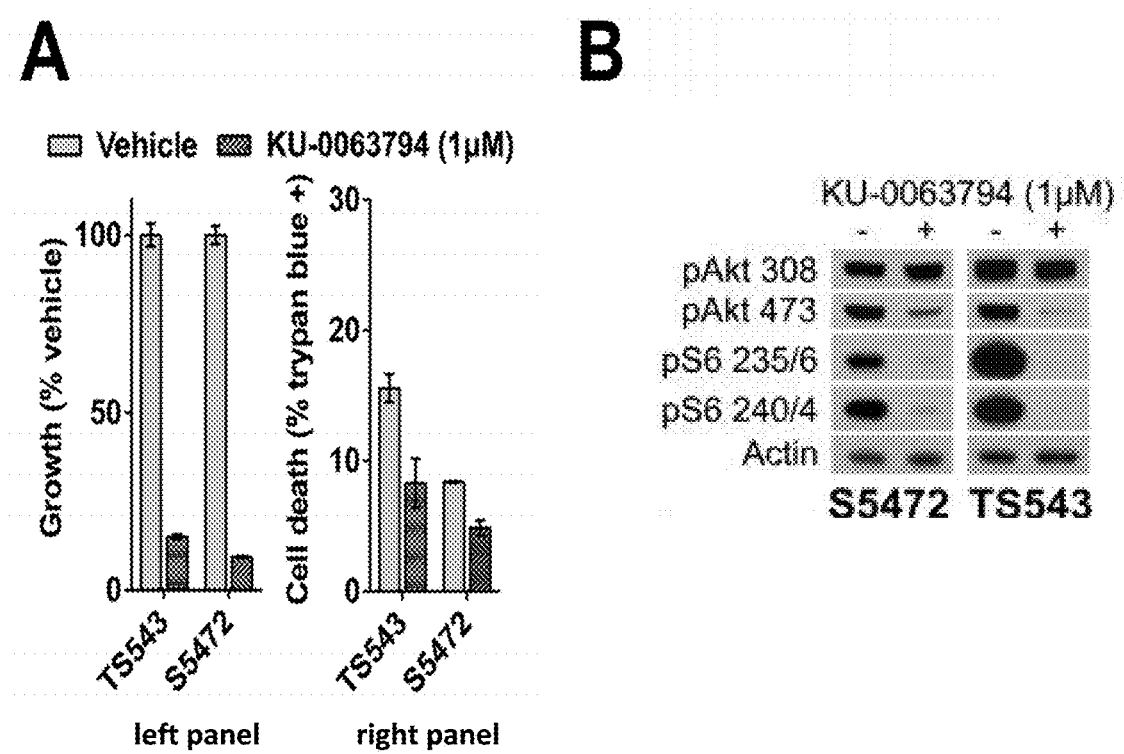
FIGS. 11A-11B: mTOR kinase inhibition causes growth arrest but not cell death in TS543 and S5472 cells. (A) Left panel, growth inhibition (% vehicle) after five day treatment with mTOR kinase inhibitor KU-0063794. Bars represent mean±SEM. Right panel, % Trypan blue positive cells after five day drug treatment. (B) Western Blot of TS543 and S5472 cells treated with KU-0063794 for four hours.

The contribution of mTOR to the survival of GBM cells with aberrant PDGFRA activity was examined. Inhibition of mTORC1 by rapamycin (FIG. 4C) or inhibition of both mTOR complexes by the TOR kinase inhibitor KU-0063794 (Garcia-Martinez et al., 2009) (FIGS. 11A and 11B) markedly impaired tumor cell proliferation, but was not sufficient to induce cell death. However, mTOR inhibition consistently accompanied cell death following the blockade of upstream PDGFR pathway members PDGFR (FIG. 4D, left panel), PI3K (FIG. 4D, middle panel), and Akt (FIG. 4B). Furthermore, we observed a marked increase in cell death induction when we combined the mTORC1 inhibitor rapamycin with a dose of MK2206 that only partially (and indirectly) blocked mTOR (FIG. 4E). These results suggest that mTOR inhibition is required, but not sufficient, for cell death induction by PI3K inhibitors in PDGFR-driven GBM cells, reminiscent of recent observations with growth factor pathway inhibitors in other genetic contexts (Elkabets et al., 2013; Corcoran et al., 2013).

Role of Akt in Tumor Maintenance.

The serine-threonine kinase Akt is a critical mediator of many PI3K functions (Pearce et al., 2010). Thus, inhibition of Akt might be similarly deleterious to PDGFR-driven GBM cells as inhibition of PI3K itself. To examine the role of Akt, TS543 and S5472 GBM cells were treated with the allosteric Akt inhibitor MK-2206 (Hirai et al., 2010) resulted in dose-dependent cell death. Expression of an AKT1 allele with a mutation at a critical MK2206-binding residue (tryptophan 80) (Green et al., 2008; Wu et al., 2010), completely protected S5472 GBM cells from cell death induction by MK2206 (FIG. 4B), providing genetic evidence for the critical role of Akt for tumor maintenance.

Discussion.

The studies described in this Example investigated whether cell lines which are driven by PDGFR signaling, either through amplification of the receptor or through constitutive ligand expression, require PI3K pathway activity for survival and proliferation. Treatment with dual PI3K/mTOR kinase inhibitors was found to ablate cell growth and induce apoptosis in PDGFR driven lines, both in vitro and in vivo. TORC1 activity is required for proliferation of these lines, as inhibition with either rapamycin or KU-0063794 blocked cell growth in PDGFR driven lines. However inhibition of either TORC1 or mTOR kinase activity did not result in apoptosis in these lines, suggesting that mTOR activity is not required for survival. The PI3K/mTOR pathway does not drive cellular survival in all glioma lines, in particular lines with mutated or amplified EGFR saw no change in survival when treated with PI3K/mTOR inhibitors, despite inhibition of the pathway to the same extent as a PDGFRA driven glioma line. Finally, it was found that PI3K activity is required for PDGFRA oncogenic function. Although PDGFRA can regulate a number of pathways, including SRC family kinases and PLCγ, ablation of PI3K interaction was sufficient to completely block oncogenic survival and growth in a PDGFR ligand driven system.

In the analysis of the SAR245408 and SAR245409 clinical trial in glioma patients described in Example 1, an outlier response was discovered in the only patient with amplified PDGFRA. As a follow on to this discovery, the findings described in Example 2 demonstrated that this response may be generalizable to all glioma patients with tumors driven by PDGFR signaling.

Example 3

Illustrative Materials & Methods

Electrochemiluminescent Detection of pS6RP and pAkt. pS6RP Ser240/4 (K150DFD-1) and pAkt Ser473/total Akt (K15100D-1) assays were purchased from MescoScale Discovery and performed as described by the kit on fresh cell lysates, or on lysed frozen tumor sections. Assays were read on the SECTOR™ SI2400 imager.

Immunohistochemistry and Comparative Pathway Analysis.

Immunohistochemical (IHC) staining of patient samples was performed on formalin-fixed paraffin-embedded (FFPE) tumor tissues collected at the initial surgery and recurrent tumor surgery. Slides were stained with phospho-S6 Ser235/6 (Cell Signaling 4872), phospho-4E-BP1 Thr37/46 (Cell Signaling 2855), phospho-p70S6K Thr389 (Cell Signaling 9205), phospho-PRAS40 Thr246 (Cell Signaling 2997), and Ki-67 (Vector Labs VP-RM04). Tumor sections were deparaffinized in xylene and rehydrated in an ethanol gradient. Antigen retrieval was performed on sections by treating with citrate buffer (0.01M, pH 6.0) in a microwave oven for 20 minutes. Endogenous peroxidase was quenched with 3% $H_2O_2$/methanol. Slides were incubated with primary antibodies at 4° C. overnight. Slides were rinsed, then secondary antibodies (rabbit, Vector Labs PI-1000) were applied. Immunoreactivity was detected using NovaRED Peroxidase Substrate kit (Vector Labs SK-4800) and sections were counterstained with hematoxylin.

To analyze pathway inhibition, three representative tumor images from each slide stained with phospho-proteins were taken, after determining the presence of tumor cells based on hematoxylin staining evaluation. An image was also collected from normal tissue on the same slide. Individual cells within each image were separated automatically by Olympus Mircosuite BV35V 3.2 software. Staining index (SI) was calculated by quantifying and calculating the mean saturation of red-brown hue range of each cell of each image, averaging the cell saturation for each image, then averaging the cell saturation of the three tumor images. The tumor to normal ratio was calculated by dividing the average of the tumor images by the average of the normal tissue image. Initial surgical samples were compared to post-drug treated resected surgical samples, and the percentage increase or decrease of each stain was calculated.

To determine the Ki-67 labeling index, slides were analyzed as with the phospho-proteins, and the number of positively stained and total number of cells was determined for each image. The percentage of Ki-67 positive cells was calculated for each image, then the three images were averaged.

The following antibodies were used for IHC: p-S6 (Ser235/236): Cell Signaling, #4857, rabbit monoclonal, 1:25; p-4EBP1 (Thr37/46): Cell Signaling, #2855, rabbit monoclonal, 1:400; p-p70S6K (S6K1, Thr389): Cell Signaling, #9205, rabbit polyclonal, 1:100; p-PRAS40 (Thr246): Cell Signaling, #2997, rabbit monoclonal, 1:200; Ki-67: Vector Labs, VP-RM04, rabbit monoclonal, 1:500. PTEN (DAKO, M3627, dilution 1:350). Image quantification was performed as previously described (Cloughesy et al., 2008). IHC for was scored as previously described (Mellinghoff et al., 2005).

Comparative Genomic Hybridization.

DNA was isolated from patient tumors and cell lines using Qiagen DNeasy Blood and Tissue kit (Qiagen 69506). Four micrograms of DNA were analyzed using 1 million probe Agilent human array using Roche gDNA as a control sample. Genomic gains or losses were scored using CGH Analytics Software (Agilent). Aberrations of $log_2$ ratio less than −0.3 were considered losses, and aberrations of $log_2$ ratio greater than 0.3 were considered gains. Array pictures were plotted using the Intergrative Genomics Viewer (IGV, Broad Institute) with red as gains and blue as losses.

Fluorescence In Situ Hybridization.

FISH analysis was performed on FFPE tissue sections using Locus and Centromere-Specifc probes (Abbott Molecular, Inc for EGFR (7p12/CEP7) and PDGFR/CEP4 (4q12 Tri color mixed with CEP4). FFPE tissue sections (4 um) were deparaffinized in xylene solution, dehydrated in ethanol and further processed using Vysis paraffin pretreatment kit and hybridized following protocol for FFPE sections (Abott Molecular) routinely employed in the laboratory. FISH analysis was then performed using fluorescence microscope (Axio; Carl Zeiss AG, Jena, Germany) and ISIS Imaging System (Meta Systems GmbH, Altlussheim, Germany). A total of 200-300 nuclei in six different areas per section were then analyzed for tumors cells exhibiting focal (area specific) or high level gene amplification for respective probes.

Cell Culture and Reagents.

FMEF cells were generated by the Kazlauskas laboratory (Heuchel et al., 1999) by crossing mice with heterozygous loss of Pdgfa (Soriano, 1997) and Pdgfrb (Soriano, 1994). Embryos null for both receptors were disassociated and immortalized by infecting with simian virus 40 large T antigen. S5472 cells were generated by the Israel laboratory (Hitoshi et al., 2008). Primary neurosphere lines TS516, TS543, TS603, TS616, and TS676 were derived from patient tumors treated at MSKCC. They were maintained in human formulation NeuroCult media (Stem Cell Technologies 05751) with 20 ng/mL EGF and 10 ng/mL bFGF.

TABLE 8

Examples of cell lines and cell culture reagents.

| Cell line | Source | Product number (if applicable) | Culture media |
|---|---|---|---|
| 293T/17 | ATCC | CRL-11268 | DMEM + 10% FBS |
| BT474 | ATCC | ATCC HTB-20 | DMEM + 10% FBS |
| FMEF | Douglas Wheeler | — | DMEM + 10% FBS |
| H1703 | ATCC | ATCC CRL-5889 | RPMI + 10% FBS |
| HCC4006 | ATCC | ATCC CRL-2871 | DMEM + 10% FBS |
| KNS-81-FD | Japanese Collection of Research Bioresources | JCRB IFO50444 | DMEM:F12 |
| S5472 | Mark Israel | — | DMEM:F12 + B27 |
| SF-268 | NCI | — | DMEM + 10% FBS |
| TS516, TS543, TS603, TS616, TS676 | | — | Human NeuroCult |

Generation of Constructs and Cell Lines.

PDGFRA pDONR223 plasmid was obtained from Addgene (Plasmid 23892) and the Addgene-noted point mutation (M260I) was mutated back to a methionine. PDGFRA was then cloned into the pLenti6/V5-DEST vector (Invitrogen V496-10) using the Gateway system (Life Technologies 11791020). Mouse and human PDGFRA transcripts were aligned to confirm the location of PI3K tyrosine docking sites noted in mouse PDGFRA (Klinghoffer and Hamilton, 2002) in human PDGFRA. All mutations were created using QuikChange II XL (Agilent Technologies 200521).

pLenti6 PDGFRA plasmids were co-transfected with packaging vectors pMD2G and pPAX2 into 293T cells using the calcium phosphate method. Lenti-virus particles were collected 36 and 60 hours post transfection and concentrated using Lenti X (Clontech 631232). To infect FMEF cells, two rounds of concentrated virus and 8 ug/mL of polybrene were placed on cells and left over night. Cells were selected with blasticidin, then fluorescence-activated cell sorting (FACS) for human PDGFRA (PDGFA Alexa Fluor 647 tagged antibody from BD Pharmingen (BD 562798)). To infect S5472, cells were single cell disassociated with Accumax (Innovative Cell Technologies AM105), then spin-fected with concentrated virus particles and 8 ug/mL of polybrene for 1.5 hours at 1000 RCF. Cells were selected and sorted in the same method as the FMEF lines.

Western Blotting.

Cell lysates for western blots were harvested in cell lysis buffer (Cell Signaling 9803) supplemented with a protease inhibitor cocktail (Calbiochem cocktail II 524625) and phosphatase inhibitor cocktail (Calbiochem cocktail III 524627). Lysates were sonicated, centrifuged, then quantified (Bio-Rad DC Protein Assay 500-0113, 500-0114, and 500-0115). Samples were normalized to one another, then a reducing loading buffer was added. Samples were run on SDS-PAGE gels and semi-dry transferred to nitrocellulose membranes.

Antibodies for western blots were all from Cell Signaling Technology with the following exceptions: actin (Sigma), total PDGFRA (Santa Cruz), and V5 epitope (Invitrogen).

Cellular Proliferation Assays.

For growth assays performed on non-adherent cell lines (primary human neurosphere lines and S5472 cells) cells were single cell disassociated with Accumax, then counted using the Beckman Coulter Vi-Cell XR Cell Viability Analyzer. Cells were plated in a 6 cm dish in triplicate for each vehicle or drug sample. After five days in culture, each plate was individually spun down, Accumax disassociated, and counted with the Vi-Cell. The Vi-Cell uses trypan blue-exclusion as a measure for viable cells, trypan blue positive cells were used to calculate the percentage of cell death in each sample. The average and standard error of the mean was graphed using GraphPad Prism 6.

Growth assays performed on adherent cell lines were trypsanized, counted, and plated into 6 cm dishes. The next day media was removed, and replaced with reduced serum media (5% FBS) with drug or vehicle in triplicate for each concentration. After five days in culture, cells were analyzed in the same manner as non-adherent lines.

In Vivo Experiments.

The mouse replication competent ALV splice acceptor (RCAS/t-va) system was used as previously described (Hambardzumyan et al., 2009). Df-1 cells were purchased from ATCC and cells were grown at 39° C. according to ATCC instructions. Transfection with RCAS-PDGF-B-HA was performed using Fugene 6 transfection kit (Roche #11814443001) according to manufactures instructions. 6-8 week-old nestin-tv-a/ink4a-arf−/− mice were anesthetized with ketamine (0.1 mg/g) and xylazine (0.02 mg/g) and injected using stereotactic fixation device (Stoelting, Wood Dale, Ill.). One microliter of RCAS-PDGF-B transfected 4×104 Df-1 cells was delivered using a 30-gauge needle attached to a Hamilton syringe. Cells were injected to the right frontal striatum, coordinates bregma 1.5 mm, Lat −0.5 mm, and a depth 2 mm. Thirty days after injection, all mice underwent a brain MRI and were randomized to vehicle or SAR245409 treatment (60 mg/mg). Mice were treated for 10 days and sacrificed after a second MRI.

For the S5472 and TS543 subcutaneous model, 10e6 cells were suspended in a 100 uL mixture of 50% growth media 50% Matrigel (BD 356237). SCID mice were injected subcutaneously in the flank, and once tumors had reached a measurable size, mice were randomized into treatment groups.

Genomic Analyses.

Genomic analyses of tumor DNA from macrodissected frozen tumor and included array comparative genomic hybridization (aCGH) (1 M, Agilent) and full-length sequencing of selected PI3K pathway members (BRAF, EGFR, KRAS, MET, NF1, NRAS, PDGFB, PDGFRA, PDGFRB, PIK3CA, PIK3CB, PIK3CD, PIK3R1, PTEN, RAF1, TSC1, and TSC2) using the Illumina MiSeq with at least 100× coverage per amplicon. Fluorescence in situ hybridization (FISH) was performed on formalin-fixed paraffin embedded (FFPE) tissue sections using Locus and Centromere-Specifc probes (Abbott Molecular, Inc for EGFR (7p12/CEP7) and PDGFR/CEP4 (4q12 Tri color mixed with CEP4). 200-300 nuclei in six different areas per section were analyzed for tumors cells exhibiting focal (area specific) or diffuse gene amplification for respective probes.

Reagents.

SAR408 and SAR409 were provided by Sanofi. GDC-0980, MK-2206, Imatinib, GDC-0941, rapamycin, and KU-0063794 were purchased from Selleck Chemicals. Antibodies for western blots were from Cell Signaling Technology with the following exceptions: actin (Sigma), total PDGFRA (Santa Cruz), and V5 epitope (Invitrogen). Western Blots were performed after four hours of drug treatment unless indicated otherwise. Electroluminescence was used to quantify phosphorylation of Akt and S6 ribosomal protein (FIG. 1B) (Meso Scale Discovery cat # K15100D-1 and cat # K150DGD-1). Cell Proliferation and Viability Assays were performed using a Beckman Coulter Vi-Cell XR Cell Viability Analyzer after five days of drug treatment unless indicated otherwise.

REFERENCES

Alessi et al. (1996). EMBO J. 15, 6541-6551.
Alessi et al. (1997). Curr. Biol. 1, 776-789.
Andrae et al. (2008). Genes Dev. 22, 1276-1312.
Andrews et al. (1999). Invest. Ophthalmol. Vis. Sci. 40, 2683-2689.
Athanassiou et al. (2005). J. Clin. Oncol. 23, 2372-2377.
Backer et al. (1992). EMBO J. 11, 3469-3479.
Bagci-Onder et al. (2011). Cancer Res. 71, 154-163.
Barker (1982). Cancer Genet. Cytogenet. 5, 81-94.
Bayascas (2010). Phosphoinositide 3-Kinase in Health and Disease, pp. 9-29.
Bellacosa et al. (1991). Science (80) 254, 274-277.
Bigner et al. (1990). Cancer Genet. Cytogenet. 154, 141-154.
Bollag, G. et al. Nature 467, 596-599.
Bozulic et al. (2008). Mol. Cell 30, 203-213.
Brennan et al. (2009). PLoS One 4, e7752.
Brennan et al. (2013). Cell 155, 462-477.
Byun et al. (2003). Int. J. Cancer 104, 318-327.
Cantley et al. (1999). Proc. Natl. Acad. Sci. U.S.A. 96, 4240-4245.
Carracedo et al. (2008). J. Clin. Invest. 118, 3065-3074.
Castellano et al. (2011). Phosphoinositide 3-Kinase in Health and Disease, pp. 143-169.
Central Brain Tumor Registry of the United States (2012). CBTRUS Statistical Report: Primary Brain and Central Nervous System Tumors Diagnosed in the United States in 2004-2008.
Cerami et al. (2012). Cancer Discov. 2, 401-404.
Chandarlapaty et al. (2011). Cancer Cell 19, 58-71.
Chang et al. (2005). Invest. New Drugs 23, 357-361.
Clarke et al. (2003). Oncogene 22, 722-733.
Cloughesy et al. (2008). PLoS Med. 5, e8.
Cloughesy et al. (2013). ASCO Annual Meeting Proceedings.
Coffer & Woodgett. (1992). Eur. J. Biochem. 205, 1217.
Corcoran et al. (2013). Sci Transl Med 5, 196ra198.
Daneman (2012). Ann. Neurol. 72, 648-672.
Dang et al. (2009). Nature 462, 1-18.
DeYoung et al. (2008). Genes Dev. 22, 239-251.
Druker et al. (2001). N. Engl. J. Med. 344, 1031-1037.
Druker et al. (2006). N. Engl. J. Med. 355, 2408-2417.
Elkabets et al. (2013). Sci. Transl. 5, 1-28.
Faber et al. (2009). Proc Natl Acad Sci USA 106, 19503-19508.
Fan et al. Cancer Cell 9, 341-349 (2006).

Frederick et al. (2000). Cancer Res. 60, 1383-1387.
Gao et al. (2013). Sci. Signal. 6, p11.
Garcia-Martinez et al. (2009). Biochem J 421, 29-42.
Gonzalez & McGraw (2009). Cell Cycle 8, 2502-2508.
Grabiner et al. (2014). Cancer Discov.
Green et al. (2008). J Biol Chem 283, 27653-27667.
Vander Haar et al. (2007). Nat. Cell Biol. 9, 316-323.
Hambardzumyan et al. (2009). Transl. Oncol. 2, 89-95.
Han et al. (2000). Cancer Res. 60, 3147-3151.
Hanahan et al. (2011). Cell 144, 646-674.
Hara et al. (1998). J. Biol. Chem. 273, 14484-14494.
Heinrich et al. (2003). Science 299, 708-710.
Heitman et al. (1991). Science 253, 905-909.
Heldin. (2012). Ups J Med Sci 117, 83-91.
Heldin & Westermark (1999). Physiol. Rev. 79, 1283-1316.
Heldin et al. (1998). Biochim. Biophys. Acta 1378, F79-113.
Henson et al. (2005). Lancet Oncol. 6, 167-175.
Heuchel et al. (1999). Proc. Natl. Acad. Sci. U.S.A. 96, 11410-11415.
Hirai et al. (2010). Mol. Cancer. Ther. 9, 1956-1967.
Hirota et al. (2003). Gastroenterology 125, 660-667.
Hitoshi et al. (2008). Cancer Res. 68, 8507-8515.
Hochberg & Pruitt (1980). Neurology 30, 907.
Holland et al. (2008). Genes Dev 12, 3675-3685.
Huang et al. (1997). J. Biol. Chem. 272, 2927-2935.
Huang et al. (2009). Sci. Signal. 2, re6.
Ilic & Roberts (2011). Phosphoinositide 3-Kinase in Health and Disease, pp. 55-78.
Inoki et al. (2002). Nat. Cell Biol. 4, 648-657.
Iyer et al. (2012). Science 338, 221.
Jaber et al. (2012). Proc. Natl. Acad. Sci. U.S.A. 109, 2003-2008.
Jaiswal et al. (2009). Cancer Cell 16, 463-474.
Kanakaraj et al. (1991). Biochemistry 30, 1761-1767.
Kazlauskas & Cooper (1989). Cell 58, 1121-1133.
Kleihues & Ohgaki (1999). Neuro. Oncol. 1, 44-51.
Klempner et al. (2013). Cancer Discov 3, 1345-1354.
Klinghoffer & Hamilton (2002). Dev. Cell 2, 103-113.
Koul et al. (2012). Clin. Cancer Res. 18, 184-195.
Kris et al. (2003). JAMA 290, 2149-2158.
Kumabe et al. (1992). Oncogene 7, 627-633.
Laplante & Sabatini (2009). J. Cell Sci. 122, 3589-3594.
Laplante & Sabatini (2012). Cell 149, 274-293.
Lee et al. (2006). PLoS Med. 3, e485.
Li et al. (1997). Science 275, 1943-1947.
Liang et al. (2005). Proc. Natl. Acad. Sci. U.S.A. 102, 5814-5819.
Liu et al. (2009). Mol. Cancer Ther. 8, 2204-2210.
Ma et al. (2000). Oncogene 19, 2739-2744.
Maher et al. (2006). Cancer Res. 66, 11502-11513.
Maira et al. (2010). Phosphoinositide 3-Kinase in Health and Disease.
McDermott et al. (2009). Cancer Res. 69, 3937-3946.
Mellinghoff (2012). Curr. Top. Microbiol. Immunol. 355, 135-169.
Mellinghoff & Schultz (2012). Therapeutic Kinase Inhibitors, pp. 135-169.
Mellinghoff et al. (2005). N. Engl. J. Med. 353, 2012-2024.
Mischel et al. (2003). Cancer Biol. Ther. 2, 242-247.
Mora et al. (2004). Semin. Cell Dev. Biol. 15, 161-170.
Neshat et al. (2006). Cancer Res. 66, 1500-1508.
Ohgaki & Kleihues (2007). Am. J. Pathol. 170, 1445-1453.
Ozawa et al. (2010). Genes Dev. 24, 2205-2218.
Panayotou et al. (1992). EMBO J. 1, 4261-4272.
Parsons et al. (2008). Science 321, 1807-1812.
Paugh et al. (2013). Cancer Res. 73, 6219-6229.
Pearce et al. (2010). Nat. Rev. Mol. Cell Biol. 11, 9-22.
Phillips et al. (2006). Cancer Cell 9, 157-173.
Phillips et al. (2013). Brain Pathol. 23, 565-573.
Podsypanina et al. (2001). Proc. Natl. Acad. Sci. U.S.A. 98, 10320-10325.
Prahallad et al. (2012). Nature 483, 100-103.
Prasad et al. (2011). Neuro. Oncol. 13, 384-392.
Proud (2009). Biochem. Soc. Trans. 37, 227-231.
Quintás-Cardama (2006). Mayo Clin. Proc. 81, 973-988.
Raynaud, F. I. et al. (2009). Mol Cancer Ther 8, 1725-1738.
Rodon (2013). Nat Rev Clin Oncol 10, 143-153.
Rong et al. (2006). J. Neuropathol. Exp. Neurol. 65, 529-539.
Salmena et al. (2008). Cell 133, 403-414.
Samuels et al. (2004). Science 304, 554.
Sancak et al. (2010). Cell 141, 290-303.
Sarbassov et al. (2004). Curr. Biol. 14, 1296-1302.
Sarbassov et al. (2005). Science 307, 1098-1101.
Sato et al. (2010). Oncogene 29, 2746-2752.
She et al. (2008). PLoS One 3, e3065.
Siegel et al. (2013). CA. Cancer J. Clin. 63, 11-30.
Snuderl et al. (2011). Cancer Cell 20, 810-817.
Soltoff & Cantley (1996). J. Biol. Chem. 271, 563-567.
Soriano (1994). Genes Dev. 8, 1888-1896.
Soriano (1997). Development 124, 2691-2700.
Sorkin & Goh (2009). Exp. Cell Res. 315, 683-696.
Staal (1987). Proc. Natl. Acad. Sci. U.S.A. 84, 5034-5037.
Staal et al. (1977). Proc. Natl. Acad. Sci. U.S.A. 74, 3065-3067.
Steck et al. (1997). Nat. Genet. 15, 356-362.
Stupp et al. (2005). N. Engl. J. Med. 352, 987-996.
Stupp et al. (2009). Lancet Oncol. 10, 459-466.
Sun et al. (2010). Proc. Natl. Acad. Sci. U.S.A. 107, 15547-15552.
Szerlip et al. (2012). Proc Natl Acad Sci USA 109, 3041-3046.
Tallquist et al. (2000). Genes Dev. 14, 3179-3190.
The Cancer Genome Atlas (2008). Nature 455, 1061-1068.
Turke et al. (2012). Cancer Res. 72, 3228-3237.
Vanhaesebroeck et al. (2010). Nat. Rev. Mol. Cell Biol. 11, 329-341.
Vasudevan & Garraway (2010). AKT Signaling in Physiology and Disease.
Verhaak et al. (2010). Cancer Cell 17, 1-25.
Vivanco et al. (2010). Proc. Natl. Acad. Sci. U.S.A. 107, 6459-6464.
Wagle et al. (2014). Cancer Discov.
Walker & Green (1980). N. Engl. J. Med. 303, 1323-1329.
Wallin et al. (2011). Mol Cancer Ther 10, 2426-2436.
Wan et al. (2007). Oncogene 26, 1932-1940.
Ward et al. (2010). Cancer Cell 17, 225-234.
Wen et al. (2008). N. Engl. J. Med. 359, 492-507.
Wen et al. (2015). Neurooncology.
Wu et al. (2005a). J. Clin. Endocrinol. Metab. 90, 4688-4693.
Wu et al. (2005b). Breast Cancer Res. 7, R609-16.
Wu et al. (2009). Proc. Natl. Acad. Sci. U.S.A. 106, 20258-20263.
Wu et al. (2010). PLoS ONE 5, e12913.
Yan et al. (2009). N. Engl. J. Med. 360, 765-773.
Yarden et al. (2001). Nat. Rev. Mol. Cell Biol. 2, 127-137.
Yu et al. (1991). Mol Cell Biol 11, 3780-3785.
Yu et al. (1998). Mol. Cell. Biol. 18, 1379-1387.
Yu et al. (2014). Mol. Cancer Ther. doi:1535-7163.
Zhang et al. (2003). Nat. Cell Biol. 5, 578-581.
Zhu et al. (2009). Proc. Natl. Acad. Sci. U.S.A. 106, 2712-2716.

While the foregoing invention has been described in some detail for purposes of clarity and understanding, it will be clear to one skilled in the art from a reading of this disclosure that various changes in form and detail can be made without departing from the true scope of the invention. The invention may also be further defined in terms of the following Claims.

The invention claimed is:

1. A method of treating a glioma in a subject in need thereof, the method comprising: (a) determining if a subject with a glioma has an oncogenic PDGFRA mutation, and (b) subsequently administering an effective amount of SAR245409 to the subject, thereby treating the glioma in the subject, wherein the treatment: (i) increases the time to progression in the subject by two-fold or more as compared to the average time to progression for glioma patients that do not have the oncogenic PDGFRA mutation, and/or (ii) results in progression-free survival for at least 6-months following treatment.

2. The method of claim 1, wherein the oncogenic PDGFRA mutation is selected from the group consisting of a PDGFRA mutation that results in a deletion of a portion of the PDGFRA extracellular domain, a PDGFRA mutation that results in constitutive activation of a PDGRFA receptor molecule, a PDGFRA mutation that results in constitutive PDGRFA phosphorylation and AKT activation, a PDGFRA mutation that results in overexpression of a PDGFRA receptor molecule, a PDGFRA mutation that results in increased activity of a PDGRFA receptor molecule, a PDGFRA gene amplification and a focal amplification of the human PDGFRA locus on human chromosome 4q12.

3. The method of claim 1, wherein the oncogenic PDGFRA mutation comprises a mutation in the third IG-like domain of the extracellular domain of PDGRFA located in the region spanning amino acids 202-306 of human PDGRFA.

4. The method of claim 1, wherein the oncogenic PDGFRA mutation comprises one or more of a G228V mutation, a P250S mutation, or a D842V mutation.

5. The method of claim 1, wherein the subject is a human.

6. The method of claim 1, wherein the treatment results in regression of the glioma.

7. The method of claim 1, wherein the subject is human and the subject has no tumor recurrence for at least 6-months after treatment is commenced.

8. The method of claim 1, wherein the subject has glioblastoma.

9. The method of claim 8, wherein the subject has glioblastoma that has recurred following treatment using chemotherapy, radiation therapy, or surgical resection, or any combination thereof.

10. The method of claim 1, wherein the SAR245409 is administered prior to performing surgical resection of the glioma.

11. The method of claim 10, wherein the SAR245409 is administered for a period of 10-28 days prior to performing the surgical resection.

12. The method of claim 1, wherein the SAR245409 is administered after performing surgical resection of the glioma.

13. The method of claim 12, wherein the SAR245409 is administered for a period of at least 20 weeks after the surgical resection.

14. The method of claim 1, wherein the SAR245409 is administered both before and after performing surgical resection of the glioma.

15. The method of any of claims 10-13 or 14, wherein the subject has no tumor recurrence for at least 6-months after the surgical resection.

16. The method of claim 1, further comprising administering an effective amount of an mTOR inhibitor to the subject.

17. The method of claim 16, wherein the mTOR inhibitor is selected from the group consisting of: GDC-0980, CCI-779, KU-0063794, rapamycin, epigallocatechin gallate (EGCG), caffeine, curcumin, resveratrol, sirolimus, temsirolimus, everolimus, ridaforolimus and analogues, variants, and derivatives thereof.

* * * * *